US011343075B2

(12) United States Patent
Snow

(10) Patent No.: US 11,343,075 B2
(45) Date of Patent: May 24, 2022

(54) RAM HASHING IN BLOCKCHAIN ENVIRONMENTS

(71) Applicant: Inveniam Capital Partners, Inc., New York, NY (US)

(72) Inventor: Paul Snow, Austin, TX (US)

(73) Assignee: Inveniam Capital Partners, Inc., New York, NY (US)

( * ) Notice: Subject to any disclaimer, the term of this patent is extended or adjusted under 35 U.S.C. 154(b) by 45 days.

(21) Appl. No.: 17/037,995

(22) Filed: Sep. 30, 2020

(65) Prior Publication Data

US 2021/0226773 A1     Jul. 22, 2021

Related U.S. Application Data

(60) Provisional application No. 63/061,372, filed on Aug. 5, 2020, provisional application No. 62/962,486, filed
(Continued)

(51) Int. Cl.
*H04L 9/06* (2006.01)
*G06F 16/2458* (2019.01)
(Continued)

(52) U.S. Cl.
CPC ........ *H04L 9/0637* (2013.01); *G06F 16/2379* (2019.01); *G06F 16/2465* (2019.01);
(Continued)

(58) Field of Classification Search
CPC ... H04L 9/0637; H04L 9/0643; H04L 9/3218; H04L 9/3239; H04L 2209/38;
(Continued)

(56) References Cited

U.S. PATENT DOCUMENTS

| 4,309,569 A | 6/1982 | Merkel |
| 5,499,294 A | 3/1996 | Friedman |

(Continued)

FOREIGN PATENT DOCUMENTS

| CN | 110392052 | 10/2019 |
| DE | 10128728 | 1/2003 |

(Continued)

OTHER PUBLICATIONS

Watanabe, Hiroki, et al. "Blockchain contract: Securing a blockchain applied to smart contracts." *2016 IEEE International Conference on Consumer Electronics (ICCE)*. IEEE, 2016.
(Continued)

*Primary Examiner* — Mohammed Waliullah
(74) *Attorney, Agent, or Firm* — Koffsky Schwalb LLC

(57) ABSTRACT

Blockchain environments may mix-and-match different encryption, difficulty, and/or proof-of-work schemes when mining blockchain transactions. Each encryption, difficulty, and/or proof-of-work scheme may be separate, stand-alone programs, files, or third-party services. Blockchain miners may be agnostic to a particular coin's or network's encryption, difficulty, and/or proof-of-work schemes, thus allowing any blockchain miner to process or mine data in multiple blockchains. GPUs, ASICs, and other specialized processing hardware components may be deterred by forcing cache misses, cache latencies, and processor stalls. Hashing, difficulty, and/or proof-of-work schemes require less programming code, consume less storage space/usage in bytes, and execute faster. Blockchain mining schemes may further randomize byte or memory block access, further improve cryptographic security.

20 Claims, 45 Drawing Sheets

Related U.S. Application Data on Jan. 17, 2020, provisional application No. 62/963,217, filed on Jan. 20, 2020.

(51) Int. Cl.
*H04L 9/32* (2006.01)
*G06F 16/23* (2019.01)
*G06F 21/60* (2013.01)

(52) U.S. Cl.
CPC .......... *G06F 21/602* (2013.01); *H04L 9/0643* (2013.01); *H04L 9/3218* (2013.01); *H04L 9/3239* (2013.01); *G06F 2216/03* (2013.01); *H04L 2209/38* (2013.01)

(58) Field of Classification Search
CPC ............. G06F 16/2379; G06F 16/2465; G06F 21/602; G06F 2216/03; G06F 16/9014; G06F 21/64
See application file for complete search history.

(56) References Cited

U.S. PATENT DOCUMENTS

| | | | |
|---|---|---|---|
| 5,862,218 A | 1/1999 | Steinberg | |
| 5,966,446 A | 10/1999 | Davis | |
| 7,028,263 B2 | 4/2006 | Maguire | |
| 7,272,179 B2 | 9/2007 | Siemens et al. | |
| 7,572,179 B2 | 8/2009 | Choi et al. | |
| 7,729,950 B2 | 6/2010 | Mendizabal et al. | |
| 8,245,038 B2 | 8/2012 | Golle et al. | |
| 8,266,439 B2 | 9/2012 | Haber et al. | |
| 8,442,903 B2 | 5/2013 | Zadoorian et al. | |
| 8,560,722 B2 | 10/2013 | Gates et al. | |
| 8,706,616 B1 | 4/2014 | Flynn | |
| 8,712,887 B2 | 4/2014 | DeGroeve et al. | |
| 8,867,741 B2 | 10/2014 | McCorkindale et al. | |
| 8,943,332 B2 | 1/2015 | Horne et al. | |
| 9,124,423 B2 | 9/2015 | Jennas, II et al. | |
| 9,378,343 B1 | 6/2016 | David | |
| 9,396,006 B2 | 7/2016 | Kundu et al. | |
| 9,407,431 B2 | 8/2016 | Bellare et al. | |
| 9,411,524 B2 | 8/2016 | O'Hare et al. | |
| 9,411,976 B2 | 8/2016 | Irvine | |
| 9,411,982 B1 | 8/2016 | Dippenaar et al. | |
| 9,424,576 B2 | 8/2016 | Vandervort | |
| 9,436,935 B2 | 9/2016 | Hudon | |
| 9,472,069 B2 | 10/2016 | Roskowski | |
| 9,489,827 B2 | 11/2016 | Quinn et al. | |
| 9,584,493 B1 | 2/2017 | Leavy | |
| 9,722,790 B2 | 8/2017 | Ebrahimi | |
| 9,876,646 B2 | 1/2018 | Ebrahimi | |
| 9,882,918 B1 | 1/2018 | Ford et al. | |
| 10,135,607 B1 | 11/2018 | Roets | |
| 10,163,080 B2 | 12/2018 | Chow | |
| 2003/0018563 A1 | 1/2003 | Kilgour et al. | |
| 2004/0085445 A1 | 5/2004 | Park | |
| 2005/0206741 A1 | 9/2005 | Raber | |
| 2006/0075228 A1 | 4/2006 | Black et al. | |
| 2006/0184443 A1 | 8/2006 | Erez et al. | |
| 2007/0094272 A1 | 4/2007 | Yeh | |
| 2007/0174630 A1 | 7/2007 | Shannon | |
| 2007/0296817 A1 | 12/2007 | Ebrahimi et al. | |
| 2008/0010466 A1 | 1/2008 | Hopper | |
| 2008/0028439 A1 | 1/2008 | Shevade | |
| 2008/0059726 A1 | 3/2008 | Rozas | |
| 2009/0025063 A1 | 1/2009 | Thomas | |
| 2009/0287597 A1 | 11/2009 | Bahar | |
| 2010/0049966 A1 | 2/2010 | Kato | |
| 2010/0058476 A1 | 3/2010 | Isoda | |
| 2010/0161459 A1 | 6/2010 | Kass et al. | |
| 2010/0228798 A1 | 9/2010 | Kodama | |
| 2010/0241537 A1 | 9/2010 | Kass et al. | |
| 2011/0061092 A1 | 3/2011 | Bailloeul | |
| 2011/0161674 A1 | 6/2011 | Ming | |
| 2012/0203670 A1 | 8/2012 | Piersol | |
| 2013/0142323 A1 | 6/2013 | Chiarella | |
| 2013/0222587 A1 | 8/2013 | Roskowski | |
| 2013/0276058 A1 | 10/2013 | Buldas | |
| 2014/0201541 A1 | 7/2014 | Paul | |
| 2014/0229738 A1 | 8/2014 | Sato | |
| 2014/0282852 A1 | 9/2014 | Vestevich | |
| 2014/0289802 A1 | 9/2014 | Lee | |
| 2014/0344015 A1 | 11/2014 | Puertolas-Montasnes et al. | |
| 2015/0193633 A1 | 7/2015 | Chida | |
| 2015/0206106 A1 | 7/2015 | Yago | |
| 2015/0244729 A1 | 8/2015 | Mao | |
| 2015/0378627 A1 | 12/2015 | Kitazawa | |
| 2015/0379484 A1 | 12/2015 | McCarthy | |
| 2016/0071096 A1 | 3/2016 | Rosca | |
| 2016/0098578 A1 | 4/2016 | Hincker | |
| 2016/0119134 A1 | 4/2016 | Hakoda et al. | |
| 2016/0148198 A1 | 5/2016 | Kelley | |
| 2016/0162897 A1 | 6/2016 | Feeney | |
| 2016/0217436 A1 | 7/2016 | Brama | |
| 2016/0239653 A1 | 8/2016 | Loughlin-Mchugh | |
| 2016/0253663 A1 | 9/2016 | Clark et al. | |
| 2016/0260091 A1 | 9/2016 | Tobias | |
| 2016/0267472 A1 | 9/2016 | Lingham et al. | |
| 2016/0267558 A1 | 9/2016 | Bonnell et al. | |
| 2016/0275294 A1 | 9/2016 | Irvine | |
| 2016/0283920 A1 | 9/2016 | Fisher et al. | |
| 2016/0292396 A1 | 10/2016 | Akerwall | |
| 2016/0292672 A1 | 10/2016 | Fay et al. | |
| 2016/0292680 A1 | 10/2016 | Wilson, Jr. et al. | |
| 2016/0294783 A1 | 10/2016 | Piqueras Jover | |
| 2016/0300200 A1 | 10/2016 | Brown et al. | |
| 2016/0300234 A1 | 10/2016 | Moss-Pultz et al. | |
| 2016/0321675 A1 | 11/2016 | McCoy et al. | |
| 2016/0321751 A1 | 11/2016 | Creighton, IV et al. | |
| 2016/0328791 A1 | 11/2016 | Parsells et al. | |
| 2016/0330031 A1 | 11/2016 | Drego et al. | |
| 2016/0330244 A1 | 11/2016 | Denton | |
| 2016/0337119 A1 | 11/2016 | Hosaka et al. | |
| 2016/0342977 A1 | 11/2016 | Lam | |
| 2016/0342989 A1 | 11/2016 | Davis | |
| 2016/0344737 A1 | 11/2016 | Anton et al. | |
| 2016/0371771 A1 | 12/2016 | Serrano | |
| 2017/0005797 A1 | 1/2017 | Lanc et al. | |
| 2017/0033933 A1 | 2/2017 | Haber | |
| 2017/0053249 A1 | 2/2017 | Tunnell et al. | |
| 2017/0061396 A1 | 3/2017 | Melika et al. | |
| 2017/0075938 A1 | 3/2017 | Black | |
| 2017/0124534 A1 | 5/2017 | Savolainen | |
| 2017/0124535 A1 | 5/2017 | Juels et al. | |
| 2017/0161439 A1 | 6/2017 | Raduchel | |
| 2017/0177898 A1 | 6/2017 | Dillenberger | |
| 2017/0178237 A1 | 6/2017 | Wong | |
| 2017/0213287 A1 | 7/2017 | Bruno | |
| 2017/0221052 A1 | 8/2017 | Sheng | |
| 2017/0243208 A1 | 8/2017 | Kurian et al. | |
| 2017/0243289 A1 | 8/2017 | Rufo | |
| 2017/0244757 A1 | 8/2017 | Castinado et al. | |
| 2017/0330279 A1 | 11/2017 | Ponzone | |
| 2017/0352031 A1 | 12/2017 | Collin | |
| 2017/0373859 A1 | 12/2017 | Shors et al. | |
| 2018/0075239 A1 | 3/2018 | Boutnaru | |
| 2018/0075527 A1 | 3/2018 | Nagla et al. | |
| 2018/0091524 A1 | 3/2018 | Setty | |
| 2018/0097779 A1 | 4/2018 | Karame et al. | |
| 2018/0101701 A1 | 4/2018 | Barinov | |
| 2018/0139042 A1 | 5/2018 | Binning | |
| 2018/0157700 A1 | 6/2018 | Roberts | |
| 2018/0167201 A1 | 6/2018 | Naqvi | |
| 2018/0173906 A1 | 6/2018 | Rodriguez | |
| 2018/0176017 A1 | 6/2018 | Rodriguez | |
| 2018/0181768 A1 | 6/2018 | Leporini | |
| 2018/0182042 A1 | 6/2018 | Vinay | |
| 2018/0189333 A1 | 7/2018 | Childress | |
| 2018/0189781 A1 | 7/2018 | McCann | |
| 2018/0204213 A1 | 7/2018 | Zappier | |
| 2018/0219683 A1 | 8/2018 | Deery | |
| 2018/0219685 A1 | 8/2018 | Deery | |
| 2018/0225640 A1 | 8/2018 | Chapman | |

(56) References Cited

U.S. PATENT DOCUMENTS

| | | |
|---|---|---|
| 2018/0241565 A1 | 8/2018 | Paolini-Subramanya |
| 2018/0260888 A1 | 9/2018 | Paolini-Subramanya |
| 2018/0260889 A1 | 9/2018 | Paolini-Subramanya |
| 2018/0268162 A1 | 9/2018 | Dillenberger |
| 2018/0268382 A1 | 9/2018 | Wasserman |
| 2018/0268504 A1 | 9/2018 | Paolini-Subramanya |
| 2018/0276668 A1 | 9/2018 | Li |
| 2018/0276745 A1 | 9/2018 | Paolini-Subramanya |
| 2018/0285970 A1 | 10/2018 | Snow |
| 2018/0285971 A1 | 10/2018 | Rosenoer |
| 2018/0316502 A1 | 11/2018 | Nadeau |
| 2018/0367298 A1 | 12/2018 | Wright |
| 2019/0018947 A1 | 1/2019 | Li |
| 2019/0036887 A1 | 1/2019 | Miller |
| 2019/0043048 A1 | 2/2019 | Wright |
| 2019/0044727 A1 | 2/2019 | Scott |
| 2019/0087446 A1 | 3/2019 | Sharma |
| 2019/0123889 A1 | 4/2019 | Schmidt-Karaca |
| 2019/0197532 A1 | 6/2019 | Jayachandran |
| 2019/0205563 A1 | 7/2019 | Gonzales, Jr. |
| 2019/0251557 A1 | 8/2019 | Jin |
| 2019/0253258 A1 | 8/2019 | Thekadath |
| 2019/0268141 A1 | 8/2019 | Pandurangan |
| 2019/0268163 A1 | 8/2019 | Nadeau |
| 2019/0281259 A1 | 9/2019 | Palazzolo |
| 2019/0287107 A1 | 9/2019 | Gaur |
| 2019/0288832 A1 | 9/2019 | Dang |
| 2019/0324867 A1 | 10/2019 | Tang |
| 2019/0334715 A1 | 10/2019 | Gray |
| 2019/0342422 A1 | 11/2019 | Li |
| 2019/0347444 A1 | 11/2019 | Lowagie |
| 2019/0354606 A1 | 11/2019 | Snow |
| 2019/0354607 A1 | 11/2019 | Snow |
| 2019/0354611 A1 | 11/2019 | Snow |
| 2019/0354724 A1 | 11/2019 | Lowagie |
| 2019/0354725 A1 | 11/2019 | Lowagie |
| 2019/0354964 A1 | 11/2019 | Snow |
| 2019/0356733 A1 | 11/2019 | Snow |
| 2019/0391540 A1 | 12/2019 | Westervelt' |
| 2019/0394044 A1 | 12/2019 | Snow |
| 2019/0394048 A1 | 12/2019 | Deery |
| 2020/0004946 A1 | 1/2020 | Gilpin |
| 2020/0034813 A1 | 1/2020 | Calinog |
| 2020/0042635 A1 | 2/2020 | Douglass |
| 2020/0042960 A1 | 2/2020 | Cook |
| 2020/0042982 A1 | 2/2020 | Snow |
| 2020/0042983 A1 | 2/2020 | Snow |
| 2020/0042984 A1 | 2/2020 | Snow |
| 2020/0042985 A1 | 2/2020 | Snow |
| 2020/0042986 A1 | 2/2020 | Snow |
| 2020/0042987 A1 | 2/2020 | Snow |
| 2020/0042988 A1 | 2/2020 | Snow |
| 2020/0042990 A1 | 2/2020 | Snow |
| 2020/0042995 A1 | 2/2020 | Snow et al. |
| 2020/0044827 A1 | 2/2020 | Snow |
| 2020/0044856 A1 | 2/2020 | Lynde |
| 2020/0044857 A1 | 2/2020 | Snow |
| 2020/0065761 A1 | 2/2020 | Tatchell |
| 2020/0089690 A1 | 3/2020 | Qiu |
| 2020/0099534 A1 | 3/2020 | Lowagie |
| 2020/0104712 A1 | 4/2020 | Katz |
| 2020/0145219 A1 | 5/2020 | Sebastian |
| 2020/0167870 A1 | 5/2020 | Isaacson |
| 2020/0175506 A1 | 6/2020 | Snow |
| 2020/0279324 A1 | 9/2020 | Snow |
| 2020/0279325 A1 | 9/2020 | Snow |
| 2020/0279326 A1 | 9/2020 | Snow |
| 2020/0280447 A1 | 9/2020 | Snow |

FOREIGN PATENT DOCUMENTS

| | | |
|---|---|---|
| JP | 5383297 | 1/2014 |
| KR | 100653512 | 11/2006 |
| KR | 101747221 | 6/2017 |
| WO | WO 0049797 | 8/2000 |
| WO | WO 2007069176 | 6/2007 |
| WO | WO 2015077378 | 5/2015 |
| WO | WO 2018013898 A1 | 1/2018 |
| WO | WO 2018109010 | 6/2018 |

OTHER PUBLICATIONS

Crosby, Michael et al., "BlockChain Technology, Beyond Bitcoin", Sutardja Center for Entrepreneurship & Technology, Berkeley Engineering, Oct. 16, 2015, 35 pages.

Alsolami, Fahad, and Terrance E. Boult. "CloudStash: using secret-sharing scheme to secure data, not keys, in multi-clouds." *Information Technology: New Generations (ITNG), 2014 11th International Conference on*. IEEE, 2014.

Unknown, "Midex", https://promo.midex.com/Midex_EN.pdf, 25 pages.

Unknown, Xtrade White Paper, https://xtrade1-9649.kxcdn.com/wp-content/uploads/2017/09/xtrade-whitepaper.pdf Feb. 7, 2018, 37 pages.

Haarmann, et al., "DMN Decision Execution on the Ethereum Blockchain," Hasso Plattner Institute, University of Potsdam, 15 pages.

Kim et al., "A Perspective on Blockchain Smart Contracts," Schulich School of Business, York University, Toronto, Canada, 6 pages.

Chakravorty, Antorweep, and Chunming Rong, "Ushare: user controlled social media based on blockchain." *Proceedings of the 11th International Conference on Ubiquitous Information Management and Communication*. ACM, 2017.

Chen, Zhixong, and Yixuan Zhu. "Personal Archive Service System using Blockchain Technology: Case Study, Promising and Challenging." AI & Mobile Services (AIMS), 2017 IEEE International Conference on. IEEE, 2017.

Al-Naji, Nader et al., "Basis: A Price-Stable Cryptocurrency with an Algorithmic Central Bank" www.basis.io Jun. 20, 2017, 27 pages.

Unkown, "Federated Learning: Collaborative Machine Learning without Centralized Training Data" Apr. 6, 2017, 11 pages.

Casey, "BitBeat: Factom Touts Blockchain Tool for Keeping Record Keepers Honest", Wall Street Journal, Nov. 5, 2014.

Menezes, Alfred. J., et al. "Handbook of Applied Cryptography," 1997, CRC Press, p. 527-28.

White, Ron, "How Computers Work," Oct. 2003, QUE, Seventh Edition (Year: 2003), 23 pages.

Luu et al., Making Smart Contracts Smarter, 2016.

RAM HASHING IN BLOCKCHAIN ENVIRONMENTS

CROSS-REFERENCE TO RELATED APPLICATIONS

This patent application claims domestic benefit of U.S. Provisional Application No. 63/061,372 filed Aug. 5, 2020 and is incorporated herein by reference in its entirety. This patent application claims domestic benefit of U.S. Provisional Application No. 62/962,486 filed Jan. 17, 2020 and is incorporated herein by reference in its entirety. This patent application also claims domestic benefit of U.S. Provisional Application No. 62/963,217 filed Jan. 20, 2020 and is incorporated herein by reference in its entirety.

BACKGROUND

Today's blockchain processing consumes great hardware, network, and energy resources. When Satoshi first proposed a cryptographic blockchain, so-called "miners" expended CPU time and electricity to mine blockchain data. The mining of blockchains was democratic, meaning anyone with a conventional CPU-based computer could process the complicated calculations required to embed a block of data on a blockchain. Soon, though, the miners realized that a graphics processing unit (or GPU) was much faster than a CPU and could be optimized to solve the complicated calculations. Soon thereafter, most or all blockchain mining was performed by a specially programmed GPU computer, as a conventional CPU-based computer was comparatively too slow. Today, though, the miners use a specially-designed application-specific integrated circuit (or ASIC), as ASICs are even faster than GPUs. These ASIC computers are much faster at solving the complicated calculations, but the ASIC computers are very expensive and consume large amounts of electrical power. The ASIC computers are so cost prohibitive that, today, blockchain mining is largely undemocratic. Only a relatively small number of miners have access to the financial capital and to energy sources to mine blockchains.

SUMMARY

Exemplary embodiments encourage blockchain miners to use CPU-based computer machines. Exemplary embodiments discourage or deter the use of specialized hardware (such as GPUs and ASICs) in blockchain mining by utilizing memory size restrictions and cache latency of cache memory. Exemplary embodiments may further promote democratic mining by separating hashing operations from difficulty and proof-of-work operations. When blockchain transactions or other data is processed or mined, encryption (such as a hashing algorithm) may be a stand-alone software application or programming code. Blockchain miners may also use a separate difficulty scheme and a separate proof-of-work scheme. The encryption/hashing algorithm, a difficulty algorithm, and a proof-of-work algorithm may thus be separately called or executed. A blockchain may thus use any encryption algorithm, any difficulty algorithm, and/or any proof-of-work algorithm. Blockchain environments may thus mix-and-match different encryption, difficulty, and/or proof-of-work schemes when mining blockchain data. Each encryption, difficulty, and/or proof-of-work scheme may be separate, stand-alone programs, files, or third-party services. Blockchain miners may be agnostic to a particular blockchain's encryption, difficulty, and/or proof-of-work schemes, thus allowing any blockchain miner to process or mine data in multiple blockchains. GPUs, ASICs, and other specialized processing hardware components may be deterred by forcing cache misses, cache latencies, and processor stalls. Hashing, difficulty, and/or proof-of-work schemes require less programming code, consume less storage space/usage in bytes, and execute faster. Blockchain mining schemes may further randomize byte or memory block access, further improve cryptographic security.

BRIEF DESCRIPTION OF THE SEVERAL VIEWS OF THE DRAWINGS

The features, aspects, and advantages of the exemplary embodiments are understood when the following Detailed Description is read with reference to the accompanying drawings, wherein.

DETAILED DESCRIPTION

Figure 1:
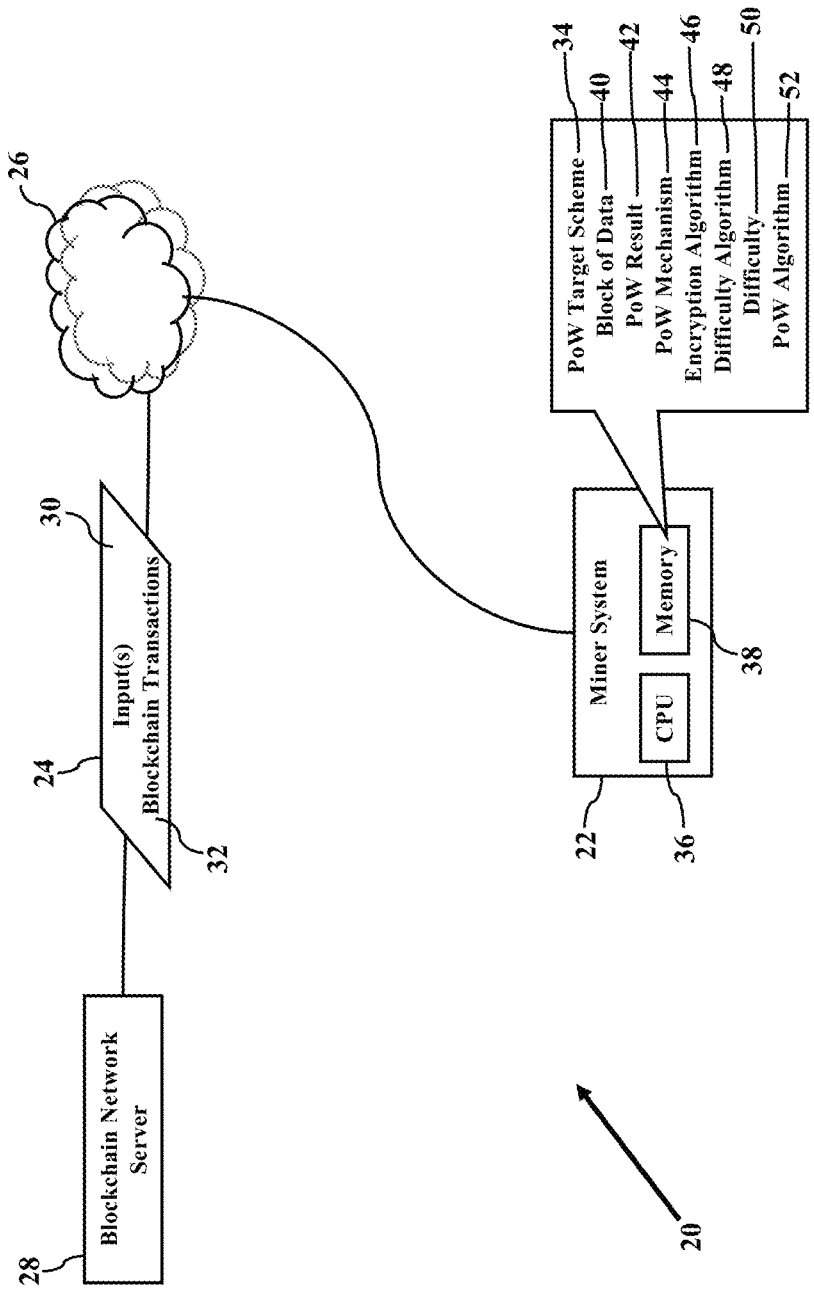
FIGS. 1-19 are simplified illustrations of a blockchain environment, according to exemplary embodiments.

The exemplary embodiments will now be described more fully hereinafter with reference to the accompanying drawings. The exemplary embodiments may, however, be embodied in many different forms and should not be construed as limited to the embodiments set forth herein. These embodiments are provided so that this disclosure will be thorough and complete and will fully convey the exemplary embodiments to those of ordinary skill in the art. Moreover, all statements herein reciting embodiments, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure).

Thus, for example, it will be appreciated by those of ordinary skill in the art that the diagrams, schematics, illustrations, and the like represent conceptual views or processes illustrating the exemplary embodiments. The functions of the various elements shown in the figures may be provided through the use of dedicated hardware as well as hardware capable of executing associated software. Those of ordinary skill in the art further understand that the exemplary hardware, software, processes, methods, and/or operating systems described herein are for illustrative purposes and, thus, are not intended to be limited to any particular named manufacturer.

As used herein, the singular forms "a," "an," and "the" are intended to include the plural forms as well, unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

It will also be understood that, although the terms first, second, etc. may be used herein to describe various elements, these elements should not be limited by these terms. These terms are only used to distinguish one element from another. For example, a first device could be termed a second device, and, similarly, a second device could be termed a first device without departing from the teachings of the disclosure.

FIGS. 1-19 are simplified illustrations of a blockchain environment 20, according to exemplary embodiments. A miner system 22 receives one or more inputs 24 via a communications network 26 from a blockchain network server 28. While the inputs 24 may be any electronic data 30, in the blockchain environment 20, the inputs 24 are blockchain transactions 32 (such as financial transactions, inventory/shipping data, and/or healthcare medical data). The actual form or content represented by the electronic data 30 and the blockchain transactions 32 may be unimportant. The blockchain network server 28 sends, distributes, or broadcasts the inputs 24 to some or all of the authorized mining participants (such as the miner system 22). The blockchain network server 28 may also specify a proof-of-work ("PoW") target scheme 34, which may accompany the inputs 24 or be separately sent from the inputs 24.

The miner system 22 may mine the inputs 24. When the miner system 22 receives the inputs 24, the miner system 22 has a hardware processor (such as CPU 36) and a solid-state memory device 38 that collects the inputs 24 (such as the blockchain transactions 32) into a block 40 of data. The miner system 22 then finds a difficult proof-of-work ("PoW") result 42 based on the block 40 of data. The miner system 22 performs, executes, or calls/requests a proof-of-work ("PoW") mechanism 44. The proof-of-work mechanism 44 is a computer program, instruction(s), or code that instruct or cause the miner system 22 to call, request, and/or execute an encryption algorithm 46. The proof-of-work mechanism 44 may instruct or cause the miner system 22 to call, request, and/or execute a difficulty algorithm 48 that generates or creates a difficulty 50. The proof-of-work mechanism 44 may also instruct or cause the miner system 22 to call, request, and/or execute a proof-of-work ("PoW") algorithm 52. The proof-of-work mechanism 44 may thus be one or more software applications or programming schemes that separate the encryption algorithm 46 from the difficulty algorithm 48 and/or from the proof-of-work algorithm 52. Because the encryption algorithm 46 may be separately executed/called from the difficulty algorithm 48 and/or from the proof-of-work algorithm 52, encryption of the electronic data 30 (representing the inputs 24) is separately performed from the difficulty 50 of solving the proof-of-work. In other words, any encryption algorithm 46 may be used, along with any difficulty algorithm 48, and/or along with any proof-of-work algorithm 52.

Figure 2:
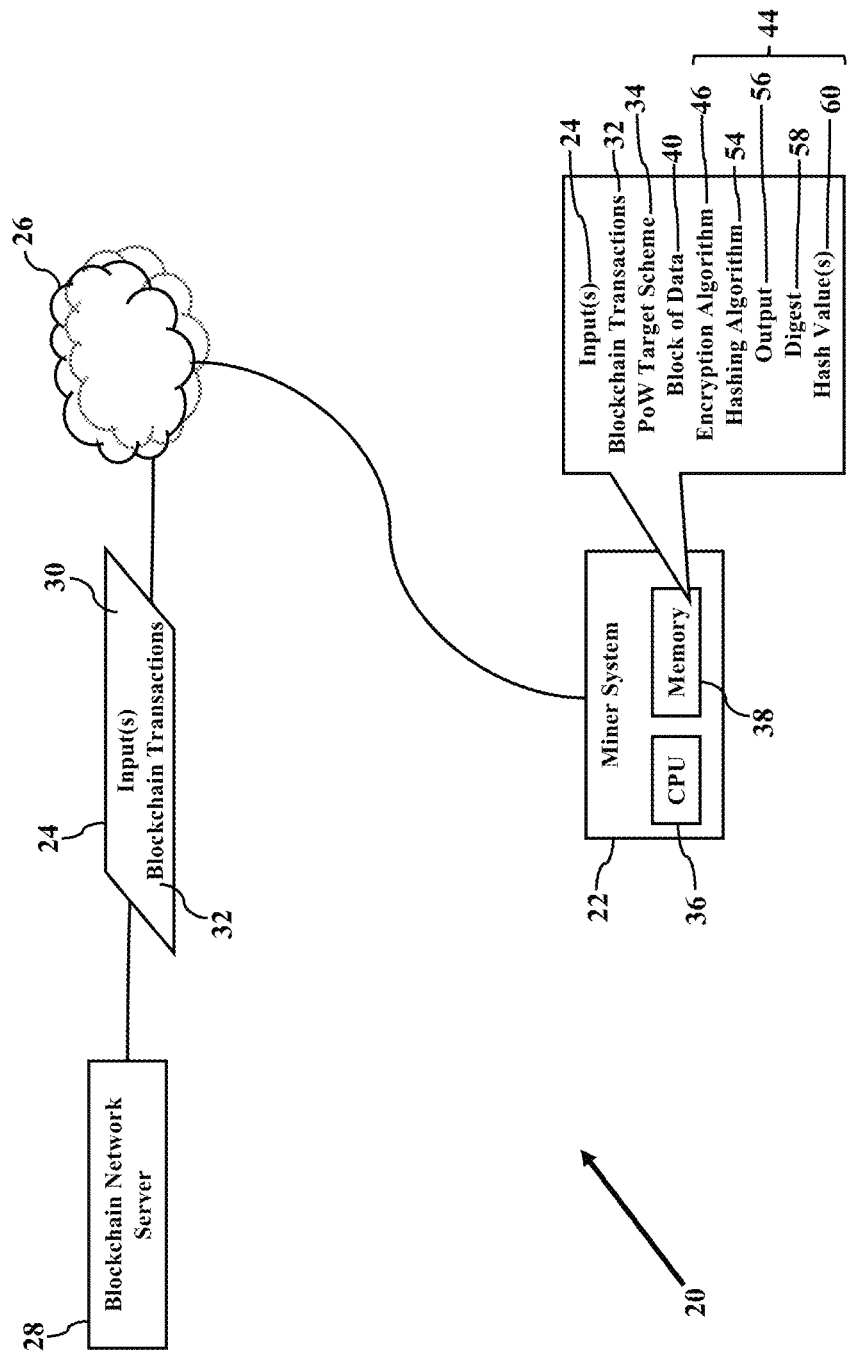

FIG. 2 further illustrates the proof-of-work mechanism 44. While the encryption algorithm 46 may utilize any encryption scheme, process, and/or function, many readers may be familiar with a cryptographic hashing algorithm 54 (such as the SHA-256 used by BITCOIN®). The cryptographic hashing algorithm 54 may thus generate an output 56 (sometimes called a digest 58) by implementing or executing the cryptographic hashing algorithm 54 using the inputs 24 (such as the blockchain transactions 32). So, whatever the arbitrary bit values of the inputs 24, and whatever the arbitrary bit length of the inputs 24, the cryptographic hashing algorithm 54 may generate the output 56 as one or more hash values 60, perhaps having a fixed length (or n-bit). The miner system 22 may thus receive the inputs 24 from the blockchain network server 28, call and/or execute the encryption algorithm 46 (such as the cryptographic hashing algorithm 54), and generate the hash value(s) 60.

Figure 3:
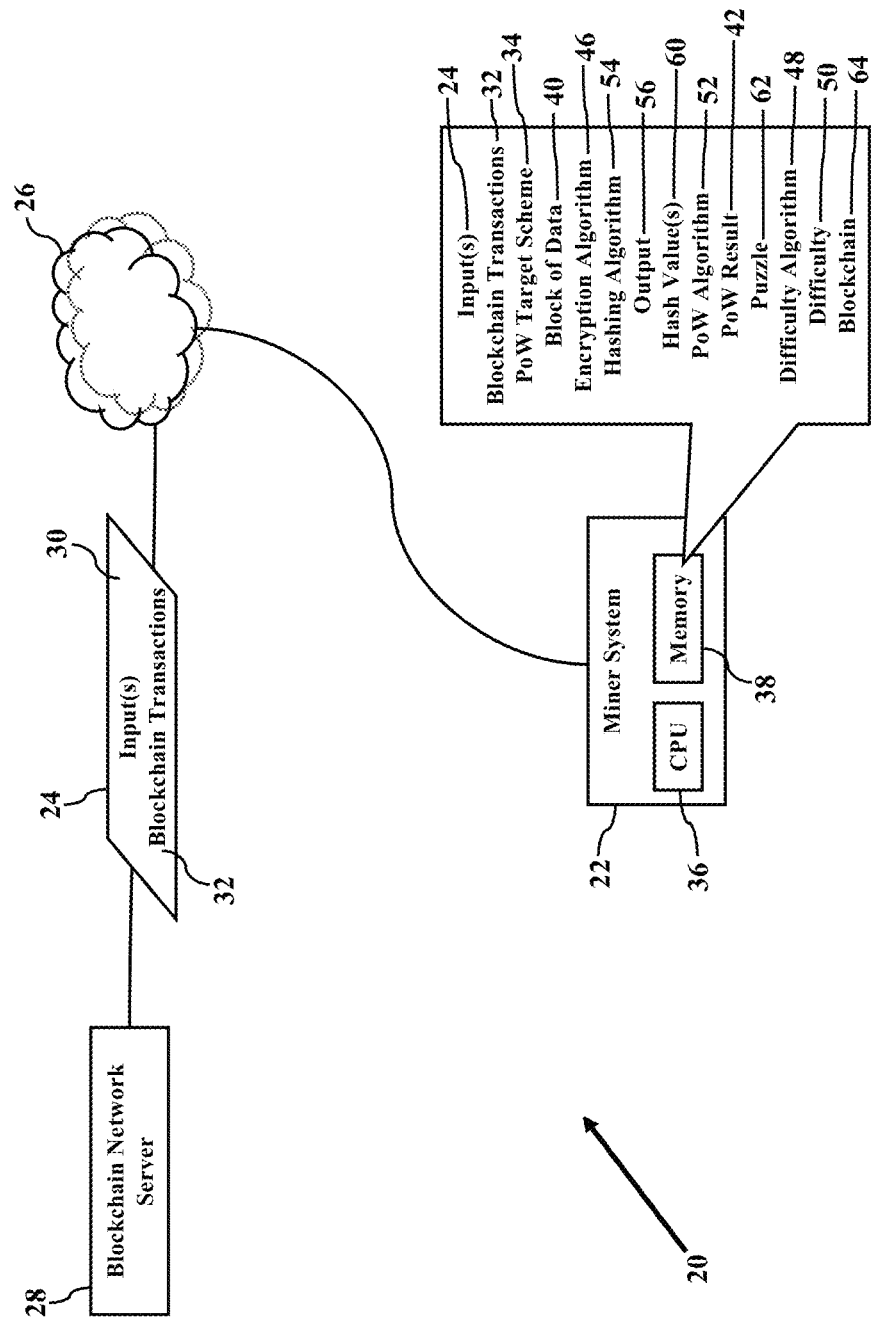

As FIG. 3 illustrates, the miner system 22 may separately perform or call the proof-of-work algorithm 52. After the encryption algorithm 46 creates the output(s) 56, the miner system 22 may read/retrieve the output(s) 56 and send the output(s) 56 to the proof-of-work algorithm 52. The miner system 22 may thus generate the proof-of-work result 42 by calling and/or by executing the proof-of-work algorithm 52 using the output(s) 56. The miner system 22, for example, may send the hash value(s) 60 (generated by the cryptographic hashing algorithm 54) to the proof-of-work algorithm 52, and the proof-of-work algorithm 52 generates the proof-of-work result 42 using the hash value(s) 60. The proof-of-work algorithm 52 may also compare the proof-of-work result 42 to the proof-of-work ("PoW") target scheme 34. The proof-of-work algorithm 52 may, in general, have to satisfy or solve a mathematical puzzle 62, perhaps defined or specified by the proof-of-work target scheme 34. The proof-of-work target scheme 34 may also specify, or relate to, the difficulty 50 of solving the mathematical puzzle 62. That is, the more stringent or precise the proof-of-work target scheme 34 (e.g., a minimum/maximum value of the hash value 60), the more difficult the mathematical puzzle 62 is to solve. In other words, the difficulty 50 is a measure of how difficult it is to mine the block 40 of data, given the solution requirements of the proof-of-work target scheme 34.

The miner system 22 may own the block 40 of data. If the miner system 22 is the first to satisfy the proof-of-work target scheme 34 (e.g., the proof-of-work result 42 satisfies the mathematical puzzle 62), the miner system 22 may timestamp the block 40 of data and broadcast the block 40 of data, the timestamp, the proof-of-work result 42, and/or the mathematical puzzle 62 to other miners in the blockchain environment 20. The miner system 22, for example, may broadcast a hash value representing the block 40 of data, and the other miners begin working on a next block in the blockchain 64.

Today's BITCOIN® difficulty is increasing. On or about Jun. 16, 2020, BITCOIN's network adjusted its difficulty level (the measure of how hard it is for miners to compete for block rewards on the blockchain) to 15.78 trillion, which was nearly a 15% increase in the difficulty 50. As the difficulty 50 increases, older, less capable, and less power efficient miners are unable to compete. As a result, today's BITCOIN® miners must have the latest, fastest hardware (such as an ASIC) to profitably solve the mathematical puzzle 62 according to the proof-of-work target scheme 34. Indeed, Satoshi envisioned that increasing hardware speed would allow miners to easier solve the proof-of-work. Satoshi thus explained that the difficulty would be a moving target to slow down generation of the blocks 40 of data.

Conventional mining schemes are integrated. When a conventional blockchain miner attempts to solve the mathematical puzzle 62, the conventional blockchain miner executes a conventional scheme that integrates hashing, difficulty, and proof-of-work. That is, conventional proof-of-work schemes require the miners to execute a combined software offering or pre-set combination of encryption and proof. These conventional proof-of-work scheme, in other words, integrate a predetermined encryption/hashing algorithm into or with a predetermined difficulty and a predetermined proof-of-work algorithm. These conventional proof-of-work schemes thus force the miners to execute a predetermined or predefined scheme that functionally marries or bundles encryption, difficulty, and proof-of-work.

The conventional schemes specify a difficulty mechanism. BITCOIN's difficulty mechanism, for example, is a measure of how difficult it is to mine a BITCOIN® block of data. BITCOIN® miners are required to find a hash value below a given target (e.g., SHA256(nonce+input) has n leading zeros, where n determines the mining difficulty). The difficulty adjustment is directly related to the total estimated mining power (sometimes estimated in Total Hash Rate per second). BITCOIN's difficulty mechanism is adjusted to basically ensure that ten (10) minutes of computation are required before a miner may solve the mathematical puzzle 62.

The conventional schemes force the use of specialized hardware. When blockchain mining first appeared, home/desktop computers and laptops (and their conventional processors or CPUs) were adequate. However, as blockchain mining became more difficult and competitive, miners gained an advantage by repurposing a dedicated graphics processing unit (or GPU) for blockchain mining. As an example, the RADEON® HD 5970 GPU has a clocked processing speed of executing about 3,200 of 32-bit instructions per clock, which is about 800 times more than the speed of a CPU that executes only four (4) 32-bit instructions per clock. This increased processor clock speed allowed GPUs to perform far more calculations and made GPUs more desirable for cryptocurrency/blockchain mining. Later, field programmable gate arrays (FPGAs) were also re-modeled for cryptocurrency/blockchain mining. FPGAs were able to compute the mathematical operations required to mine the block 40 of data twice as fast as the GPU. However, FPGA devices were more labor-intensive to build and still require customized configurations (both software programming and hardware). Today's BITCOIN® miners have pushed the hardware requirements even further by using a specialized application-specific integrated circuit (ASIC) that is exclusively designed for blockchain mining. These ASICs may be 100 billion times faster than mere CPUs. These ASICs have made BITCOIN® mining undemocratic and only possible by a relatively few, well capitalized entities running mining farms. Today's BITCOIN® miners thus consume great quantities of electrical power and pose concerns for the electrical grid.

Today's conventional mining hardware has further specialized. Some ASICs have also been further designed for particular blockchains to achieve additional optimizations. For example, a hardware implementation of the SHA-256 hash is much faster than a version coded in software. Today, nearly all BITCOIN® mining is performed using hardware ASICs. Specialized hardware has even been developed for particular hashing functions. The RAVENCOIN® scheme, as an example, uses several different hashing algorithms, and a particular hashing algorithm is picked for one block based off of a hash of a previous block (the RAVENCOIN® scheme resembles a random selection of the hashing algorithm). However, because fifteen (15) of the sixteen (16) algorithms sit on the sidelines unused at any given time, the RAVENCOIN® scheme makes it very expensive for a miner to buy sixteen (16) different hardware rigs in order to mine according to the RAVENCOIN® scheme. Even if a miner decides to only mine the blocks that match a particular hardware requirement, the hardware still sits idle 14-15 cycles on average.

Some blockchains may also alter or modify the mining scheme. For example, the MONERO® mining scheme uses a specialized hashing function that implements a random change. That is, the MONERO® mining scheme uses a hash algorithm that unpredictably rewrites itself. The MONERO® mining network introduced a RandomX mining algorithm that was designed to deter ASICs and to improve the efficiency of conventional CPUs. MONERO's RandomX mining algorithm uses random code execution and memory-intensive techniques, rendering ASICs too expensive and ineffective to develop.

The conventional mining schemes thus have many disadvantages. Conventional mining schemes have become so specialized and so expensive that only a small number of large miners have the resources to compete. Blockchain mining, in other words, has become centralized and undemocratic. Some conventional schemes try to find new hashing algorithms, new proof-of-work schemes, or modify existing schemes to de-centralize and to democratize mining participants. Some conventional mining schemes (such as ETHERIUIM®) require very large memory spaces in bytes, which disadvantages its hardware. LITECOIN® also disadvantages hardware by copying large byte amounts of data.

Figure 4:
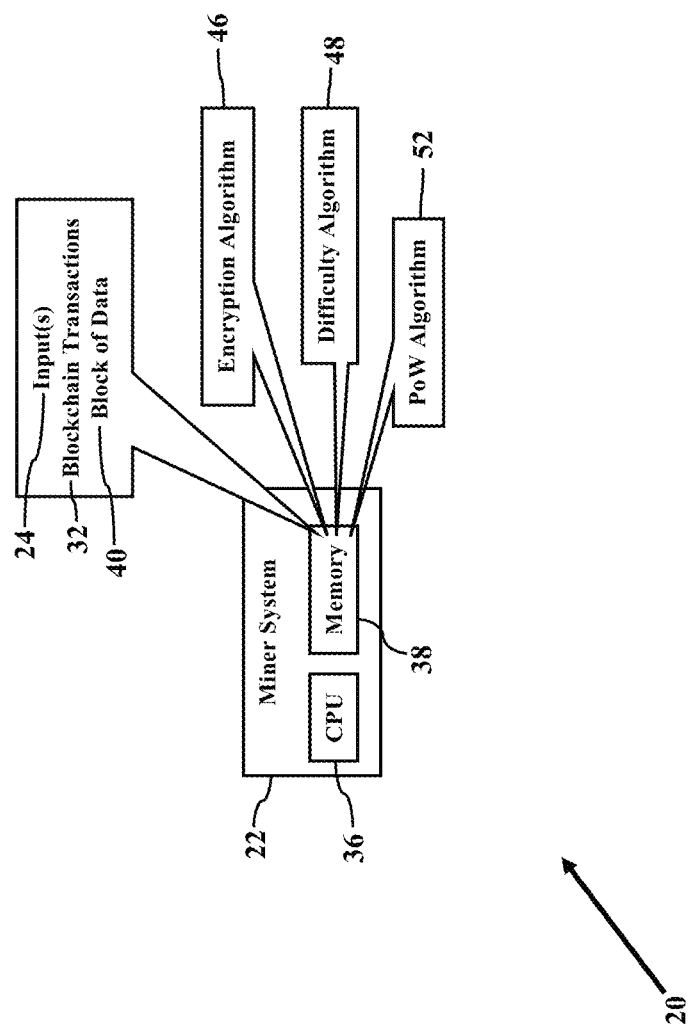
Figure 5:
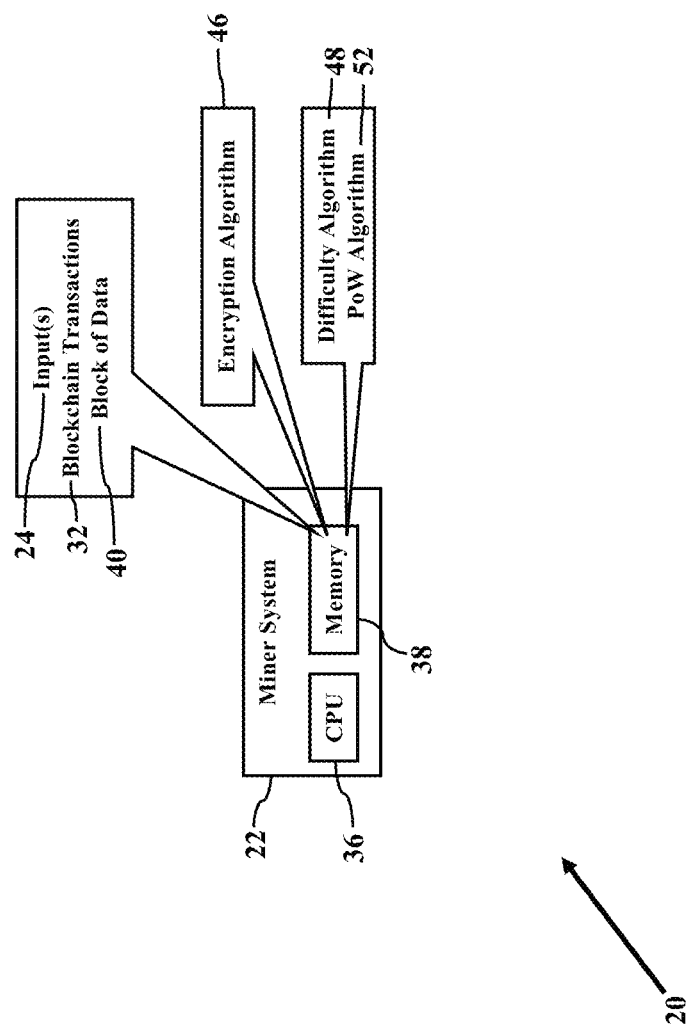
Figure 6:
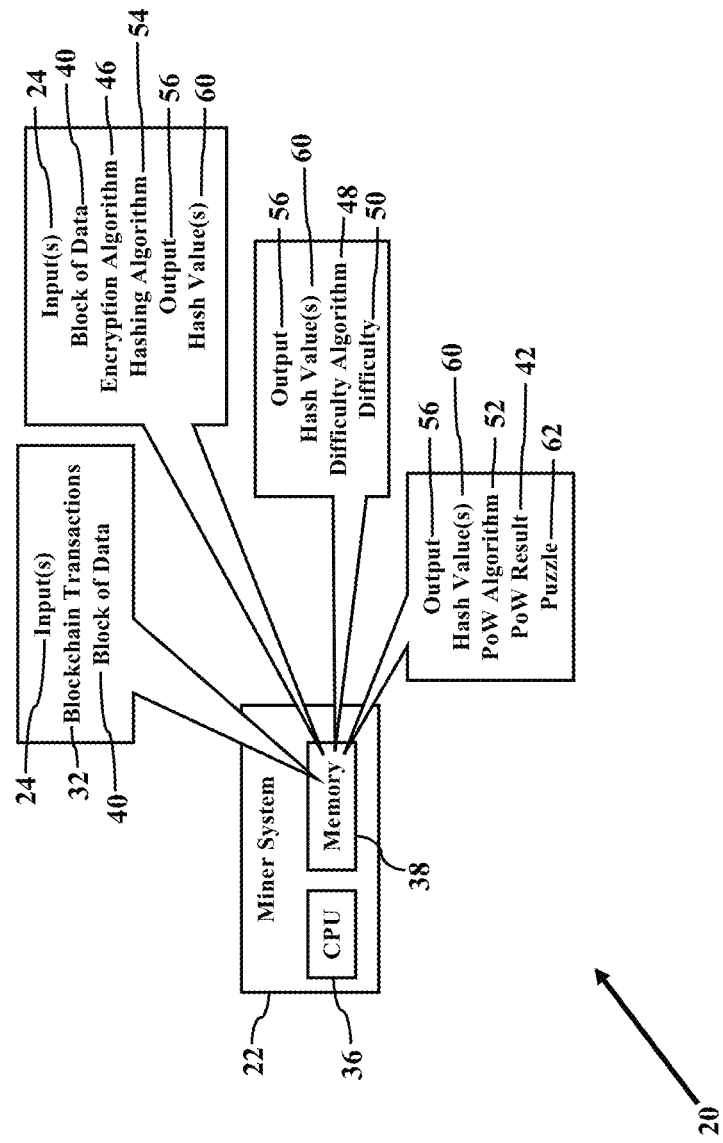

As FIGS. 4-6 illustrate, though, exemplary embodiments may mix-and-match the encryption algorithm 46, the difficulty algorithm 48, and the proof-of-work algorithm 52. The inventor has observed that there is no mining law or scheme that requires a preset or predefined difficulty scheme (such as BITCOIN'S counting zeroes on the hash to decide its difficulty). Instead, exemplary embodiments may use any encryption algorithm 46 that a cryptographic coin, network, or scheme desires or specifies. Exemplary embodiments may use any difficulty algorithm 48 that the cryptographic coin, network, or scheme desires or specifies. Exemplary embodiments may use any proof-of-work algorithm 52 that the cryptographic coin, network, or scheme desires or specifies. FIG. 4 illustrates the encryption algorithm 46, the difficulty algorithm 48, and proof-of-work algorithm 52 as separate software mechanisms. FIG. 5 illustrates alternative software mechanism where the difficulty algorithm 48 and proof-of-work algorithm 52 may be functionally intertwined, but the encryption algorithm 46 is a separate, stand-alone program, file, or service. FIG. 6 illustrates the inputs and outputs for the encryption algorithm 46, the difficulty algorithm 48, and proof-of-work algorithm 52.

Figure 7:
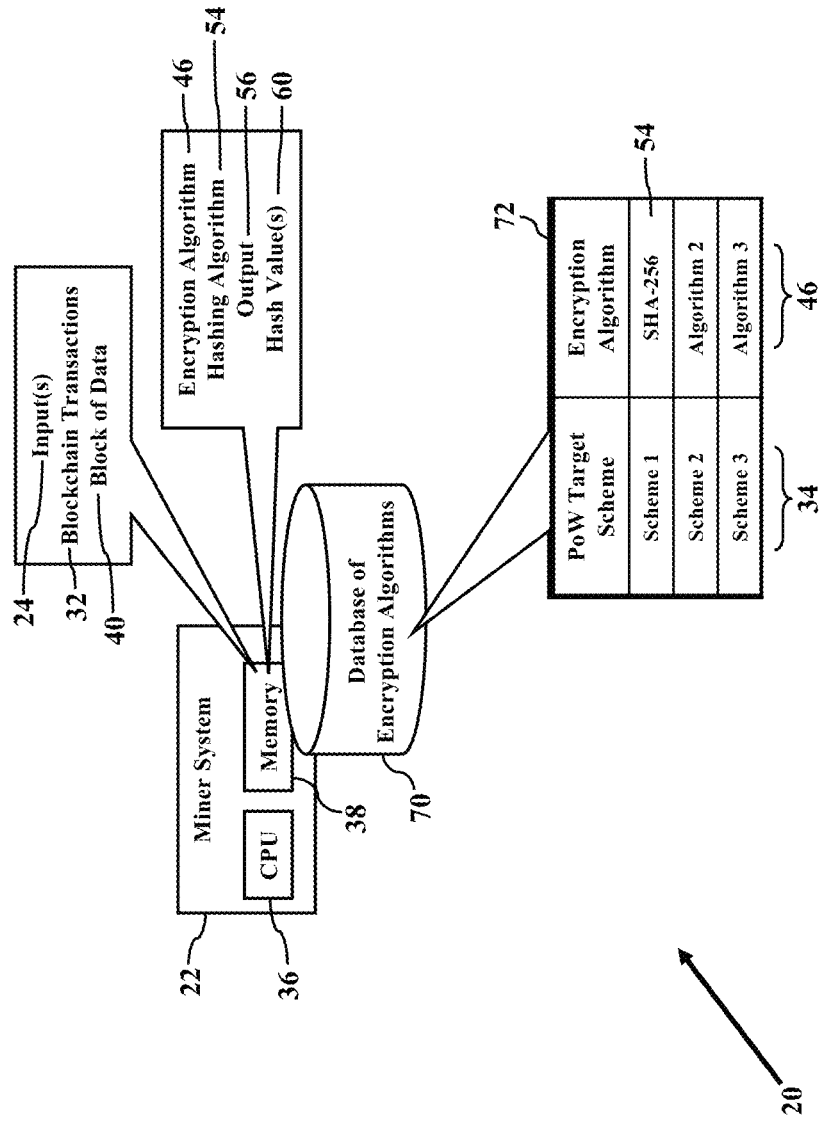

FIG. 7 illustrates agnostic hashing. Exemplary embodiments may use any encryption algorithm 46 that a cryptographic coin, blockchain network, or scheme desires or specifies. Because most blockchain mining schemes use hashing, FIG. 7 illustrates the cryptographic hashing algorithm 54. The proof-of-work ("PoW") target scheme 34 may thus use any cryptographic hashing algorithm 54, as exemplary embodiments are agnostic to hashing/encryption. The encryption algorithm 46 may be any cryptographic hashing algorithm 54 (e.g., the SHA-2 family (SHA-256 and SHA-512) and/or the SHA-3 family). The miner system 22 need only request, call, and/or execute the particular cryptographic hashing algorithm 54 specified by the proof-of-work target scheme 34. FIG. 7 thus illustrates an electronic database 70 of encryption algorithms accessible to the miner system 22. While the database 70 of encryption algorithms is illustrated as being locally stored in the memory device 38 of the miner system 22, the database 70 of encryption algorithms may be remotely stored and accessed/queried at any networked location. Even though the database 70 of encryption algorithms may have any logical structure, a relational database is perhaps easiest to understand. FIG. 7 thus illustrates the database 70 of encryption algorithms as an electronic table 72 that maps, converts, or translates different proof-of-work target schemes 34 to their corresponding or associated encryption algorithm 46 (such as the particular cryptographic hashing algorithm 54). The miner system 22 may thus identify the encryption algorithm 46 by querying the electronic database 70 of encryption algorithms for the proof-of-work target scheme 34 specified for use by the blockchain environment 20. So, once the particular cryptographic hashing algorithm 54 is identified, the miner system 22 may acquire or retrieve any inputs 24 (such as the blockchain transactions 32) and execute the cryptographic hashing algorithm 54 specified by the proof-of-work target scheme 34. The miner system 22 may optionally send the inputs 24 via the Internet or other network (e.g., the communications network 26 illustrated in FIGS. 1-3) to a remote destination for service execution (as later paragraphs will explain). The encryption algorithm 46 (e.g., the cryptographic hashing algorithm 54 specified by the proof-of-work target scheme 34) may thus generate the output 56/digest 58 represented as the hash value(s) 60.

Figure 8:
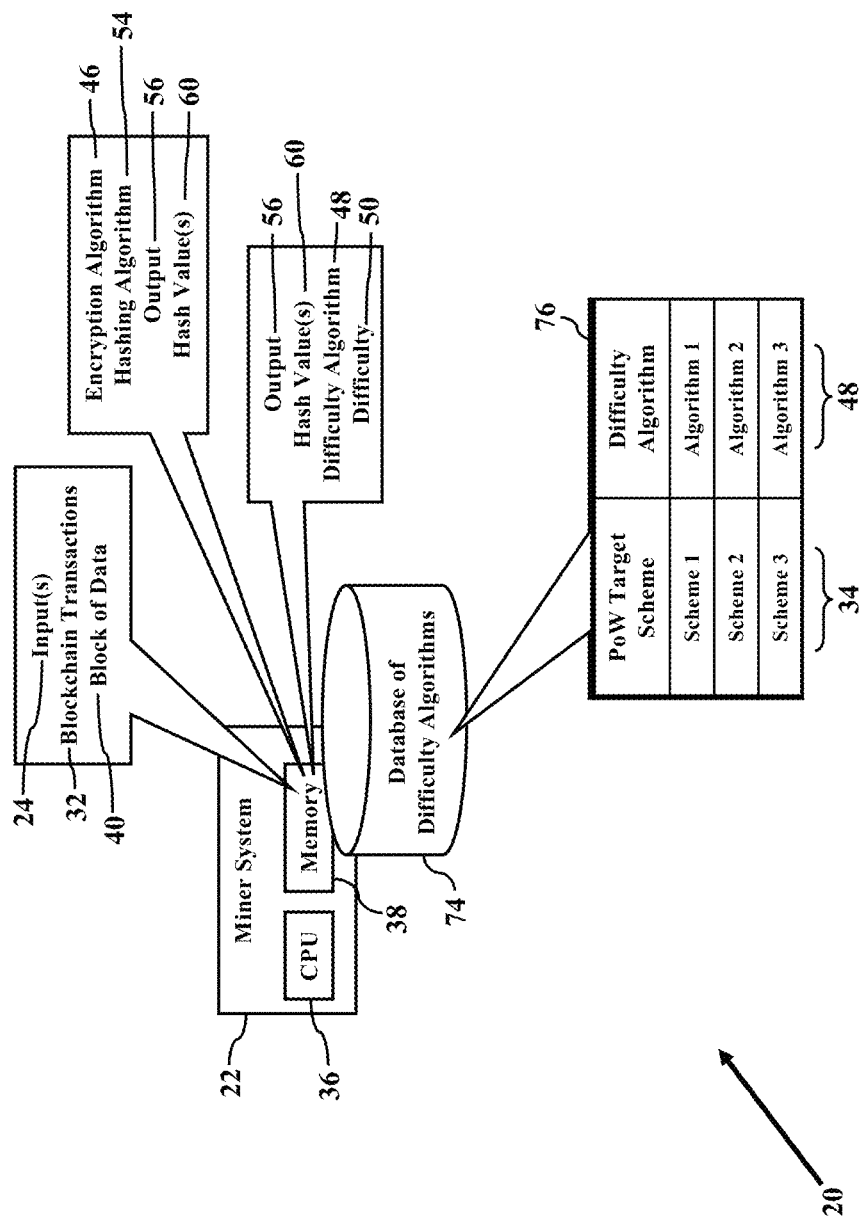

FIG. 8 illustrates agnostic difficulty. Exemplary embodiments may use any difficulty algorithm 48 that a cryptographic coin, blockchain network, or scheme desires or specifies. For example, when or even after the encryption algorithm 46 (e.g., the cryptographic hashing algorithm 54) generates the output 56 (such as the hash value(s) 60), the miner system 22 may request, call, and/or execute the particular difficulty algorithm 48 selected by, or specified by, the proof-of-work target scheme 34 and/or the blockchain environment 20. The proof-of-work target scheme 34 may thus use any difficulty algorithm 48, as the miner system 22 is agnostic to difficulty. FIG. 8, for example, illustrates an electronic database 74 of difficulty algorithms that is accessible to the miner system 22. While the database 74 of difficulty algorithms is illustrated as being locally stored in the memory device 38 of the miner system 22, the database 74 of difficulty algorithms may be remotely stored and accessed/queried at any networked location. Even though the database 74 of difficulty algorithms may have any logical structure, a relational database is again perhaps easiest to understand. FIG. 8 thus illustrates the database 74 of difficulty algorithms as an electronic table 76 that maps, converts, or translates different proof-of-work target schemes 34 to their corresponding or associated difficulty algorithm 48 (such as the particular cryptographic hashing algorithm 54). The miner system 22 may thus identify the difficulty algorithm 48 by querying the electronic database 74 of difficulty algorithms. So, once the particular difficulty algorithm 48 is identified, the miner system 22 may acquire or retrieve any inputs that are required by the difficulty algorithm 48 (such as the output hash value(s) 60 generated by the cryptographic hashing algorithm 54). The miner system 22 may execute the difficulty algorithm 48 specified by the proof-of-work target scheme 34. The miner system 22 may optionally send the hash value(s) 60 via the Internet or other network (e.g., the communications network 26 illustrated in FIGS. 1-3) to a remote destination for service execution (as later paragraphs will explain). The difficulty algorithm 48 creates or generates the difficulty 50 based on the hash value(s) 60.

Figure 9:
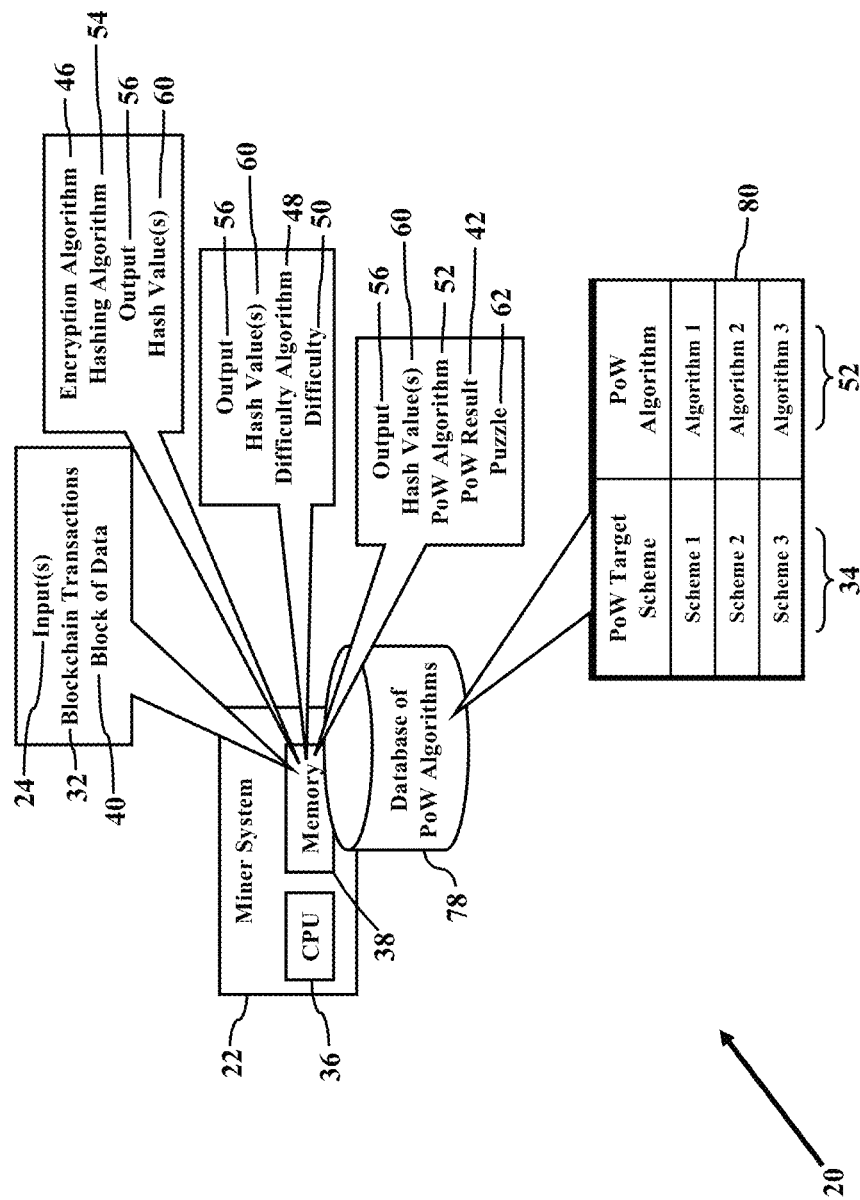

FIG. 9 illustrates agnostic proof-of-work. Exemplary embodiments may use any proof-of-work algorithm 52 that a cryptographic coin, blockchain network, or scheme desires or specifies. The proof-of-work target scheme 34 may thus use any proof-of-work algorithm 52, as the miner system 22 is agnostic to encryption, difficulty, and/or proof-of-work. FIG. 9, for example, illustrates an electronic database 78 of proof-of-work algorithms that is accessible to the miner system 22. While the database 78 of proof-of-work algorithms is illustrated as being locally stored in the memory device 38 of the miner system 22, the database 78 of proof-of-work algorithms may be remotely stored and accessed/queried at any networked location. Even though the database 78 of proof-of-work algorithms may have any logical structure, a relational database is again perhaps easiest to understand. FIG. 9 thus illustrates the database 78 of proof-of-work algorithms as an electronic table 80 that maps, converts, or translates different proof-of-work target schemes 34 to their corresponding proof-of-work algorithm 52. The miner system 22 may thus identify the proof-of-work algorithm 52 by querying the electronic database 78 of proof-of-work algorithms. After the hash value(s) 60 are generated, and perhaps after the difficulty 50 is generated, the miner system 22 may execute the proof-of-work algorithm 52 (specified by the proof-of-work target scheme 34) using the hash value(s) 60 and/or the difficulty 50 as inputs. The miner system 22 may optionally send the hash value(s) 60 and/or the difficulty 50 via the Internet or other network to a remote destination for service execution (as later paragraphs will explain). The proof-of-work algorithm 52 generates the proof-of-work result 42 using the hash value(s) 60 and/or the difficulty 50. The proof-of-work algorithm 52 may also compare the proof-of-work result 42 to the proof-of-work ("PoW") target scheme 34 to ensure or to prove a solution to the mathematical puzzle 62.

Exemplary embodiments may thus use any encryption algorithm 46, any difficulty algorithm 48, and/or any proof-of-work algorithm 52. Exemplary embodiments may implement any cryptographic security. Instead of merely counting zeroes (as specified by BITCOIN'), exemplary embodiments may run the resulting hash value 60 through the difficulty algorithm 48 to calculate the difficulty 50 in order to determine whether it's more or less difficult than other hashes.

Figure 10:
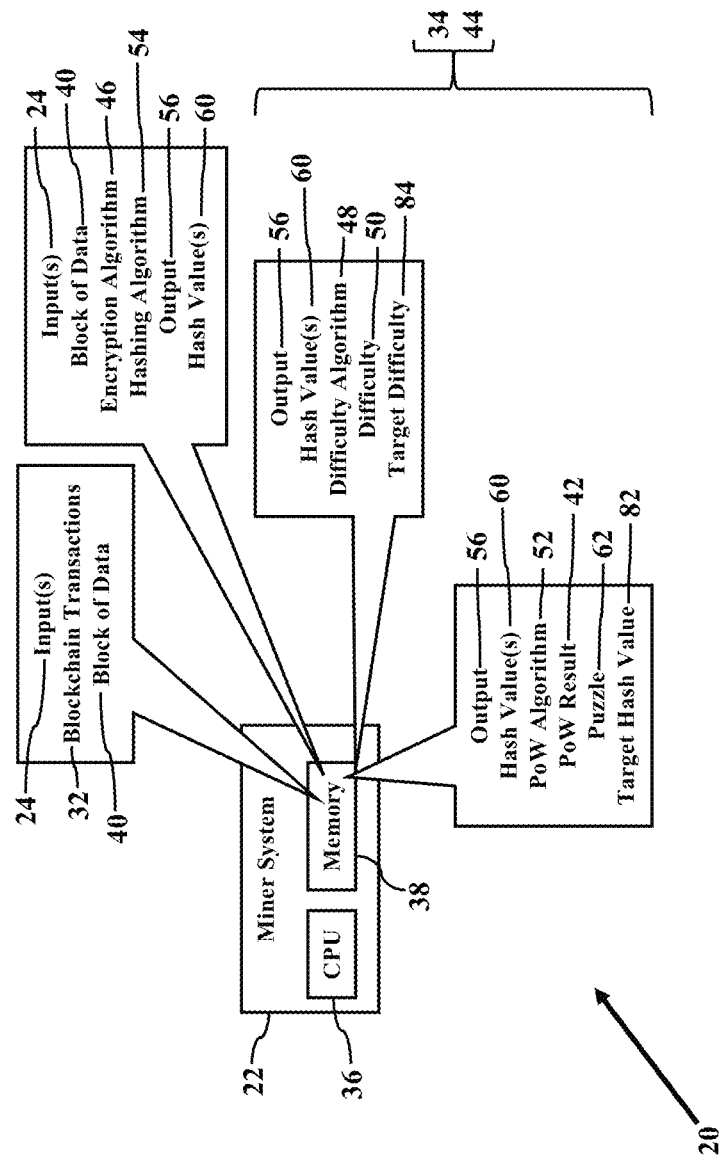

As FIG. 10 illustrates, exemplary embodiments may use any PoW target scheme 34. There are many different target schemes, some of which use or specify random number/nonce values, addresses, starting points, and other security schemes. The proof-of-work algorithm 52, for example, may have to compare the hash value(s) 60 to a target hash value 82. The target hash value 82 may be any minimum or maximum hash value that must be satisfied. If the hash value 60 is less than or perhaps equal to the target hash value 82, then the proof-of-work algorithm 52 has perhaps solved the mathematical puzzle 62. However, if the hash value 60 is greater than the target hash value 82, then perhaps the proof-of-work algorithm 52 has failed to solve the mathematical puzzle 62. Likewise, the hash value 60 may need to be equal to or greater than the target hash value 82 to be satisfactory. Regardless, should the hash value 60 fail to satisfy the target hash value 82, exemplary embodiments may modify any data or input (e.g., the electronic data 30, a random number/nonce value, address, starting points, etc.) according to the proof-of-work target scheme 34, again call or request the cryptographic hashing algorithm 54 to generate the corresponding hash value(s) 60, and compare the hash value(s) 60 to the target hash value 82. Exemplary embodiments may repeatedly modify the electronic data 30 and/or any other parameters until the corresponding hash value(s) 60 satisfy the target hash value 82.

Exemplary embodiments may also use any difficulty scheme. The inventor envisions that there will be many different difficulty schemes. The difficulty algorithm 48, for example, may have to compare the difficulty 50 to a target difficulty 84. The target difficulty 84 has a bit or numeric value that represents a satisfactory difficulty of the corresponding cryptographic hashing algorithm 54 and/or the hash value 60. For example, suppose the target difficulty 84 is a minimum value that represents a minimum permissible difficulty associated with the corresponding cryptographic hashing algorithm 54. If the difficulty 50 is less than or perhaps equal to the target difficulty 84, then perhaps the corresponding cryptographic hashing algorithm 54 and/or the hash value 60 is adequately difficult. However, if the difficulty 50 is greater than the target difficulty 84, then perhaps the corresponding cryptographic hashing algorithm 54 and/or the hash value 60 is too difficult. Likewise, the difficulty 50 may need to be equal to or greater than the target difficulty 84 to be adequately difficult. Regardless, should the difficulty 50 fail to satisfy the target difficulty 84, exemplary embodiments may modify any data or input (e.g., the electronic data 30, a random number/nonce value, address, starting points, etc.) and recompute the corresponding hash value(s) 60. Moreover, exemplary embodiments may additionally or alternatively change the cryptographic hashing algorithm 54 and/or the difficulty algorithm 48 and recompute.

Exemplary embodiments may thus functionally separate hashing, difficulty, and proof-of-work. The conventional proof-of-work target scheme 34 functionally combines or performs both hashing and difficulty. The conventional proof-of-work target scheme 34 integrates or combines the difficulty in the hash. The conventional proof-of-work target scheme 34 integrates or combines the difficulty in the hash, thus greatly complicating the hash determination. Exemplary embodiments, instead, may separate the hashing algorithm 54 from the difficulty algorithm 48. Exemplary embodiments put the difficulty 50 in the measurement of the difficulty 50. Exemplary embodiments remove the difficulty 50 from the hashing algorithm 54. The hashing algorithm 54 is not complicated by also having to integrate/calculate the difficulty algorithm 48. The difficulty algorithm 48 may thus be a separate, stand-alone function or service that determines or calculates which hash is more difficult. The hashing algorithm 54 is much simpler to code and much faster to execute, as the hashing algorithm 54 requires less programming code and less storage space/usage in bytes. The hashing algorithm 54 need not be complicated to deter ASIC mining. Exemplary embodiments need not rely on the hashing algorithm 54 to also determine the difficulty 50 and/or the proof-of-work. The difficulty algorithm 48 is, instead, a separate functional mechanism, perhaps performed or executed by a service provider. Exemplary embodiments thus need not use an electrical power-hungry mechanism that is inherent in the conventional proof-of-work scheme.

Figure 11:
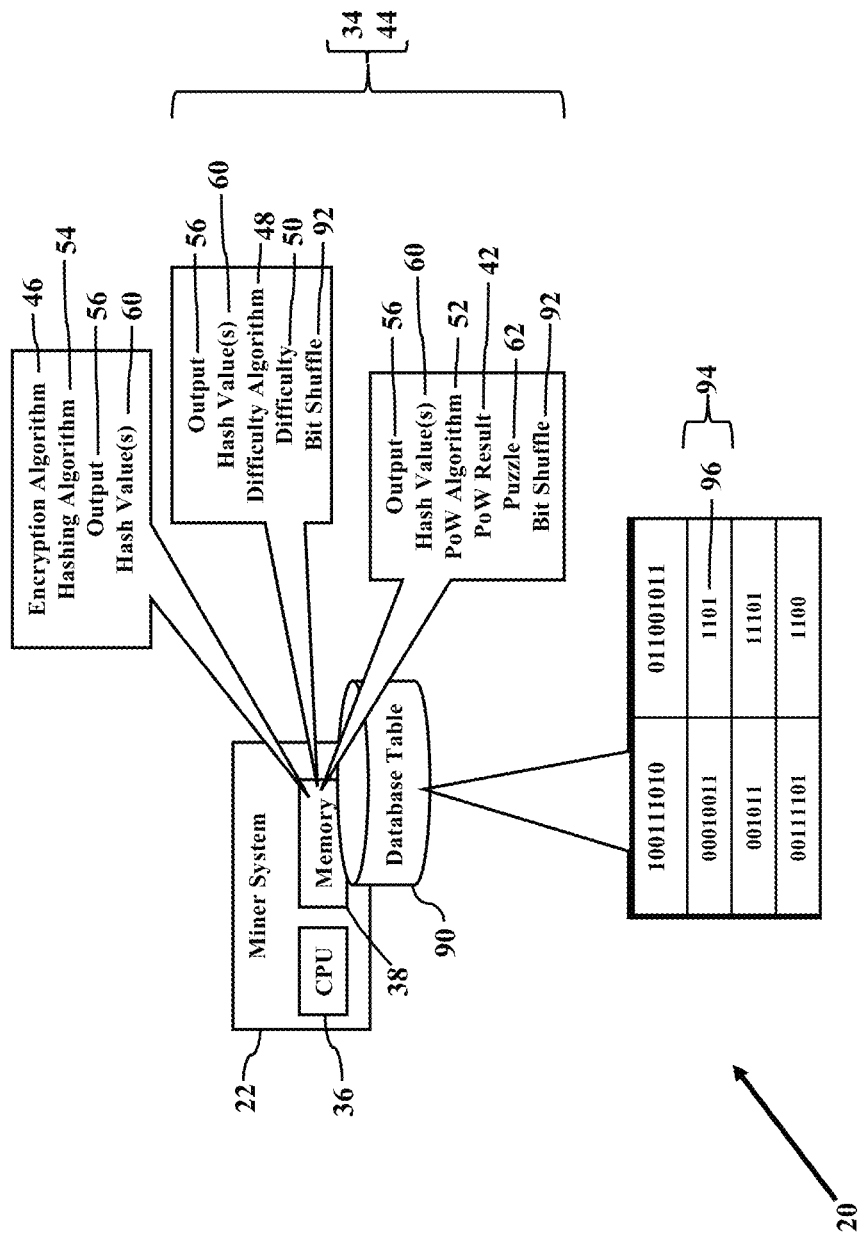

FIG. 11 illustrates a randomized database table 90. The difficulty algorithm 48 and/or the proof-of-work algorithm 52 may use or consult the database table 90 when conducting any proof-of-work (e.g., 34 and/or 44). While exemplary embodiments may use any encryption scheme, most blockchain mining uses some form of hashing. FIG. 11 thus proof-of-work target scheme 34 that utilizes the separate cryptographic hashing algorithm 54, but the difficulty algorithm 48 and/or the proof-of-work algorithm 52 implements a further randomization of the resulting hash value(s) 60. The proof-of-work target scheme 34 or mechanism 44 may generate, store, and/or use the database table 90 when performing any proof-of-work. Exemplary embodiments may implement a bit shuffle operation 92 on the hash value(s) 60. Exemplary embodiments may use entries in the database table 90 to perform the bit shuffle operation 92 (as later paragraphs will explain). Each entry 94 in the database table 90 may contain a random selection of bits/bytes 96. The difficulty algorithm 48 and/or the proof-of-work algorithm 52 may select any bit values representing the hash value(s) 60 and swap any one or more of the bit values with any one or more entries 94 specified by the database table 90. The difficulty algorithm 48 and/or the proof-of-work algorithm 52 may read or select a bit portion of the bit values representing the hash value(s) 60 and exchange or replace the bit portion with an entry 94 contained in, or referenced by, the database table 90. Each entry 94 in the database table 90 represents or is associated with random bits or bytes. Exemplary embodiments may thus randomly shuffle the hash value(s) 60 generated by the cryptographic hashing algorithm 54. Exemplary embodiments randomize byte or memory block access.

Figure 12:
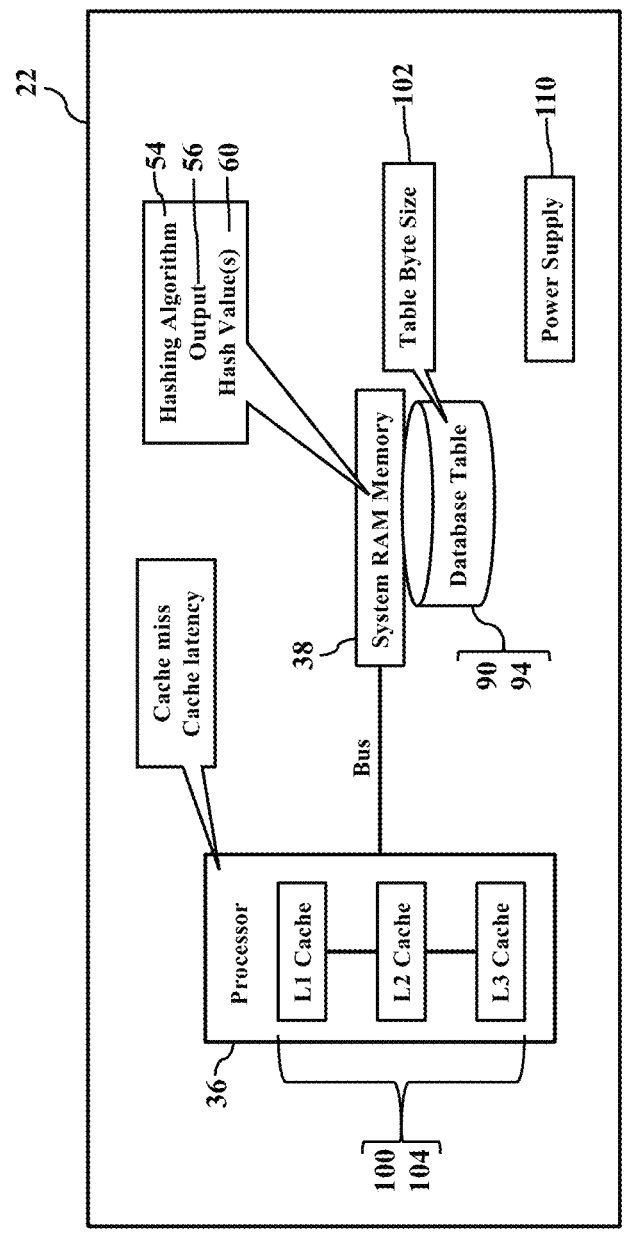

FIG. 12 illustrates RAM binding. Exemplary embodiments may discourage or deter the use of specialized hardware (such as GPUs and ASICs) in blockchain mining. The proof-of-work target scheme 34, for example, may take advantage of, or target, memory size restrictions and cache latency of any on-board processor cache memory 100. As the reader may understand, any hardware processing element (whether a GPU, an ASIC, or the CPU 36) may have integrated/embedded L1, L2, and L3 SRAM/DRAM cache memory. The processor cache memory 100 is generally much smaller than a system/main memory (such as the memory device 38), so the hardware processing element may store frequently-needed data and instructions. Because the processor cache memory 100 is physically much closer to the processing core, any hardware processing element is able to quickly fetch or hit needed information. If the processor cache memory 100 does not store the needed information, then a cache miss has occurred and the hardware processing element must request and write blocks of data via a much-slower bus from the system/main memory 38. A cache miss implies a cache latency in time and/or cycles to fetch the needed information from the system/main memory 38. Any hardware processing element (again, whether a GPU, an ASIC, or the CPU 36) may sit idle, or stall, while awaiting fetches from the system/main memory 38.

Exemplary embodiments may thus force latency, cache misses, and stalls. Exemplary embodiments may target cache latency and processor stalls by generating, storing, and/or using the database table 90 when determining the hash value(s) 60 (as later paragraphs will explain). The database table 90, however, may be sized to overload the processor cache memory 100. The database table 90, in other words, may have a table byte size 102 (in bits/bytes) that exceeds a storage capacity or cache byte size 104 of the processor cache memory 100. The database table 90, for example, may exceed one gigabyte (1 GB). Today's L1, L2, and L3 processor cache memory is typically hundreds of megabits in size. Because the database table 90 may exceed one gigabyte (1 GB), any caching operation will miss or invalidate. That is, the L1, L2, and L3 processor cache memory 100 lacks the storage capacity or byte size 104 to store the entire database table 90. Perhaps only a portion (or perhaps none) of the database table 90 may be stored in the processor cache memory 100. Indeed, exemplary embodiments thus force some, most, or even all of the database table 90 to be written or stored to the main/host memory device 38 (or accessed/retrieved from a remote source, as later paragraphs will explain). Because any hardware processing element (again, whether a GPU, an ASIC, or the CPU 36) is unable to cache the entire database table 90, exemplary embodiments force a cache miss and further force the hardware processing element to repeatedly use the processor cache memory 100 to fetch and load a portion of the database table 90. The main/system memory 38 thus provides perhaps a particular portion of the database table 90 via the bus to the processor cache memory 100, and the processor cache memory 100 then provides that particular portion of the database table 90 to the hardware processing element. The hardware processing element may then purge or delete that particular portion of the database table 90 from the processor cache memory 100 and request/fetch/load another portion of the database table 90. Because exemplary embodiments may force repeated cache misses, the hardware processing element may continuously repeat this cycle for loading/retrieving most or all portions of the database table 90. The hardware processing element, in other words, repeatedly queries the processor cache memory 100 and/or the main/host memory device 38 and awaits data retrieval. The hardware processing element must therefore sit, perhaps mostly idle, while the processor cache memory 100 and/or the main/host memory device 38 processes, retrieves, and sends different segments/portions/blocks of the database table 90. The processor cache memory 100 and/or the main/host memory device 38 have the cache latency (perhaps measured in clock cycles, data transfer rate, or time) that limits blockchain computations. A faster processor/GPU/ASIC, in other words, will not improve memory access times/speeds, so any computational speed/performance is limited by the latency of repeatedly accessing the processor cache memory 100 and/or the main/host memory device 38. The database table 90 thus deters GPU/ASIC usage when processing the blockchain transactions 32. The database table 90 may thus be purposefully designed to be non-cacheable by intensively using the processor cache memory 100 and/or the main/host memory device 38 as an ASIC-deterrence mechanism.

Byte or memory block access may be randomized. Whatever the hashing algorithm 54, exemplary embodiments may implement the bit shuffle operation 92 on the hash value(s) 60. Exemplary embodiments may use the entries 94 in the database table 90 to perform the bit shuffle operation 92 (as later paragraphs will further explain). The proof-of-work target scheme 34 may use bit values representing the hash value(s) 60, but the proof-of-work target scheme 34 may swap any one or more of the bit values with any one or more entries 94 specified by the database table 90. Each entry 94 in the database table 90 may contain a random selection of bits/bytes. The proof-of-work target scheme 34 may cause the proof-of-work algorithm 52 to read or to select a bit portion of the bit values representing the hash value(s) 60 and exchange or replace the bit portion with an entry 94 contained in, or referenced by, the database table 90. Each entry 94 in the database table 90 represents or is associated with random bits or bytes. The proof-of-work target scheme 34 may thus randomly shuffle the hash value(s) 60 generated by the cryptographic hashing algorithm 54.

Exemplary embodiments may discourage or deter specialized hardware in blockchain mining. The miner system 22 must have access to the database table 90 in order to execute the bit shuffle operation 92, difficulty algorithm 48, and/or the proof-of-work algorithm 52. Because any processing component (e.g., ASIC, GPU, or the CPU 36) is unable to cache the entire database table 90, exemplary embodiments force the processing component to query the processor cache memory 100 and/or the main/host memory device 38 and to await data retrieval. The hardware processing component must therefore sit, perhaps mostly idle, while the processor cache memory 100 and/or the main/host memory device 38 processes, retrieves, and sends different segments/portions/blocks of the database table 90. A faster GPU/ASIC will thus not improve memory access times/speeds. Exemplary embodiments thus force miners to choose the CPU 36, as a faster GPU/ASIC provides no performance/speed gain. Moreover, because a faster GPU/ASIC is ineffective, the extra capital expense of a faster GPU/ASIC offers little or no benefit and cannot be justified. Exemplary embodiments thus bind miners to the CPU 36 for blockchain processing/mining.

Exemplary embodiments thus include RAM hashing. The electronic database table 90 may have a random number of columns and/or a random number of rows. The electronic database table 90 may have a random number of database entries 94. Moreover, each columnar/row database entry 94 may also have a random sequence or selection of bits/bytes (1's and 0's). So, whatever the hash values 60 generated by the hashing algorithm 54, the separate difficulty algorithm 48 and/or proof-of-work algorithm 52 may use the electronic database table 90 to further randomize the hash values 60 for additional cryptographic security. Indeed, because only at least a portion of the electronic database table 90 may be stored in the processor cache memory 100, exemplary embodiments effectively confine hashing operations to the main/host memory device 38 (such as a subsystem RAM). Regardless of what device or service provider executes the hashing algorithm 54, the electronic database table 90, which is mostly or entirely stored in the main/host memory device 38, provides the randomized inputs to the separate difficulty algorithm 48 and/or proof-of-work algorithm 52. Operationally and functionally, then, exemplary embodiments divorce or functionally separate any hardware processing element from the hashing operation. Simply put, no matter what the performance/speed/capability of the ASIC, GPU, or the CPU 36, the database table 90 may be randomly sized to always exceed the storage capacity or cache byte size 104 of the processor cache memory 100. Hashing operations are thus reliant on cache latency, cache misses, and processor stalls when using the database table 90. The hashing operations are thus largely confined to, and performed by, the off-board or off-processor main/host memory device 38 (such as a subsystem RAM). Because the main/host memory device 38 performs most or all of the cryptographic security, the hardware processing component (ASIC, GPU, or the CPU 36) may play little or no role in the hashing operations (perhaps only performing database lookup queries). Again, a better/faster ASIC or GPU provides little to no advantage in the hashing operations.

Moreover, the main/host memory device 38 consumes much less electrical power, thus further providing reduced energy costs that deter/resist ASIC/GPU usage.

Exemplary embodiments may also add cryptographic security. Exemplary embodiments may force the miner/network to possess, or have authorized access to, the database table 90. In simple words, the proof-of-work target scheme 34 swaps random bytes in the hash value 60 with other random bytes specified by the database table 90. Any party that provides or determines a proof-of-work must possess (or have access to) the database table 90. If the difficulty algorithm 48 and/or the proof-of-work algorithm 52 lacks authorized access to the database table 90, then the difficulty algorithm 48 and/or the proof-of-work algorithm 52 cannot query the database table 90 nor perform database lookup operations. Difficulty and/or proof-of-work will fail without having access to the database table 90.

Exemplary embodiments may also separately specify the difficulty algorithm 48. The proof-of-work target scheme 34 may cause the miner system 22 to apply the bit shuffle operation 92 to the hash value 60. The proof-of-work target scheme 34 may also specify the difficulty algorithm 48 and the target difficulty 84, perhaps having a high number or value. Because these byte accesses to the processor cache memory 100 are random and over a gigabyte of the memory space, the byte accesses blow or exceed the retrieval and/or byte size storage capabilities of the processor cache memory 100. The proof-of-work target scheme 34 thus forces the miner system 22 to wait on the slower main/host memory device 38 (rather than waiting on the speed of the hardware processing component). A faster/better hardware processing element (such as an ASIC), in other words, does not alleviate the bottleneck of accessing the main/host memory device 38. Moreover, because exemplary embodiments may heavily rely on the main/host memory device 38 (rather than the hardware processing component) to do proof of work, the miner system 22 consumes significantly less of electrical power (supplied by a power supply 110). Because the proof-of-work algorithm 52 and the difficulty algorithm 48 may be separate from the cryptographic hashing algorithm 54, exemplary embodiments utilize the security of a well-tested hashing function, but exemplary embodiments also require the proof-of-work scheme to use the main/host memory device 38, which makes it unreasonable to build ASICS.

Exemplary embodiments may thus force usage of a particular physical memory. Exemplary embodiments, for example, may overload the processor cache memory 100 by gorging the byte size of the database table 90 with additional database entries. Even as L1, L2, and L3 processor cache memory 100 increases in the storage capacity or byte size 104, exemplary embodiments may concomitantly increase the table byte size 102 (in bits/bytes) to ensure the database table 90 continues to exceeds the storage capacity or byte size 104 of the processor cache memory 100. Exemplary embodiments may thus bind the encryption algorithm 46, the difficulty algorithm 48, and/or the proof-of-work algorithm 52 to the main/host memory device 38 to deter GPU/ASIC usage.

Exemplary embodiments may also unbind the hashing algorithm 54 from the difficulty algorithm 48. Exemplary embodiments easily validate the proof-of-work by changing how proof-of-work is calculated without changing the hashing algorithm 54. Because the hashing algorithm 54 is disassociated or disconnected from the difficulty algorithm 48, the cryptographically security of the hashing algorithm 54 is increased or improved. Moreover, the separate difficulty algorithm 48 and/or proof-of-work algorithm 52 may have other/different objectives, without compromising the cryptographically security of the hashing algorithm 54. The difficulty algorithm 48 and/or proof-of-work algorithm 52, for example, may be designed for less consumption of the electrical power. The difficulty algorithm 48 and/or proof-of-work algorithm 52 may additionally or alternatively be designed to deter/resist ASIC/GPU usage, such as increased usage of the processor cache memory 100 and/or the main/host memory device 38. The difficulty algorithm 48 and/or proof-of-work algorithm 52 need not be cryptographically secure. Because the hashing algorithm 54 ensures the cryptographically security, the difficulty algorithm 48 and/or proof-of-work algorithm 52 need not be burdened with providing the cryptographically security. The difficulty algorithm 48 and/or proof-of-work algorithm 52 each require less programming code and less storage space/usage in bytes, so each is much simpler to code and much faster to execute.

Figure 13:
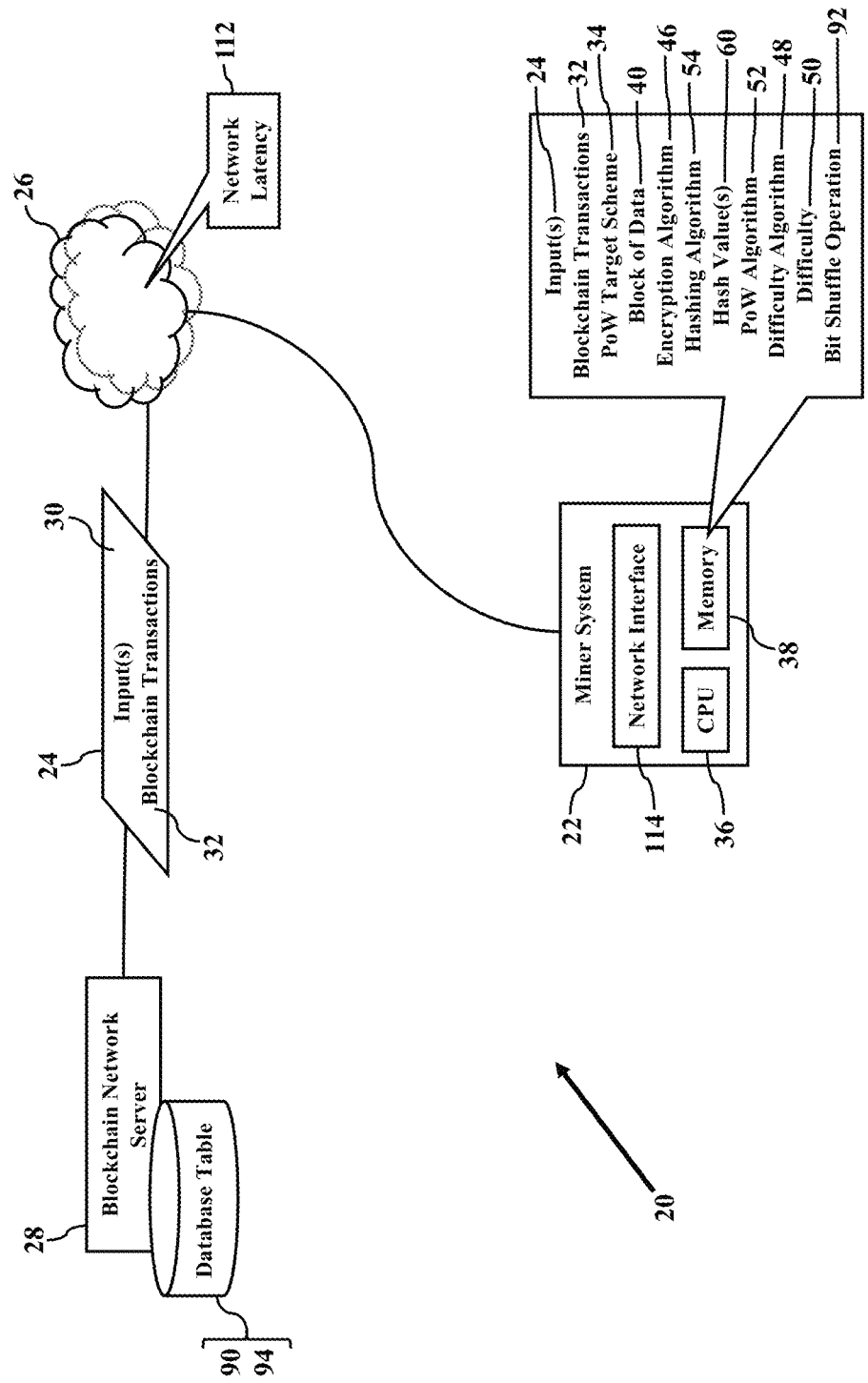

FIG. 13 illustrates network binding. Because the encryption algorithm 46, the difficulty algorithm 48, and the proof-of-work algorithm 52 may be separate software modules, routines, or clients, network communications may be used to deter specialized hardware. As FIG. 13 illustrates, the miner system 22 communicates with the blockchain network server 28 via the communications network 26. Because the miner system 22 may be authorized to perform blockchain mining (perhaps according to the proof-of-work target scheme 34 specified or used by the blockchain network server 28), the miner system 22 may receive the inputs 24 from the blockchain network server 28. The miner system 22, in other words, must use the communications network 26 to receive the inputs 24 and to subsequently mine the inputs 24. The miner system 22 uses the inputs 24 to determine the hash value 60 and/or the difficulty 50 (as this disclosure above explains). However, suppose the blockchain network server 28 stores the database table 90 that is required for the difficulty algorithm 48 and/or the proof-of-work algorithm 52. Even though the miner system 22 may execute the encryption algorithm 46, the difficulty algorithm 48, and/or the proof-of-work algorithm 52, the miner system 22 may be forced to send one or more database queries to the blockchain network server 28. The blockchain network server 28 may have a hardware processing element and a memory device (not shown for simplicity) that stores the database table 90. The blockchain network server 28 may also store and execute a query handler software application (also not shown for simplicity) that receives queries from clients, identifies or looks up entries 94 in the database table 90, and sends query responses to the clients. So, when the miner system 22 is instructed to perform, or require, the bit shuffle operation 92, the miner system 22 may thus be forced to retrieve any entry 94 (specified by the database table 90) via the communications network 26 from the blockchain network server 28. The miner system 22 may thus send the database query to the network address assigned to or associated with the blockchain network server 28. The miner system 22 then awaits a query response sent via the communications network 26 from the blockchain network server 28, and the query response includes or specifies the random selection of bits/bytes retrieved from the particular entry 94 in the database table 90. The miner system 22 may then perform the bit swap operation 92 on the hash value(s) 60 (as this disclosure above explains).

Exemplary embodiments may use a network latency 112 to discourage or deter specialized hardware. Because the blockchain network server 28 may store the database table 90, the miner system 22 is performance bound by the network latency 112 in the communications network 26. Packet communications between the blockchain network server 28 and the destination miner system 22 require time, and the network latency 112 is affected by network routing, network segment travel distances, network traffic, and many other factors. Exemplary embodiments may thus additionally or alternatively force the miner system 22 to wait on the communications network 26 to obtain any entry 94 in the database table 90. A faster/better hardware processing component (such as an ASIC) does not overcome bottleneck(s) due to the network latency 112 in the communications network 26. Moreover, because the electrical power required by a network interface 114 is likely less than the hardware processing component, the miner system 22 consumes significantly less of electrical power.

Figure 14:
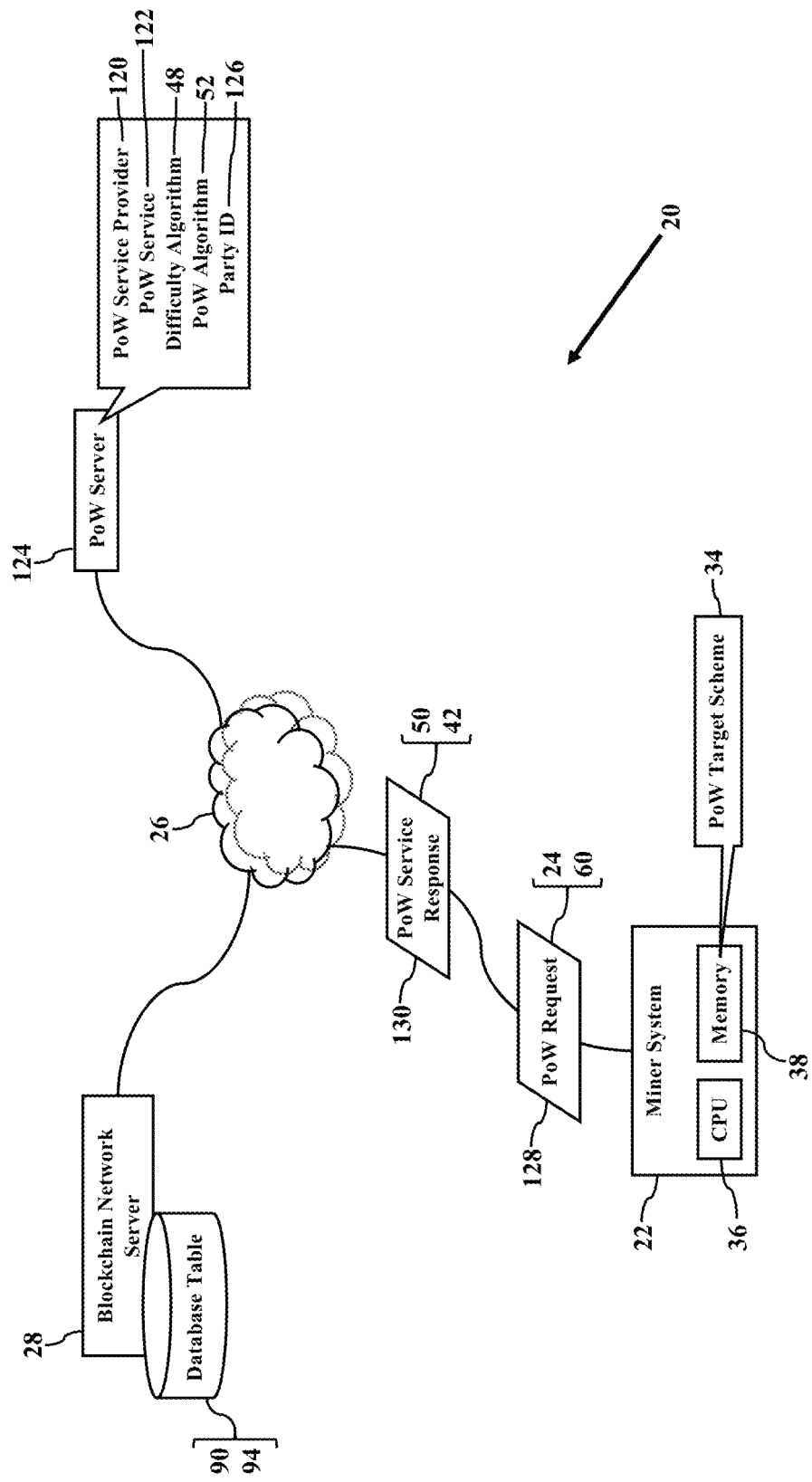

FIG. 14 illustrates party binding. Here the miner system 22 may utilize an authorized proof-of-work ("PoW") service provider 120 that provides a PoW service 122. The miner system 22 may communicate with a PoW server 124 via the communications network 26, and the PoW server 124 is operated by, or on behalf of, the PoW service provider 120. Perhaps only the PoW service provider 120 may be authorized to execute the difficulty algorithm 48 and/or the proof-of-work algorithm 52 as a provable party. The PoW server 124 may have a hardware processing element and a memory device (not shown for simplicity) that stores the difficulty algorithm 48 and/or the proof-of-work algorithm 52. If an incorrect or unauthorized party attempts the proof-of-work, the proof-of-work is designed to fail. As an example, FIG. 14 illustrates a party identifier 126 as one of the inputs 24 to the difficulty algorithm 48 and to the proof-of-work algorithm 52. While the party identifier 126 may be supplied or sent from any network location (such as the blockchain network server 28 and/or the miner system 22), the party identifier 126 may be locally retrieved from the memory device of the PoW server 124. The miner system 22 may send a PoW request 128 to a network address (e.g., IP address) associated with the PoW server 124. The PoW request 128 may include or specify one or more of the inputs 24 to the difficulty algorithm 48 and/or to the proof-of-work algorithm 52. Suppose, for example, that the PoW request 128 includes or specifies the hash value(s) 60 (determined by the hashing algorithm 54, as above explained). The PoW server 124 may generate the difficulty 50 (by calling or executing the difficulty algorithm 48) and/or the proof-of-work result 42 (by calling and/or by executing the proof-of-work algorithm 52) using the hash value(s) 60 and the party identifier 126. The PoW server 124 may then send the difficulty 50 and/or the proof-of-work result 42 as a PoW service response 130 back to the IP address associated with the miner system 22 and/or back to the IP address associated with the blockchain network server 28. Either or both of the PoW server 124 and/or the blockchain network server 28 may compare the difficulty 50 and/or the proof-of-work result 42 to the proof-of-work ("PoW") target scheme 34. If the difficulty 50 and/or the proof-of-work result 42 satisfies the proof-of-work ("PoW") target scheme 34, then the correct, authorized party has solved the mathematical puzzle 62 associated with the mining scheme.

Exemplary embodiments may thus be socially bound. Because the party identifier 126 may be an input to the difficulty algorithm 48 and/or to the proof-of-work algorithm 52, the party identifier 126 must specify the correct name, code, alphanumeric combination, binary value, or any other representation of the PoW service provider 120. If the wrong, incorrect, or unauthorized value is input, the difficulty algorithm 48 and/or the proof-of-work algorithm 52 will generate incorrect results that cannot satisfy the proof-of-work ("PoW") target scheme 34. An unauthorized party has been used to conduct the proof-of-work.

Figure 15:
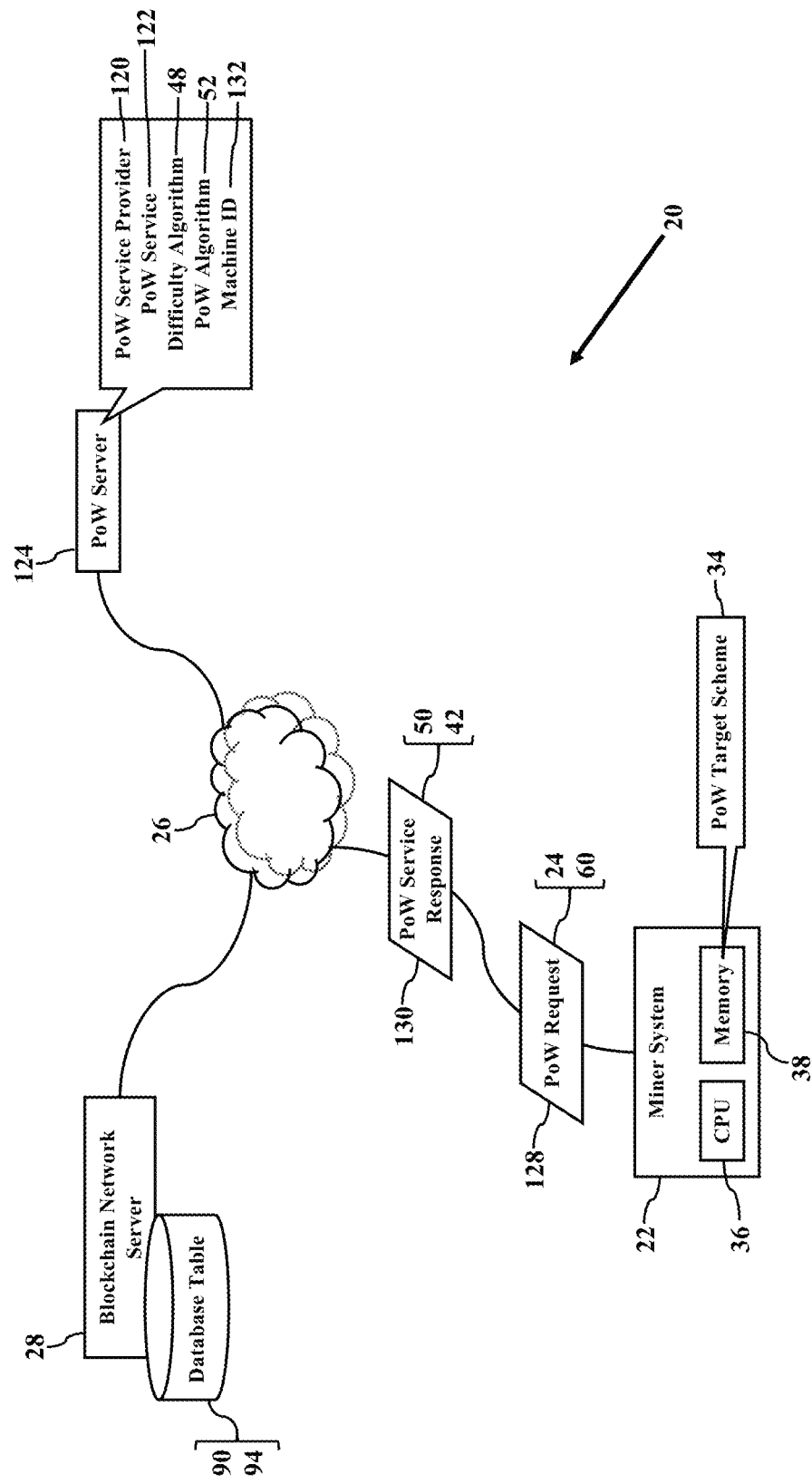

FIG. 15 illustrates machine binding. Here the miner system 22 may utilize a particular machine, device, or other computer to provide the PoW service 122. The miner system 22, for example, must use the PoW server 124 to execute the difficulty algorithm 48 and/or the proof-of-work algorithm 52 as a provable party. That is, perhaps only the PoW server 124 is authorized to execute the difficulty algorithm 48 and/or the proof-of-work algorithm 52. A different computer or server, even if also operated by, or on behalf of, the PoW service provider 120, is ineligible or unauthorized. FIG. 15 thus illustrates a machine identifier 130 as one of the inputs 24 to the difficulty algorithm 48 and/or to the proof-of-work algorithm 52. The machine identifier 130 is any value, number, or alphanumeric combination that uniquely identifies the PoW server 124 executing the difficulty algorithm 48 and/or the proof-of-work algorithm 52. The machine identifier 130, for example, may be a chassis or manufacturer's serial number, MAC address, or IP address that is assigned to or associated with the PoW server 124. When the PoW server 124 receives the input(s) 24 from the miner system 22 (perhaps via the PoW request 128, as above explained), the PoW server 124 may generate the difficulty 50 and/or the proof-of-work result 42 using the hash value(s) 60 and the machine identifier 130 as inputs. The PoW server 124 may then send the difficulty 50 and/or the proof-of-work result 42 as a PoW service response 130 back to the IP address associated with the miner system 22 and/or back to the IP address associated with the blockchain network server 28. Either or both of the PoW server 124 and/or the blockchain network server 28 may compare the difficulty 50 and/or the proof-of-work result 42 to the proof-of-work ("PoW") target scheme 34. If the difficulty 50 and/or the proof-of-work result 42 satisfy the proof-of-work ("PoW") target scheme 34, then the correct, authorized machine or device has solved the mathematical puzzle 62 associated with the mining scheme. Exemplary embodiments may thus be machine bound. If the wrong, incorrect, or unauthorized machine identifier 130 is input, the difficulty algorithm 48 and/or the proof-of-work algorithm 52 will generate incorrect results that cannot satisfy the proof-of-work ("PoW") target scheme 34. An unauthorized computer has been used to conduct the proof-of-work.

Figure 16:
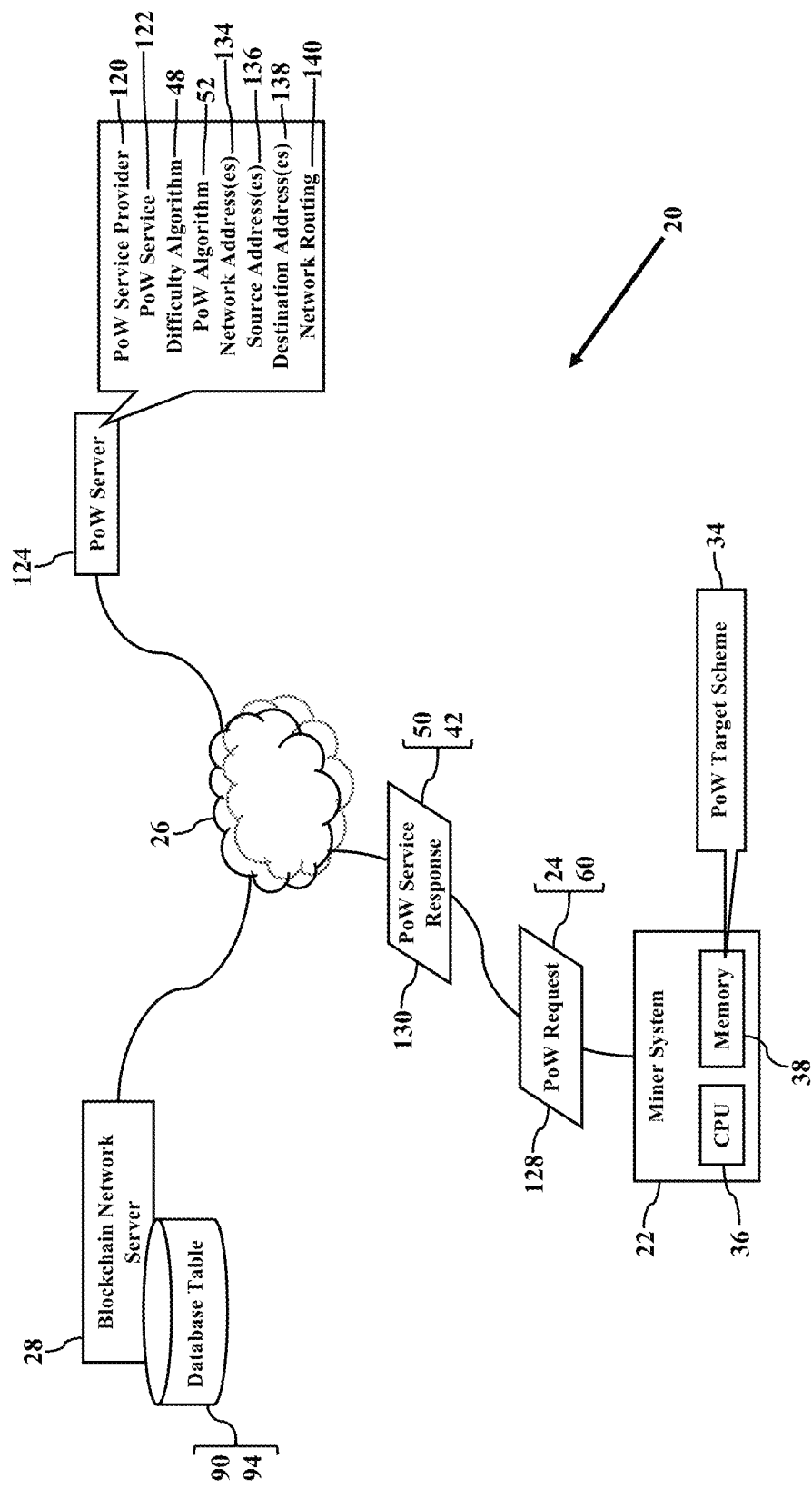

FIG. 16 further illustrates network binding. Here a predetermined network addressing scheme must be used to conduct the difficulty 50 and/or the proof-of-work result 42. Suppose, for example, that the proof-of-work ("PoW") target scheme 34 requires one or more predetermined network addresses 134 when executing the difficulty algorithm 48 and/or the proof-of-work algorithm 52. The inputs 24 to the difficulty algorithm 48 and/or to the proof-of-work algorithm 52, for example, may include one or more source addresses 136 and/or one or more destination addresses 138 when routing packetized data via the communications network 26 from the miner system 22 to the PoW service provider 120 (e.g., the PoW server 124). The hash values 60, in other words, must traverse or travel a predetermined network routing 140 in order to satisfy the proof-of-work ("PoW") target scheme 34. The predetermined network routing 140 may even specify a chronological list or order of networked gateways, routers, switches, servers, and other nodal addresses that pass or route the inputs 24 from the miner system 22 to the PoW server 124. The source addresses 136, the destination addresses 138, and/or the predetermined network routing 140 may thus be additional data inputs 24 to the difficulty algorithm 48 and/or to the proof-of-work algorithm 52. The PoW server 124 may perform network packet inspection to read/retrieve the source addresses 136, the destination addresses 138, and/or the predetermined network routing 140 associated with, or specified by, a data packet. When the PoW server 124 receives the input(s) 24 from the miner system 22 (perhaps via the PoW request 128, as above explained), the PoW server 124 may generate the difficulty 50 and/or the proof-of-work result 42 using the hash value(s) 60, the source addresses 136, the destination addresses 138, and/or the predetermined network routing 140. The PoW server 124 may then send the difficulty 50 and/or the proof-of-work result 42 as the PoW service response 130 back to the IP address associated with the miner system 22 and/or back to the IP address associated with the blockchain network server 28. Either or both of the PoW server 124 and/or the blockchain network server 28 may compare the difficulty 50 and/or the proof-of-work result 42 to the proof-of-work ("PoW") target scheme 34. If the difficulty 50 and/or the proof-of-work result 42 satisfy the proof-of-work ("PoW") target scheme 34, then the correct, authorized networked devices were used to solve the mathematical puzzle 62 associated with the mining scheme. If a wrong, incorrect, or unauthorized routing was used, the difficulty algorithm 48 and/or the proof-of-work algorithm 52 will fail to satisfy the proof-of-work ("PoW") target scheme 34. An unauthorized network of computers has been used to conduct the proof-of-work.

Figure 17:
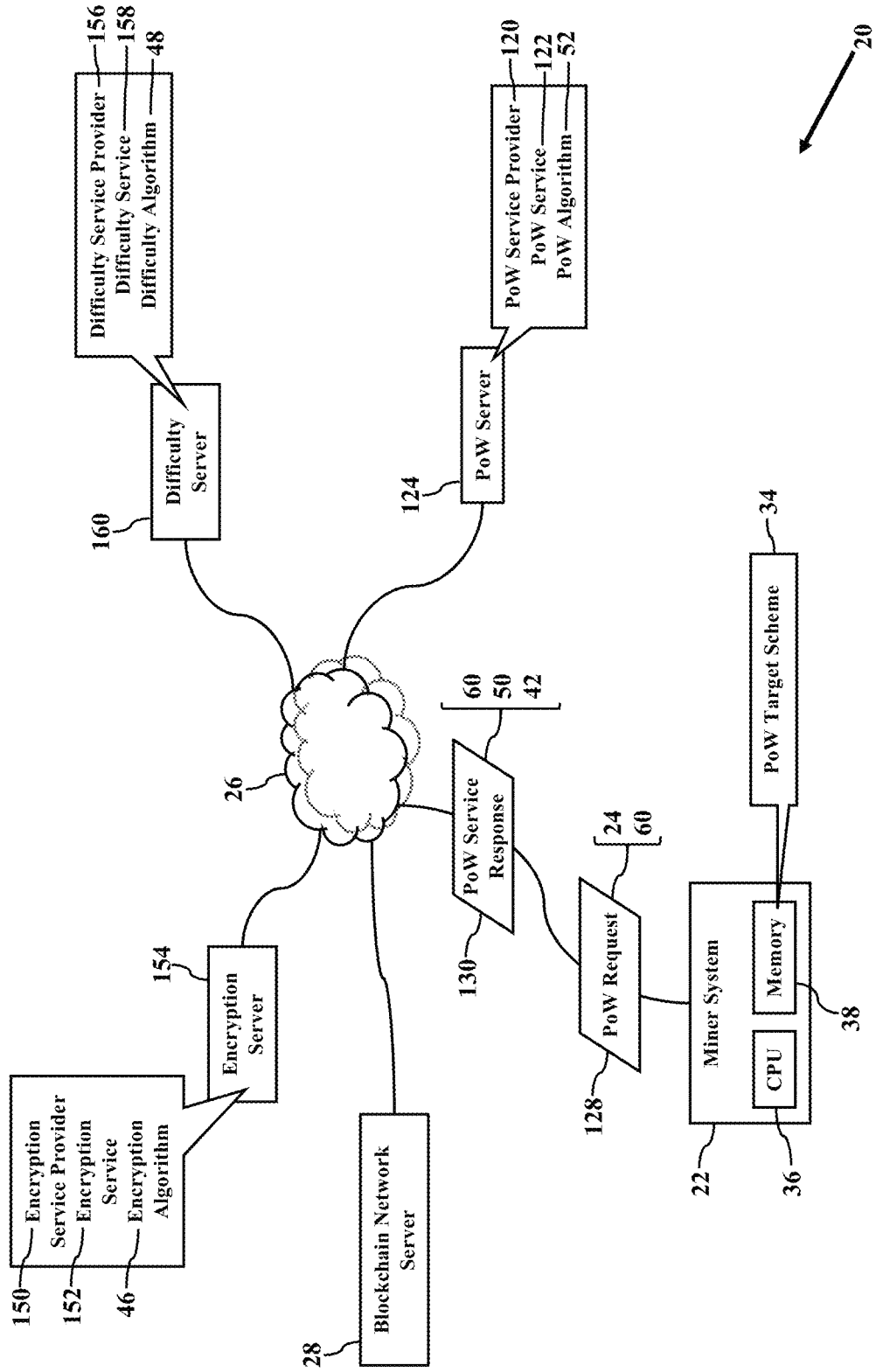

FIG. 17 illustrates vendor processing. The miner system 22 may communicate with one or more service providers via the communications network 26. The miner system 22 may enlist or request that any of the service providers provide or perform a processing service. An encryption service provider 150, for example, may provide an encryption service 152 by instructing an encryption server 154 to execute the encryption algorithm 46 chosen or specified by the miner system 22 and/or the blockchain network server 28. A difficulty service provider 156 may provide a difficulty service 158 by instructing a difficulty server 160 to execute the difficulty algorithm 48 chosen or specified by the miner system 22 and/or the blockchain network server 28. The proof-of-work (PoW) service provider 120 (e.g., the PoW server 124) may provide the PoW service 122 by executing the proof-of-work algorithm 52 chosen or specified by the miner system 22 and/or the blockchain network server 28. The miner system 22 may thus outsource or subcontract any of the encryption algorithm 46, the difficulty algorithm 48, and/or the proof-of-work algorithm 52 to the service provider(s). Because the encryption algorithm 46, the difficulty algorithm 48, and/or the proof-of-work algorithm 52 may be separate software mechanisms or packages, the service providers 150, 156, and 120 may specialize in their respective algorithms 46, 48, and 52 and/or services 152, 158, and 122. The encryption service provider 150, for example, may offer a selection of different encryption services 152 and/or encryption algorithms 46, with each encryption service 152 and/or encryption algorithm 46 tailored to a specific encryption need or feature. The difficulty service provider 156 may offer a selection of different difficulty services 158 and/or difficulty algorithms 48 that are tailored to a specific difficulty need or feature. The PoW service provider 120 may offer a selection of different PoW services 122 and/or PoW algorithms 52 that are tailored to a specific proof-of-work need or feature. The blockchain network server 28, the miner system 22, and/or the proof-of-work ("PoW") target scheme 34 may thus mix-and-match encryption, difficulty, and proof-of-work options.

Exemplary embodiments may thus decouple encryption, difficulty, and proof-of-work efforts. Because the encryption algorithm 46 may be a stand-alone software offering or module, exemplary embodiments greatly improve encryption security. The encryption algorithm 46 (such as the hashing algorithm 54) need not intertwine with the difficulty algorithm 48 and/or the proof-of-work algorithm 52. Because the hashing algorithm 54 may be functionally divorced from difficulty and proof-of-work calculations, the hashing algorithm 54 remains a safe, secure, and proven cryptology scheme without exposure to software bugs and errors introduced by difficulty and proof-of-work needs. The difficulty algorithm 48 may also be severed or isolated from encryption and proof-of-work, thus allowing a blockchain scheme to dynamically alter or vary different difficulty calculations without affecting encryption and/or proof-of-work. The proof-of-work algorithm 52 may also be partitioned, split off, or disconnected from encryption and difficulty, thus allowing any blockchain scheme to dynamically alter or vary different proof-of-work calculations or schemes without affecting encryption and/or difficulty.

Figure 18:
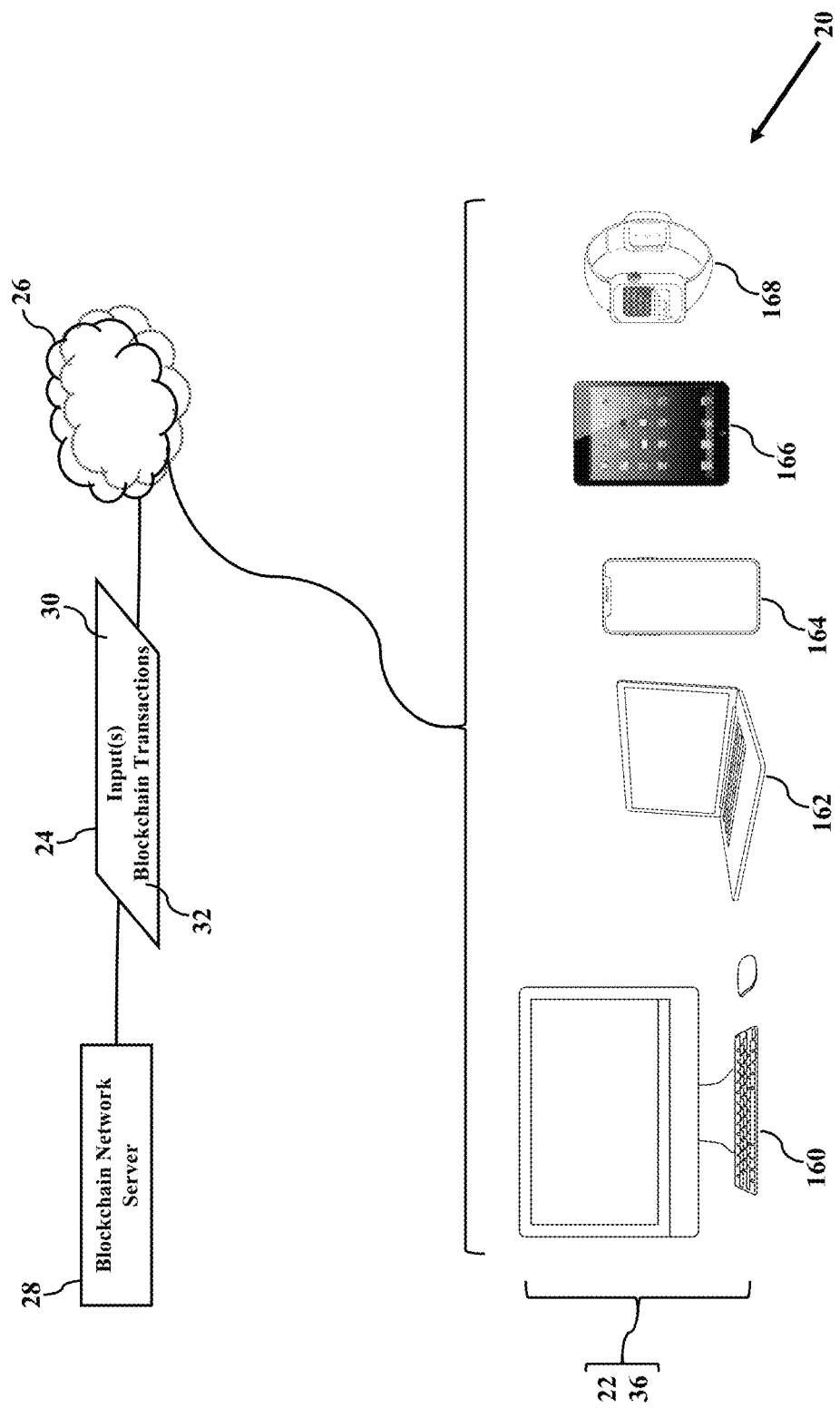

FIG. 18 illustrates democratic mining. Exemplary embodiments reduce or even eliminate the need for graphics processors and specialized application-specific integrated circuits. The miner system 22 may thus rely on a conventional central processing unit (such as the CPU 36) to process the blockchain transactions 32. The miner system 22 may thus be a conventional home or business server/desktop 160 or laptop computer 162 that is much cheaper to purchase, use, and maintain. Moreover, the miner system 22 may even be a smartphone 164, tablet computer 166, or smartwatch 168, as these devices also have adequate processing and memory capabilities to realistically mine and win the block 40 of data (illustrated in FIGS. 1-10). Indeed, the miner system 22 may be any network-connected device, as exemplary embodiments reduce or even eliminate the need for specialized hardware processors. The miner system 22 thus opens-up blockchain mining to any network-connected appliance (e.g., refrigerator, washer, dryer), smart television, camera, smart thermostat, or other Internet of Thing.

Figure 19:
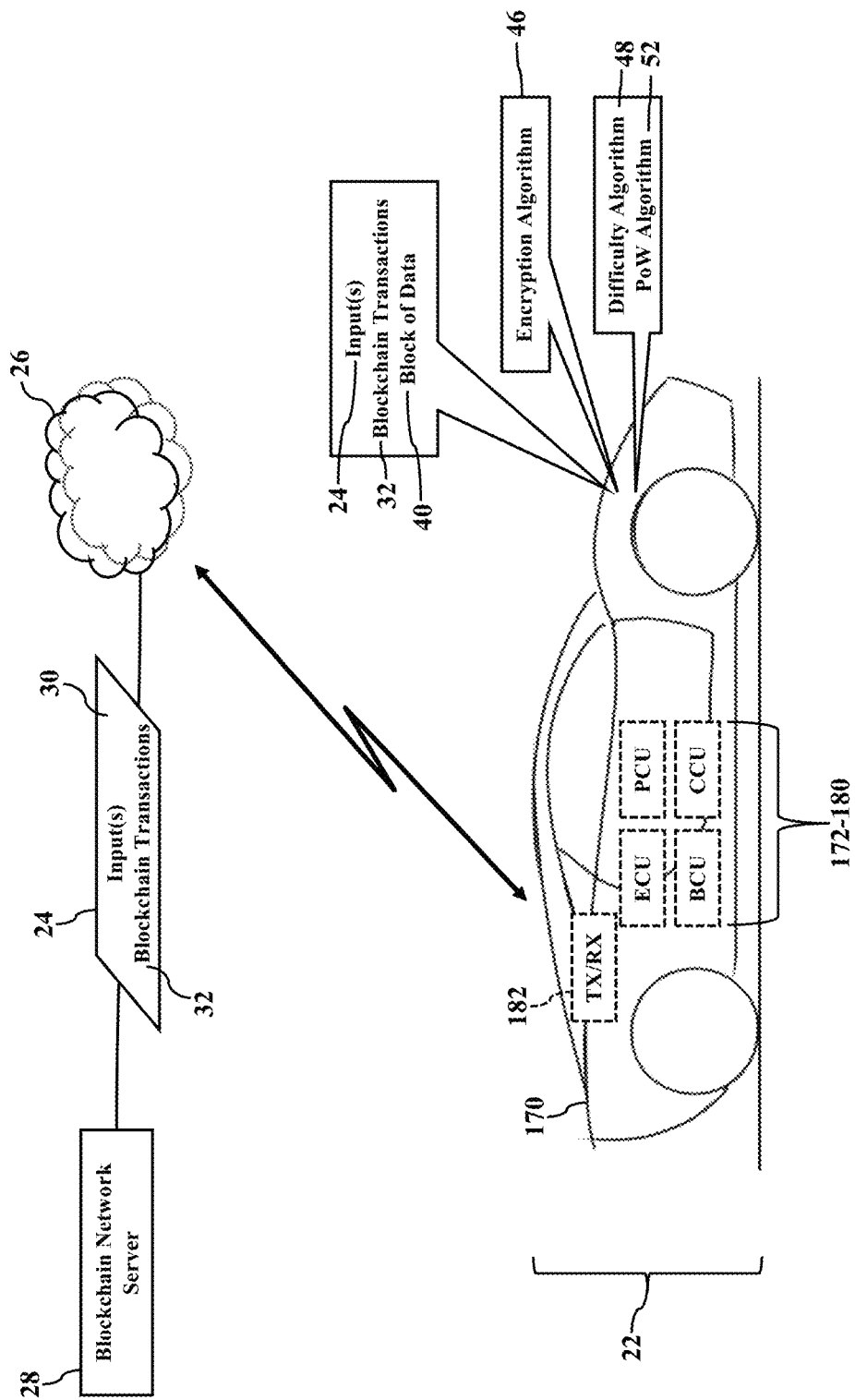

FIG. 19 also illustrates democratic mining. Because exemplary embodiments reduce or even eliminate the need for graphics processors and specialized application-specific integrated circuits, the miner system 22 may even be a car, truck, or other vehicle 170. As the reader may realize, the vehicle 170 may have many electronic systems controlling many components and systems. For example, the engine may have an engine electronic control unit or "ECU" 172, the transmission may have a powertrain electronic control unit or "PCU" 174, the braking system may have a brake electronic control unit or "BCU" 176, and the chassis system may have a chassis electronic control unit or "CUC" 178. There may be many more electronic control units throughout the vehicle 170. A controller area network 180 thus allows all the various electronic control units to communicate with each other (via messages sent/received via a CAN bus). All these controllers may also interface with the communications network 26 via a wireless vehicle transceiver 182 (illustrated as "TX/RX"). The vehicle 170 may thus communicate with the blockchain network server 28 to receive the inputs 24 (such as the blockchain transactions 32). The vehicle 170 may then use the various controllers 172-178 to mine the blockchain transactions 32 using the encryption algorithm 46, the difficulty algorithm 48, and/or the PoW algorithm 52 (as this disclosure above explains). The reader may immediately see that the vehicle 170 is a powerful processing platform for blockchain mining. The vehicle 170 may mine the blockchain transactions 32 when moving or stationary, as long as electrical power is available to the various controllers 172-178 and to the vehicle transceiver 182. Indeed, even when parked with the ignition/battery/systems on or off, exemplary embodiments may maintain the electrical power to mine the blockchain transactions 32. So, a driver/user may configure the vehicle 17 to mine the blockchain transactions 32, even when the vehicle sits during work hours, sleep hours, shopping hours, and other times of idle use. The reader may also immediately see that vehicular mining opens up countless additional possibilities to win the block 40 of data (i.e., solve the puzzle 62) without additional investment in mining rigs. Thousands, millions, or even billions of vehicles 170 (e.g., cars, trucks, boats, planes, buses, trains, motorcycles) may mine the blockchain transactions 32, thus providing a potential windfall to offset the purchasing and operational expenses.

Exemplary embodiments reduce energy consumption. Because a conventional, general purpose central processing unit (e.g., the CPU 36) is adequate for mining the blockchain transactions 32, exemplary embodiments consume much less electrical power. Moreover, because a conventional central processing unit consumes much less electrical power, the CPU operates at much cooler temperatures, generates less waste heat/energy, and therefore requires less cooling, air conditioning, and refrigerant machinery. Exemplary embodiments are thus much cheaper to operate than GPUs and ASICs.

Exemplary embodiments thus democratize blockchain mining. Because encryption, difficulty, and proof-of-work efforts may be functionally divided, general-purpose computer equipment has the processing and memory capability to compete as blockchain miners. For example, because the function(s) that calculate(s) the magnitude of the proof of work (such as the difficulty algorithm 48 and/or the proof-of-work algorithm 52) may be detached or isolated from the function that performs cryptography (such as the hashing algorithm 54), encryption need not be modified in order to improve security (e.g., such as the MONERO® mining scheme). The well-tested SHA-256 hashing function, for example, remains stable and unaffected by difficulty and/or proof-of-work. The difficulty algorithm 48, in other words, need not be determined by or with the hashing algorithm 54. The difficulty algorithm 48, instead, may be separately determined as a true, independent measure of the difficulty 50. The inventor has realized that most or all proof of work schemes generally may have two functions (i.e., one function to do a cryptographic hash and another function to determine the level of difficulty of a given hash). Exemplary embodiments may separate, or take away, what makes proof of work hard from the cryptographic hash and, perhaps instead, put it in the difficulty algorithm 48 that calculates which hash is more difficult. The difficulty algorithm 48, for example, may be functionally combined with the proof-of-work algorithm 52 that calculates the magnitude of the proof of work instead of using the hashing algorithm 54 (as FIG. 5 illustrates). Exemplary embodiments need not try to design, develop, or modify hashing functions that deter ASIC mining.

Encryption may thus be independent from proof-of-work determinations. The proof of work (such as the difficulty algorithm 48 and/or the proof-of-work algorithm 52) may be a different or separate software mechanism from the hashing mechanism. The difficulty 50 of the proof-of-work, for example, may be a separate component from staking in a blockchain. The difficulty algorithm 48 and/or the proof-of-work algorithm 52 may require communications networking between provably different parties. The difficulty algorithm 48 and/or the proof-of-work algorithm 52 may require network delays and/or memory bandwidth limitations. The difficulty algorithm 48 and/or the proof-of-work algorithm 52 may have a random component (such as incorporating a random function), such that the difficulty algorithm 48 and/or the proof-of-work algorithm 52 may randomly to determine the difficulty 50 and/or the proof-of-work result 42. Exemplary embodiments thus reduce or even eliminate the power intensive mechanism that is inherent in today's proof of work schemes by changing how the proof of work is calculated. Exemplary embodiments need not change the hashing algorithm 54, and exemplary embodiments allow a more easily validated proof of work. The hashing algorithm 54 is not bound or required to determine the proof of work. The proof of work need not be cryptographically secure. The liberated, autonomous hashing algorithm 54 generates and guarantees an input (e.g., the hash values 60) that cannot be predicted by some other faster algorithm. The disassociated hashing algorithm 54 effectively generates the hash values 60 as random numbers. The hashing algorithm 54, in other words, provides cryptographic security, so neither the difficulty algorithm 48 nor the proof-of-work algorithm 52 need be cryptographically secure. The difficulty algorithm 48 and/or the proof-of-work algorithm 52 need not be folded into the hashing algorithm 54.

Exemplary embodiments provide great value to blockchains. Exemplary embodiments may functionally separate encryption (e.g., the hashing algorithm 54) from proof of work (such as the difficulty algorithm 48 and/or the proof-of-work algorithm 52). Exemplary embodiments may thus bind proof-of-work to a conventional central processing unit. Deploying a different cryptographic hash is hugely dangerous for blockchains, but deploying another difficulty or proof of work mechanism is not so dangerous. Exemplary embodiments allow blockchains to experiment with different difficulty functions (the difficulty algorithms 48) and/or different proof-of-work algorithms 52 without changing the hashing algorithm 54. Exemplary embodiments thus mitigate risk and reduce problems with cryptographic security. Many blockchain environments would prefer to make their technology CPU mineable for lower power, lower costs, and more democratic participation. The barrier, though, is that conventionally these goals would require changing their hash function. Exemplary embodiments, instead, reduce costs and increase the pool of miner systems without changing the hash function. The difficulty algorithm 48 and/or the proof-of-work algorithm 52 may be refined, modified, or even replaced with little or no impact on the hashing algorithm 54.

Exemplary embodiments reduce electrical power consumption. Blockchain mining is very competitive, as the first miner that solves the mathematical puzzle 62 owns the block 40 of data and is financially rewarded. Large "farms" have thus overtaken blockchain mining, with each miner installation using hundreds or even thousands of ASIC-based computers to improve their chances of first solving the calculations specified by the mathematical puzzle 62. ASIC-based blockchain mining requires tremendous energy resources, though, with some studies estimating that each BITCOIN® transaction consumes more daily electricity than an average American home. Moreover, because ASIC-based blockchain mining operates 24/7/365 at full processing power, the ASIC-based machines quickly wear out or fail and need periodic (perhaps yearly) replacement. Exemplary embodiments, instead, retarget blockchain mining back to CPU-based machines that consume far less electrical power and that cost far less money to purchase. Because the capital costs and expenses are greatly reduced, more miners and more CPU-based machines may effectively participate and compete. The CPU-based machines, in other words, have a realistic and profitable chance of first solving the calculations specified by the mathematical puzzle 62. Democratic participation is greatly increased.

Figure 20:
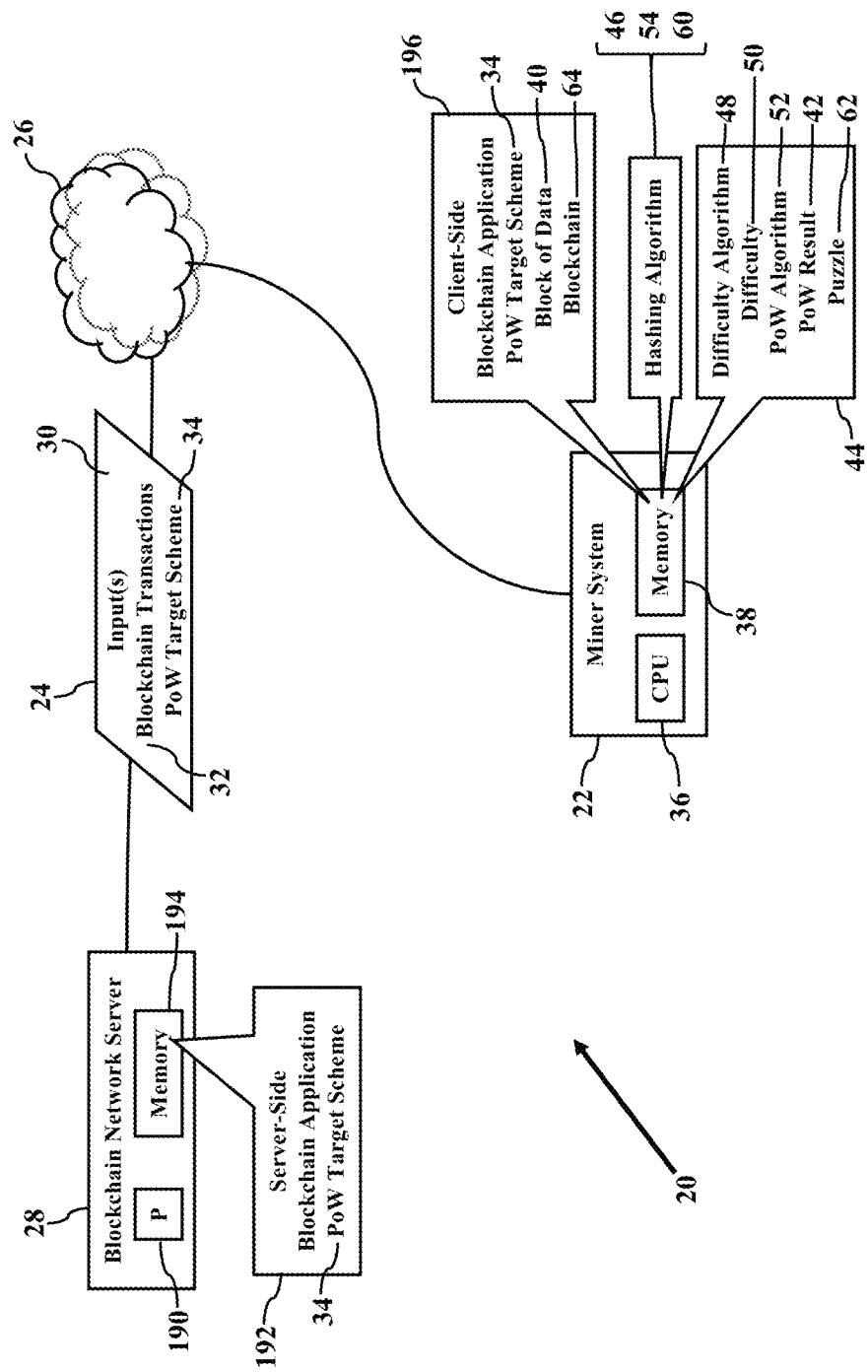
FIGS. 20-21 are more detailed illustrations of an operating environment, according to exemplary embodiments.
Figure 21:
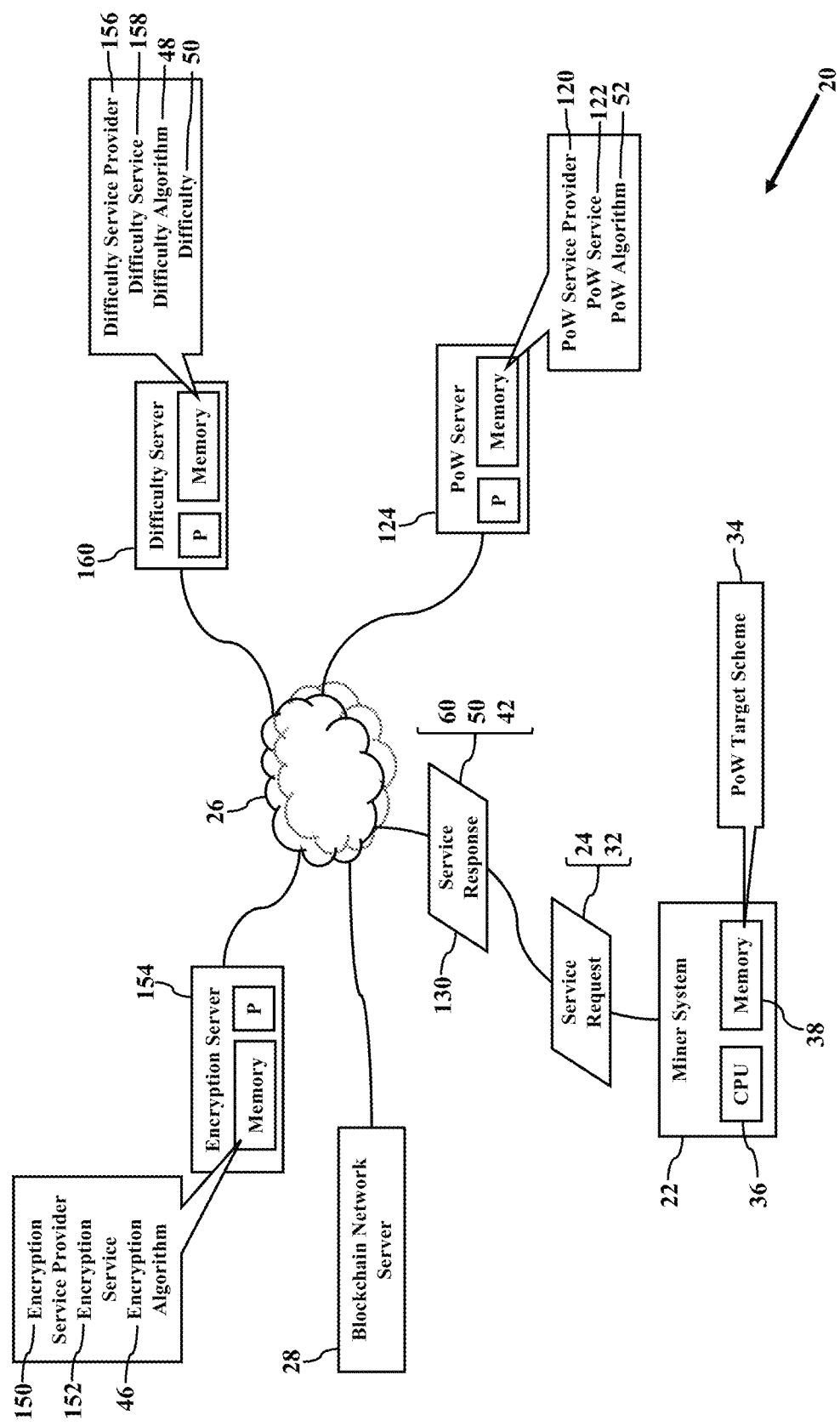
Figure 22:
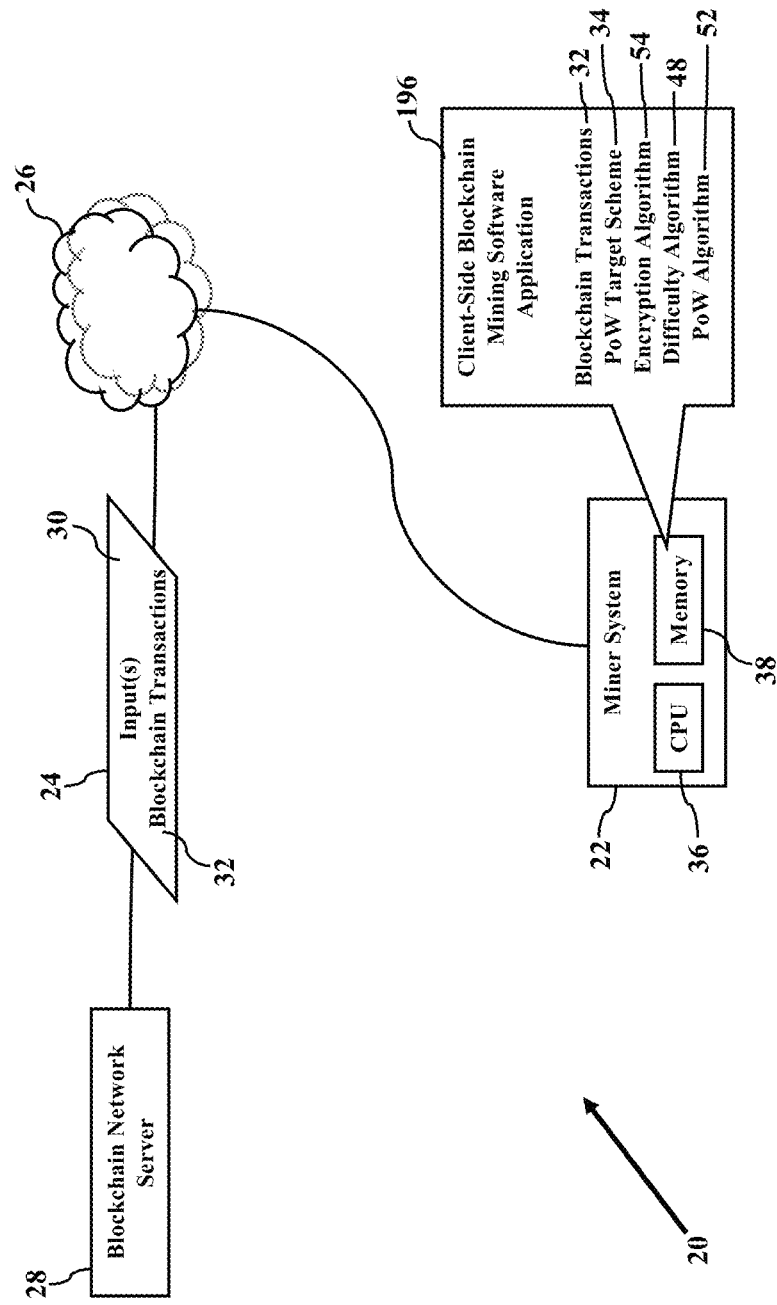
FIGS. 22-31 illustrate mining specifications, according to exemplary embodiments.

FIGS. 20-21 are more detailed illustrations of an operating environment, according to exemplary embodiments. FIG. 20 illustrates the blockchain network server 28 communicating with the miner system 22 via the communications network 26. The blockchain network server 28 and the miner system 22 operate in the blockchain environment 20. The blockchain network server 28 has a hardware processing component 190 (e.g., "P") that executes a server-side blockchain software application 192 stored in a local memory device 194. The blockchain network server 28 has a network interface to the communications network 26, thus allowing two-way, bidirectional communication with the miner system 22. The server-side blockchain software application 192 includes instructions, code, and/or programs that cause the blockchain network server 28 to perform operations, such as sending the inputs 24 (such as the blockchain transactions 32) and/or the proof-of-work ("PoW") target scheme 34 via the communications network 26 to the network address (e.g., Internet protocol address) associated with or assigned to the miner system 22. The inputs 24 may be any electronic data 30 that is shared among miners participating in the blockchain environment 20.

The miner system 22 operates as a mining node in the blockchain environment 20. The miner system 22 has the central processing unit (e.g., "CPU") 36 that executes a client-side blockchain mining software application 196 stored in the local memory device 38. The miner system 22 has a network interface to the communications network 26, thus allowing two-way, bidirectional communication with the blockchain network server 28. The client-side blockchain mining software application 196 includes instructions, code, and/or programs that cause the miner system 22 to perform operations, such as receiving the inputs 24, the electronic data 30, and/or the proof-of-work ("PoW") target scheme 34. The client-side blockchain mining software application 196 may then cause the miner system 22 to execute the proof-of-work ("PoW") mechanism 44 based on the electronic data 30 representing the inputs 24. The client-side blockchain mining software application 196 may instruct the CPU 36 to call and/or to execute the encryption algorithm 46, the difficulty algorithm 48, and/or the PoW algorithm 52. The CPU 36 calls or executes any or all of the encryption algorithm 46, the difficulty algorithm 48, and/or the PoW algorithm 52 using the electronic data 30.

The miner system 22 mines blockchain transactional records. Whatever the electronic data 30 represents, the miner system 22 applies the electronic data 30 according to the proof-of-work target scheme 34. While the proof-of-work target scheme 34 may specify any encryption algorithm 46, most blockchains specify the hashing algorithm 54. The miner system 22 may thus generate the hash values 60 by hashing the electronic data 30 (e.g., the blockchain transactions 32) using the hashing algorithm 54. The miner system 22 may generate the difficulty 50 by executing the difficulty algorithm 48 using the hash values 60. The miner system 22 may generate the proof-of-work result 42 using the hash value(s) 60 as inputs to the proof-of-work algorithm 52. If the proof-of-work result 42 satisfies the mathematical puzzle 62, according to the rules/regulations specified by the blockchain network server 28 and/or the proof-of-work target scheme 34, then perhaps the miner system 22 earns or owns the right or ability to write/record blockchain transaction(s) to the block 40 of data. The miner system 22 may also earn or be rewarded with a compensation (such as a cryptographic coin, points, other currency/coin/money, or other value).

The miner system 22 may own the block 40 of data. If the miner system 22 is the first to satisfy the proof-of-work target scheme 34 (e.g., the proof-of-work result 42 satisfies the mathematical puzzle 62), the miner system 22 earns the sole right or ability to write the blockchain transactions 32 to the block 40 of data. The miner system 22 may timestamp the block 40 of data and broadcast the block 40 of data, the timestamp, the proof-of-work result 42, and/or the mathematical puzzle 62 to other miners in the blockchain environment 20. The miner system 22, may broadcast a hash value representing the block 40 of data. The miner system 22 thus adds or chains the block 40 of data (and perhaps its hash value) to the blockchain 64, and the other miners begin working on a next block in the blockchain 64.

The proof-of-work target scheme 34 and/or the mathematical puzzle 62 may vary. Satoshi's BITCOIN® proof-of-work scanned for a value that, when hashed, the hash value begins with a number of zero bits. The average work required is exponential in the number of zero bits required and can be verified by executing a single hash. BITCOIN's miners may increment a nonce in the block 40 of data until a value is found that gives the block's hash the required zero bits.

FIG. 21 further illustrates the operating environment. The miner system 22 may optionally utilize vendors for any of the hashing algorithm 54, the difficulty algorithm 48, and the proof-of-work algorithm 52. The miner system 22 may enlist or request that a service provider provide or perform a processing service. The encryption server 154, for example, may communicate with the blockchain network server 28 and the miner system 22 via the communications network 26. The encryption server 154 has a hardware processing element ("P") that executes the encryption algorithm 46 stored in a local memory device. The encryption server 154 is operated on behalf of the encryption service provider 150 and provides the encryption service 152. The miner system 22 and/or the blockchain network server 28 may send an encryption service request to the encryption server 154, and the encryption service request may specify the inputs 24 (such as the blockchain transactions 32). The encryption server 154 executes the encryption algorithm 46 using the inputs 24 to generate the hash value(s) 60. The encryption server 154 sends a service response to the miner system 22, and the service response includes or specifies the hash value(s) 60.

Other suppliers may be used. The difficulty server 160 may communicate with the blockchain network server 28 and the miner system 22 via the communications network 26. The difficulty server 160 has a hardware processing element ("P") that executes the difficulty algorithm 48 stored in a local memory device. The difficulty service provider 156 may provide the difficulty service 158 by instructing the difficulty server 160 to execute the difficulty algorithm 48 chosen or specified by the miner system 22 and/or the blockchain network server 28. The miner system 22 and/or the blockchain network server 28 may send a difficulty service request to the difficulty server 160, and the difficulty service request may specify the hash value(s) 60. The difficulty server 160 executes the difficulty algorithm 48 using the hash value(s) 60 to generate the difficulty 50. The difficulty server 160 sends the service response to the miner system 22, and the service response includes or specifies the difficulty 50. The PoW server 124 may communicate with the blockchain network server 28 and the miner system 22 via the communications network 26. The PoW server 124 has a hardware processing element ("P") that executes the proof-of-work algorithm 52 stored in a local memory device. The PoW service provider 120 (e.g., the PoW server 124) may provide the PoW service 122 by executing the proof-of-work algorithm 52 chosen or specified by the miner system 22 and/or the blockchain network server 28. The PoW server 124 sends the service response to the miner system 22, and the service response includes or specifies the PoW result 42. The miner system 22 may compare any of the hash value(s) 60, the difficulty 50, and/or the PoW result 42 to the proof-of-work target scheme 34. If the proof-of-work target scheme 34 is satisfied, perhaps the miner system 22 is the first miner to have solved the puzzle 62.

Exemplary embodiments may be applied regardless of networking environment. Exemplary embodiments may be easily adapted to stationary or mobile devices having wide-area networking (e.g., 4G/LTE/5G cellular), wireless local area networking (WI-FI®), near field, and/or BLUETOOTH capability. Exemplary embodiments may be applied to stationary or mobile devices utilizing any portion of the electromagnetic spectrum and any signaling standard (such as the IEEE 802 family of standards, GSM/CDMA/TDMA or any cellular standard, and/or the ISM band). Exemplary embodiments, however, may be applied to any processor-controlled device operating in the radio-frequency domain and/or the Internet Protocol (IP) domain. Exemplary embodiments may be applied to any processor-controlled device utilizing a distributed computing network, such as the Internet (sometimes alternatively known as the "World Wide Web"), an intranet, a local-area network (LAN), and/or a wide-area network (WAN). Exemplary embodiments may be applied to any processor-controlled device utilizing power line technologies, in which signals are communicated via electrical wiring. Indeed, exemplary embodiments may be applied regardless of physical componentry, physical configuration, or communications standard(s).

Exemplary embodiments may utilize any processing component, configuration, or system. For example, the miner system 22 may utilize any desktop, mobile, or server central processing unit or chipset offered by INTEL®, ADVANCED MICRO DEVICES®, ARM®, TAIWAN SEMICONDUCTOR MANUFACTURING®, QUALCOMM®, or any other manufacturer. The miner system 22 may even use multiple central processing units or chipsets, which could include distributed processors or parallel processors in a single machine or multiple machines. The central processing unit or chipset can be used in supporting a virtual processing environment. The central processing unit or chipset could include a state machine or logic controller. When any of the central processing units or chipsets execute instructions to perform "operations," this could include the central processing unit or chipset performing the operations directly and/or facilitating, directing, or cooperating with another device or component to perform the operations.

Exemplary embodiments may packetize. When the blockchain network server 28 and the miner system 22 communicate via the communications network 26, the blockchain network server 28 and the miner system 22 may collect, send, and retrieve information. The information may be formatted or generated as packets of data according to a packet protocol (such as the Internet Protocol). The packets of data contain bits or bytes of data describing the contents, or payload, of a message. A header of each packet of data may be read or inspected and contain routing information identifying an origination address and/or a destination address.

Exemplary embodiments may use any encryption or hashing function. There are many encryption algorithms and schemes, and exemplary embodiments may be adapted to execute or to conform to any encryption algorithm and/or scheme. In the blockchain environment 20, though, many readers may be familiar with the various hashing algorithms, especially the well-known SHA-256 hashing algorithm. The SHA-256 hashing algorithm acts on any electronic data or information to generate a 256-bit hash value as a cryptographic key. The key is thus a unique digital signature. However, there are many different hashing algorithms, and exemplary embodiments may be adapted to execute or to conform to any hashing algorithm, hashing family, and/or hashing scheme (e.g., Blake family, MD family, RIPE family, SHA family, CRC family).

The miner system 22 may store or request different software packages. The hashing algorithm 54 may be a software file, executable program, routine, module, programming code, or third-party service that hashes the blockchain transactions 32 to generate the hash value(s) 60. The difficulty algorithm 48 may be a software file, executable program, routine, module, programming code, or third-party service that uses the hash value(s) 60 to generate the difficulty 50. The proof-of-work ("PoW") algorithm 52 be a software file, executable program, routine, module, programming code, or third-party service that uses the hash value(s) 60 to generate the PoW result 42. The miner system 22 may download or otherwise acquire the hashing algorithm 54, the difficulty algorithm 48, and/or the PoW algorithm 52 to provide mining operations for the blockchain transactions 32.

The blockchain environment 20 may flexibly switch or interchange encryption, difficulty, and proof-of-work. Because the hashing algorithm 54, the difficulty algorithm 48, and the proof-of-work algorithm 52 may be separate software packages, the proof-of-work ("PoW") target scheme 34 and/or the blockchain environment 20 may mix-and-match the encryption algorithm 46, the difficulty algorithm 48, and the proof-of-work algorithm 52. The blockchain environment 20 may thus easily evaluate different combinations of the encryption algorithm 46, the difficulty algorithm 48, and the proof-of-work algorithm 52 with little or no intra-algorithm or intra-application effect. The blockchain environment 20 may mix-and-match encryption, difficulty, and proof-of-work.

FIGS. 22-31 illustrate mining specifications, according to exemplary embodiments. When the miner system 22 communicates with the blockchain network server 28, the blockchain network server 28 may specify the proof-of-work ("PoW") target scheme 34 that is required by the blockchain environment 20. That is, when the miner system 22 participates as a miner and mines or processes blockchain records/transactions, the miner system 22 may be required or instructed to use the particular hashing algorithm 54, the difficulty algorithm 48, and/or the proof-of-work algorithm 52 specified by the blockchain network. For example, in order for the miner system 22 to be authorized or recognized as a mining participant, the miner system 22 may be required to download the client-side blockchain mining software application 196 that specifies or includes the hashing algorithm 54, the difficulty algorithm 48, and/or the proof-of-work algorithm 52. The client-side blockchain mining software application 196 may thus comprise any software apps or modules, files, programming code, or instructions representing the hashing algorithm 54, the difficulty algorithm 48, and/or the proof-of-work algorithm 52.

Figure 23:
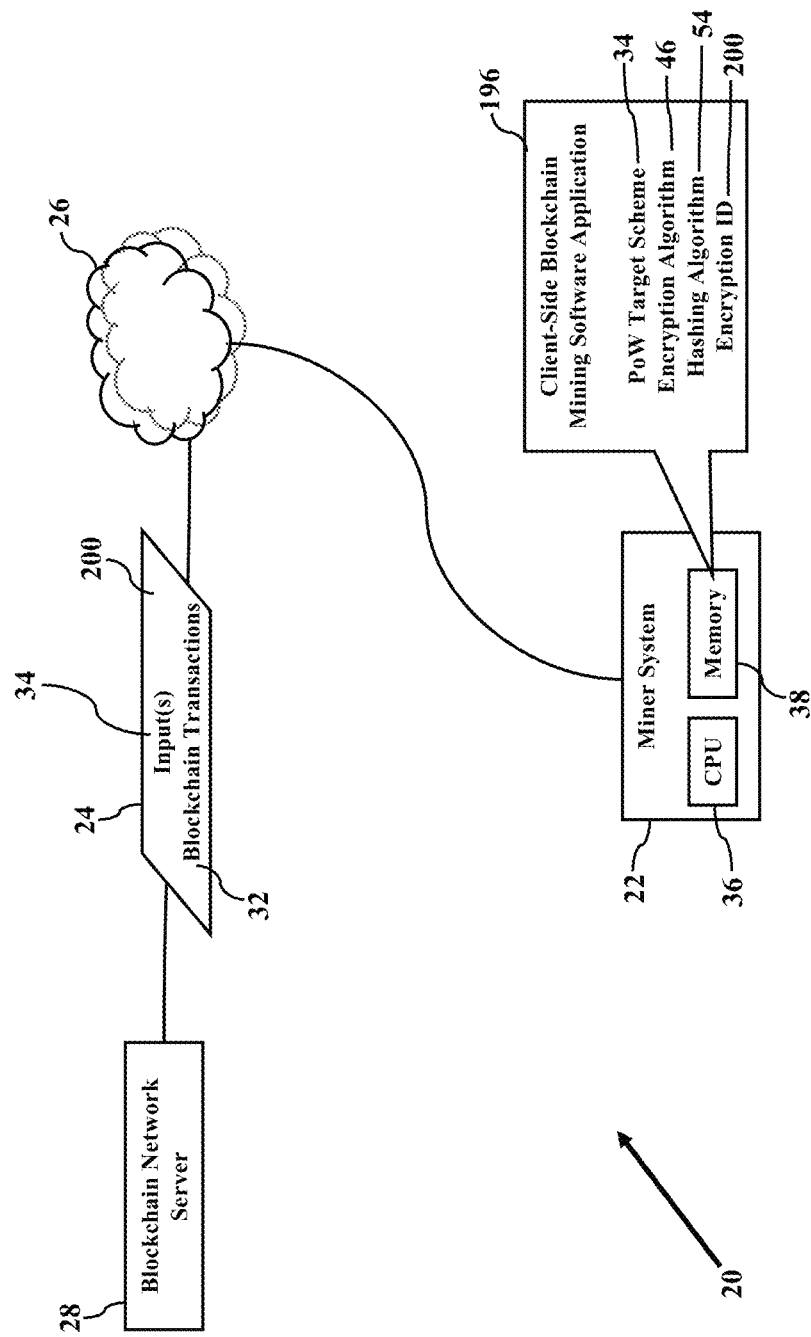
Figure 24:
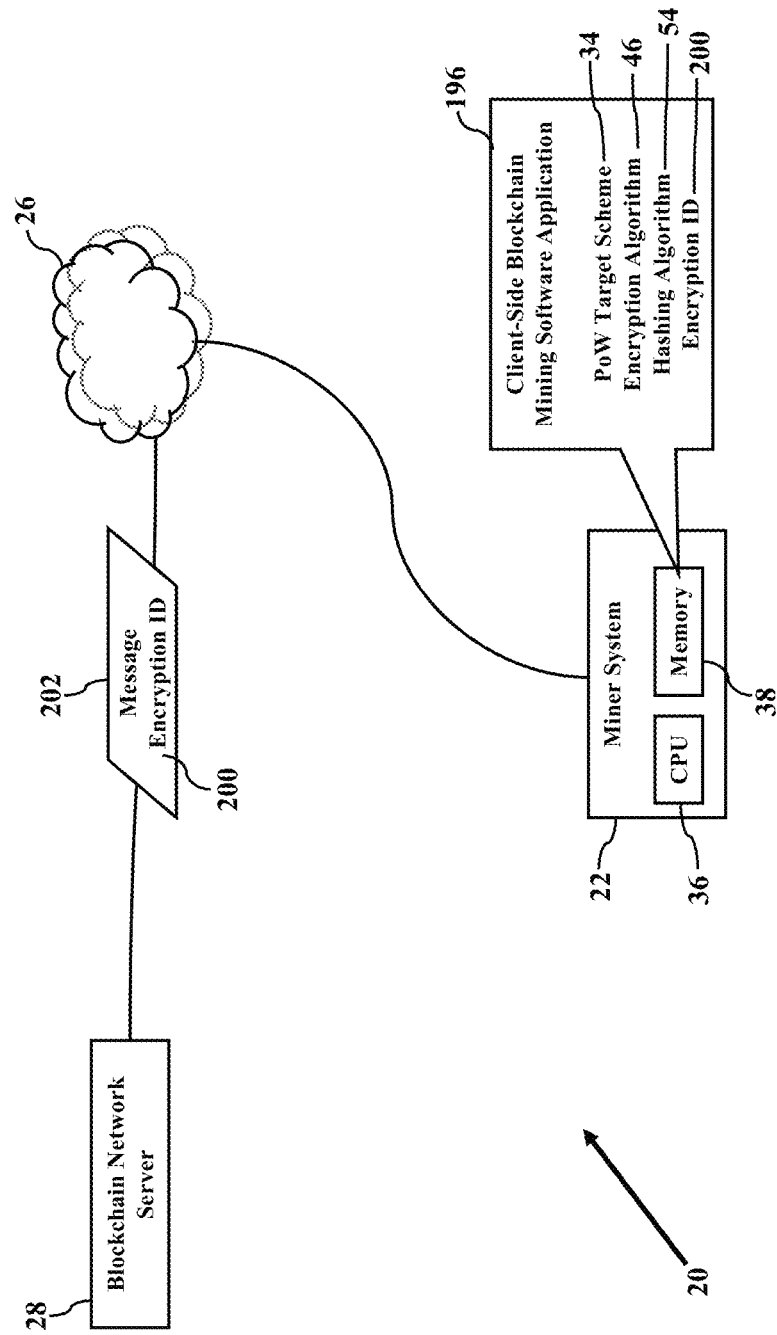
Figure 25:
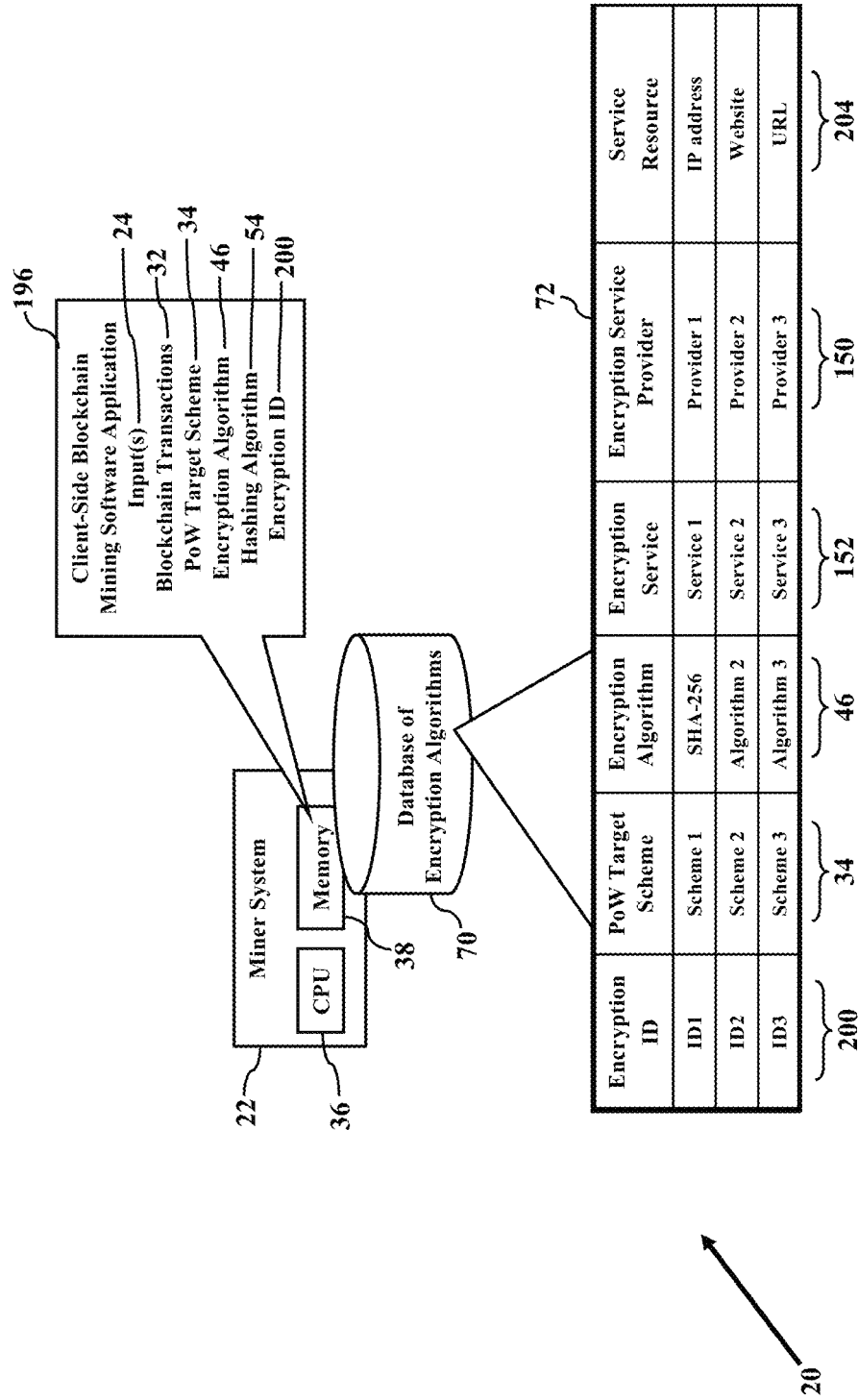

FIGS. 23-25 illustrate an encryption identifier mechanism. FIG. 23 illustrates the miner system 22 receiving the proof-of-work ("PoW") target scheme 34 that is required by the blockchain environment 20. In order to reduce a memory byte size and/or programming line size of the PoW target scheme 34 and/or the client-side blockchain mining software application 196, exemplary embodiments may specify an encryption identifier (encryption "ID") 200 associated with the blockchain network's chosen or required encryption scheme. The encryption identifier 200 may be any alphanumeric combination, hash value, network address, website, or other data/information that uniquely identifies the PoW target scheme 34 and/or the encryption algorithm 46 used by the blockchain environment 20. As FIG. 23 illustrates, the miner system 22 may receive the encryption identifier 200 as a specification or parameter associated with the PoW target scheme 34 and/or the encryption algorithm 46. As FIG. 24 illustrates, though, the miner system 22 may receive a packetized message 202 from the blockchain network server 28, and a packet header and/or payload may specify or include the encryption identifier 200 as a data field, specification, or parameter. Again, because many or most blockchain networks use hashing as an encryption mechanism, the encryption identifier 200 may specify, be assigned to, or be associated with the hashing algorithm 54. The blockchain network server 28 may thus send the encryption identifier 200 (via the communications network 26) to the miner system 22. The encryption identifier 200 may be packaged as a downloadable component, parameter, or value with the client-side blockchain mining software application 196. However, the encryption identifier 200 may additionally or alternatively be sent to the miner system 22 at any time via the message 202. Because the encryption identifier 200 may be separately sent from the client-side blockchain mining software application 196, the encryption identifier 200 may be dynamically updated or changed without downloading a new or updated client-side blockchain mining software application 196.

As FIG. 25 illustrates, exemplary embodiments may consult the electronic database 70 of encryption algorithms. Once the miner system 22 receives or determines the encryption identifier 200, the miner system 22 may implement the encryption scheme represented by the encryption identifier 200. The miner system 22 may obtain, read, or retrieve the encryption identifier 200 specified by the client-side blockchain mining software application 196 and/or packet inspect the message 202 from the blockchain network server 28. Once the encryption identifier 200 is determined, the miner system 22 may identify the corresponding blockchain encryption scheme by querying the electronic database 70 of encryption algorithms for the encryption identifier 200. FIG. 25 illustrates the electronic database 70 of encryption algorithms locally stored in the memory device 38 of the miner system 22. The electronic database 70 of encryption algorithms may store, reference, or associate the encryption identifier 200 to its corresponding proof-of-work target scheme 34 and/or encryption algorithm 46. The miner system 22 may thus perform or execute a database lookup for the encryption identifier 200 to identify which proof-of-work target scheme 34 and/or encryption algorithm 46 is required for miners operating in the blockchain environment 20. The miner system 22 may then retrieve, call, and/or execute the encryption algorithm 46 using the inputs 24 (such as the blockchain transactions 32), as this disclosure above explained (with reference to FIG. 7).

Exemplary embodiments may outsource encryption operations. When the miner system 22 determines the encryption identifier 200, the corresponding blockchain encryption scheme may require or specify the encryption service provider 150 that provides the encryption service 152. As FIG. 25 also illustrates, the electronic database 70 of encryption algorithms may map or relate the encryption identifier 200 to its corresponding encryption service provider 150 that provides the encryption service 152. The miner system 22 may thus identify an encryption service resource 204 that provides the encryption service 152. The encryption service resource 204, for example, may be an Internet protocol address, website/webpage, and/or uniform resource locator (URL) that is assigned to, or associated with, the encryption service provider 150 and/or the encryption service 152. The miner system 22 may outsource or subcontract the inputs 24 (such as the blockchain transactions 32) to the encryption service resource 204 (perhaps using the service request and service response mechanism explained with reference to FIG. 21).

Exemplary embodiments may thus be agnostic to hashing. The miner system 22 may call, request, and/or execute any encryption scheme specified by any client, cryptographic coin, or blockchain network. The miner system 22 may dynamically switch or mix-and-match different encryption schemes. Once the miner system 22 determines the proof-of-work target scheme 34, the encryption algorithm 46, the encryption service provider 150, the encryption service 152, the encryption identifier 200, and/or the encryption service resource 204, the miner system 22 may perform any encryption scheme specified for the blockchain environment 20. The blockchain environment 20 may dynamically change the encryption scheme at any time. The blockchain environment 20 may flexibly switch, change, and evaluate different encryption strategies, perhaps with little or no impact or effect on difficulty and proof-of-work operations. Moreover, the miner system 22 may operate within or mine different blockchain environments 20 without specialized hardware rigs.

Exemplary embodiments improve computer functioning. Because exemplary embodiments may only specify the encryption identifier 200, the memory byte size consumed by the proof-of-work ("PoW") target scheme 34 and/or the client-side blockchain mining software application 196 is reduced. That is, the blockchain network server 28 need not send the entire software program, code, or instructions representing the hashing algorithm 54 used by the blockchain environment 20. The blockchain environment 20, the blockchain network server 28, and/or the proof-of-work ("PoW") target scheme 34 need only specify much smaller byte-sized data or information representing the encryption algorithm 46, the encryption service provider 150, the encryption service 152, the encryption identifier 200, and/or the encryption service resource 204. The blockchain environment 20 need not be burdened with conveying the hashing algorithm 54 to the miner system 22 and other mining nodes. The blockchain environment 20 and the communications network 26 convey less packet traffic, so packet travel times and network latency are reduced. Moreover, especially if the miner system 22 outsources the hashing operation, the miner system 22 is relieved from processing/executing the hashing algorithm 54 and consumes less of the electrical power. Again, then, a faster and more expensive graphics processor or even ASIC will not speed up the hashing operation. The conventional central processing unit 36 is adequate, reduces costs, and promotes democratic mining.

Figure 26:
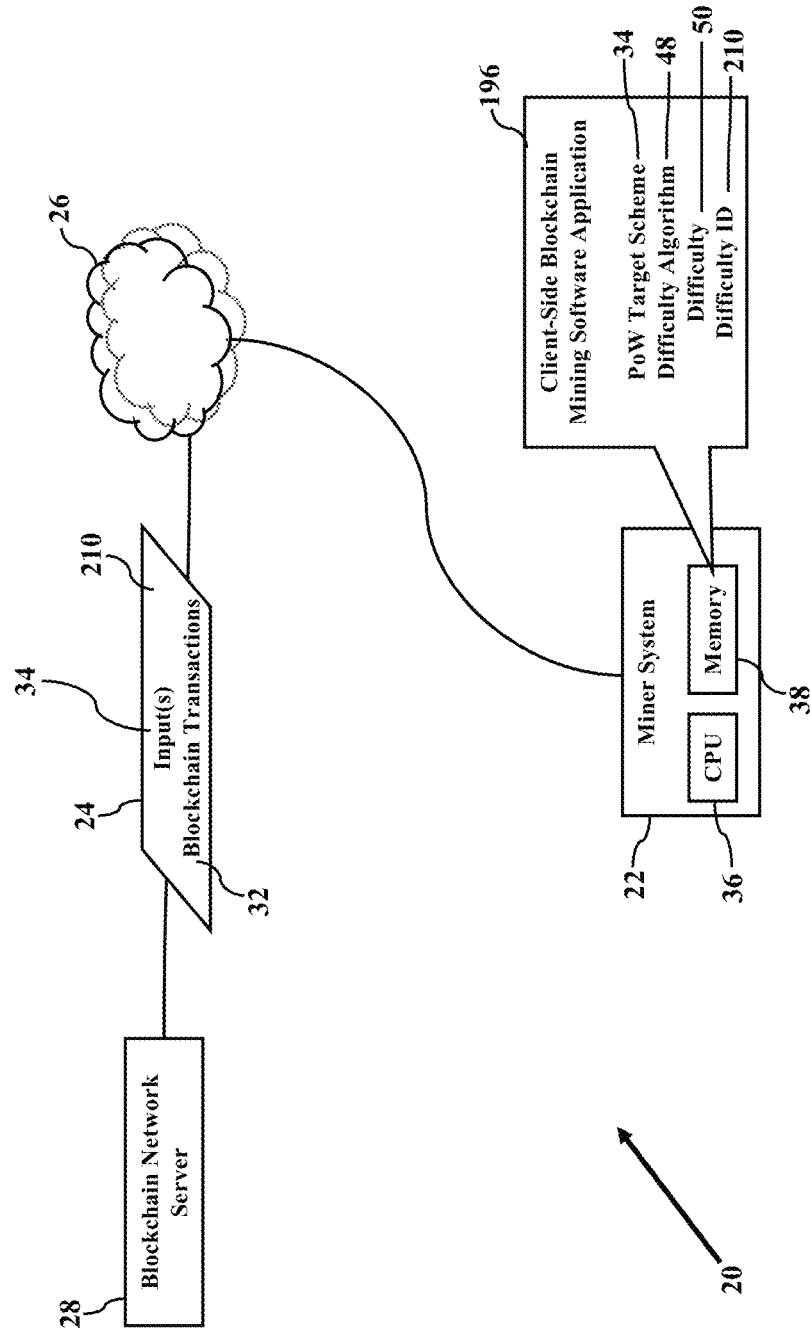
Figure 27:
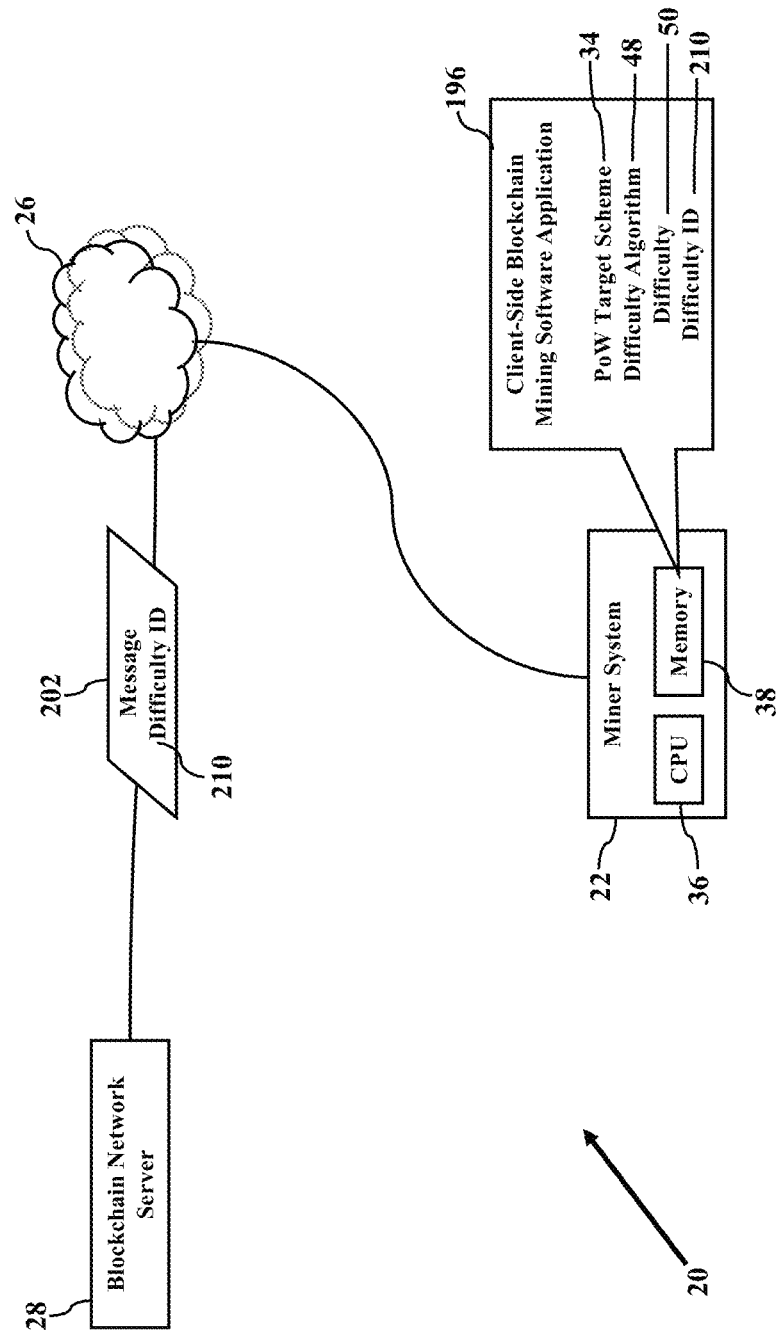
Figure 28:
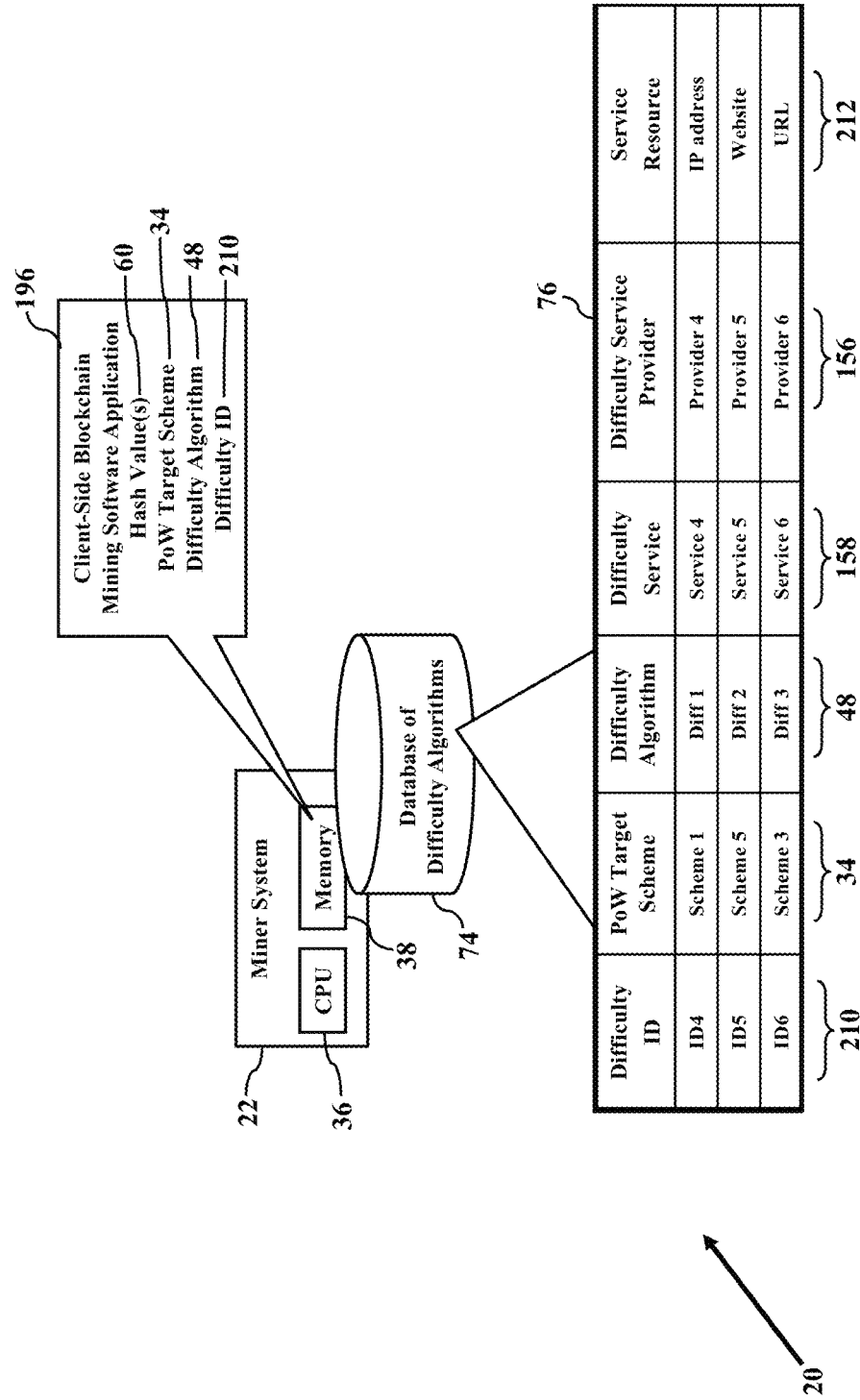

FIGS. 26-28 illustrate illustrates a difficulty identifier mechanism. FIG. 26 illustrates the miner system 22 receiving the proof-of-work ("PoW") target scheme 34 that is required by the blockchain environment 20. In order to reduce a memory byte size and/or programming line size of the PoW target scheme 34 and/or the client-side blockchain mining software application 196, exemplary embodiments may specify a difficulty identifier (difficulty "ID") 210 associated with the blockchain network's chosen or required difficulty scheme. The difficulty identifier 210 may be any alphanumeric combination, hash value, network address, website, or other data/information that uniquely identifies the PoW target scheme 34 and/or the difficulty algorithm 48 used by the blockchain environment 20. As FIG. 26 illustrates, the miner system 22 may receive the difficulty identifier 210 as a specification or parameter associated with the PoW target scheme 34 and/or the difficulty algorithm 48. As FIG. 27 illustrates, though, the miner system 22 may receive the packetized message 202 from the blockchain network server 28, and a packet header and/or payload may specify or include the difficulty identifier 210 as a data field, specification, or parameter. The blockchain network server 28 may thus send the difficulty identifier 210 (via the communications network 26) to the miner system 22. The difficulty identifier 210 may be packaged as a downloadable component, parameter, or value with the client-side blockchain mining software application 196. However, the difficulty identifier 210 may additionally or alternatively be sent to the miner system 22 at any time via the message 202. Because the difficulty identifier 210 may be separately sent from the client-side blockchain mining software application 196, the difficulty identifier 210 may be dynamically updated or changed without downloading a new or updated client-side blockchain mining software application 196.

As FIG. 28 illustrates, exemplary embodiments may consult the electronic database 74 of difficulty algorithms. Once the miner system 22 receives or determines the difficulty identifier 210, the miner system 22 may implement the difficulty scheme represented by the difficulty identifier 210. The miner system 22 may obtain, read, or retrieve the difficulty identifier 210 specified by the client-side blockchain mining software application 196 and/or packet inspect the message 202 from the blockchain network server 28. Once the difficulty identifier 210 is determined, the miner system 22 may identify the corresponding blockchain difficulty scheme by querying the electronic database 74 of difficulty algorithms for any query parameter (such as the difficulty identifier 210). FIG. 28 illustrates the electronic database 74 of difficulty algorithms locally stored in the memory device 38 of the miner system 22. The electronic database 74 of difficulty algorithms may store, reference, or associate the difficulty identifier 210 to its corresponding proof-of-work target scheme 34 and/or difficulty algorithm 48. The miner system 22 may thus perform or execute a database lookup for the difficulty identifier 210 to identify which proof-of-work target scheme 34 and/or difficulty algorithm 48 is required for miners operating in the blockchain environment 20. The miner system 22 may then retrieve, call, and/or execute the difficulty algorithm 48 using the hash value(s) 60, as this disclosure above explained (with reference to FIG. 8).

Exemplary embodiments may outsource difficulty operations. When the miner system 22 determines the difficulty identifier 210, the corresponding blockchain difficulty scheme may require or specify the difficulty service provider 156 that provides the difficulty service 158. As FIG. 28 also illustrates, the electronic database 74 of difficulty algorithms may map or relate the difficulty identifier 210 to its corresponding difficulty service provider 156 that provides the difficulty service 158. The miner system 22 may thus identify a difficulty service resource 212 that provides the difficulty service 158. The difficulty service resource 212, for example, may be an Internet protocol address, website/webpage, and/or uniform resource locator (URL) that is assigned to, or associated with, the difficulty service provider 156 and/or the difficulty service 158. The miner system 22 may outsource or subcontract the hash value(s) 60 to the difficulty service resource 212 (perhaps using the service request and service response mechanism explained with reference to FIG. 21).

Exemplary embodiments may thus be agnostic to difficulty. The miner system 22 may call, request, and/or execute any difficulty scheme specified by any client, cryptographic coin, or blockchain network. The miner system 22 may dynamically switch or mix-and-match different difficulty schemes. Once the miner system 22 determines the proof-of-work target scheme 34, the difficulty algorithm 48, the difficulty service provider 156, the difficulty service 158, the difficulty identifier 210, and/or the difficulty service resource 212, the miner system 22 may perform any difficulty scheme specified for the blockchain environment 20. The blockchain environment 20 may dynamically change the difficulty scheme at any time. The blockchain environment 20 may flexibly switch, change, and evaluate different difficulty strategies, perhaps with little or no impact or effect on hashing and proof-of-work operations. Moreover, the miner system 22 may operate within or mine different blockchain environments 20 without specialized hardware rigs.

Exemplary embodiments improve computer functioning. Because exemplary embodiments may only specify the difficulty identifier 210, the memory byte size consumed by the proof-of-work ("PoW") target scheme 34 and/or the client-side blockchain mining software application 196 is reduced. That is, the blockchain network server 28 need not send the entire software program, code, or instructions representing the difficulty algorithm 48 used by the blockchain environment 20. The blockchain environment 20, the blockchain network server 28, and/or the proof-of-work ("PoW") target scheme 34 need only specify much smaller byte-sized data or information representing the difficulty algorithm 48, the difficulty service provider 156, the difficulty service 158, the difficulty identifier 210, and/or the difficulty service resource 212. The blockchain environment 20 need not be burdened with conveying the difficulty algorithm 48 to the miner system 22 and other mining nodes. The blockchain environment 20 and the communications network 26 convey less packet traffic, so packet travel times and network latency are reduced. Moreover, especially if the miner system 22 outsources the difficulty operation, the miner system 22 is relieved from processing/executing the difficulty algorithm 48 and consumes less of the electrical power. Again, then, a faster and more expensive graphics processor or even ASIC will not speed up the difficulty operation. The conventional central processing unit 36 is adequate, reduces costs, and promotes democratic mining.

Figure 29:
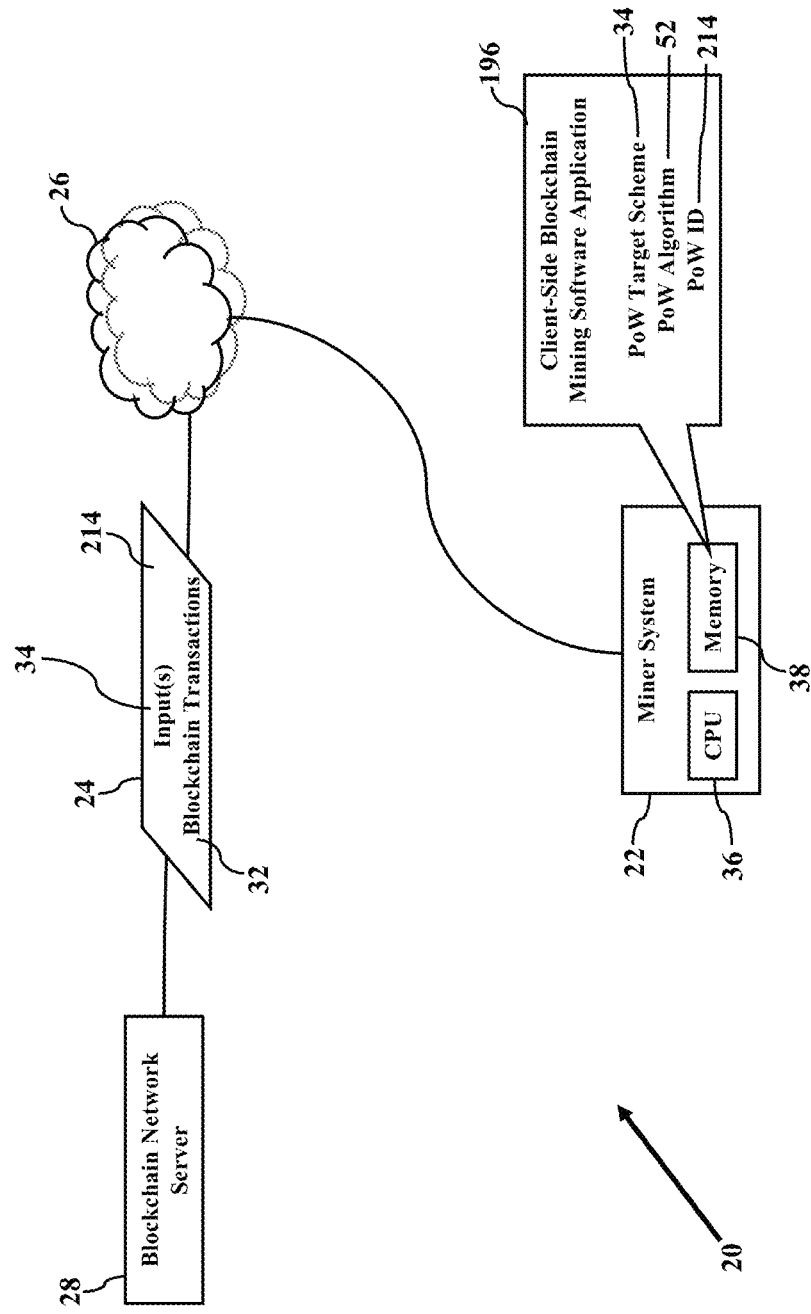
Figure 30:
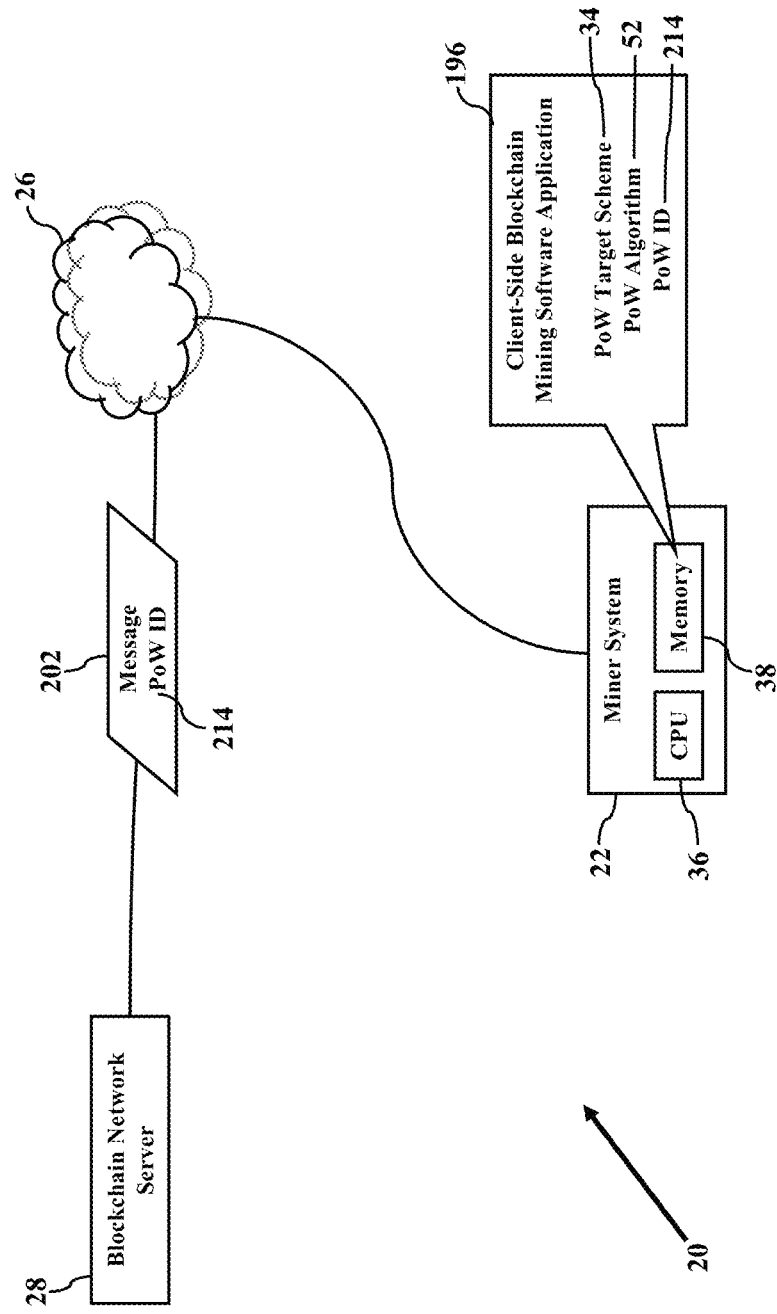
Figure 31:
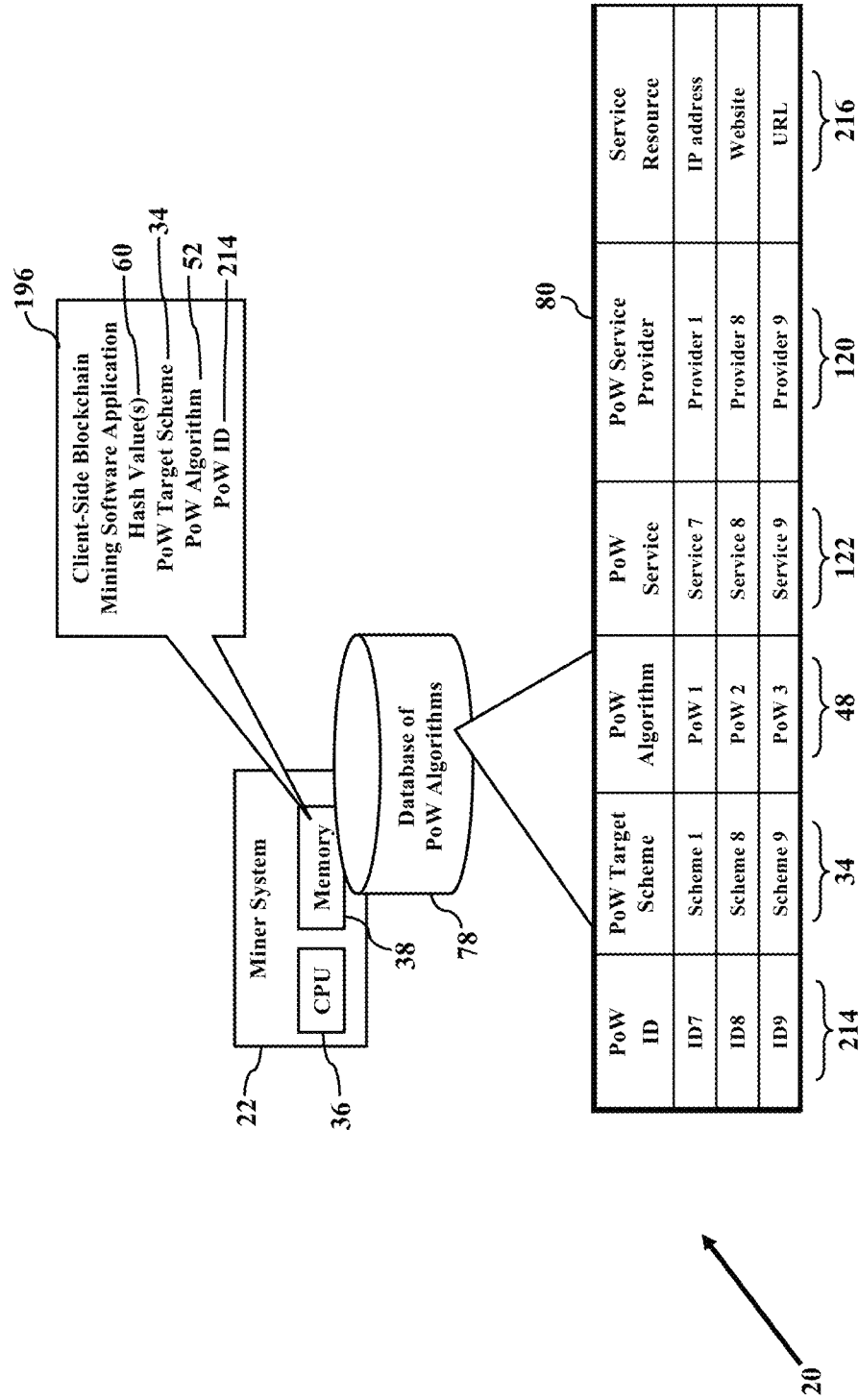

FIGS. 29-31 illustrate illustrates a proof-of-work ("PoW") identifier mechanism. FIG. 29 illustrates the miner system 22 receiving the proof-of-work ("PoW") target scheme 34 that is required by the blockchain environment 20. In order to reduce a memory byte size and/or programming line size of the PoW target scheme 34 and/or the client-side blockchain mining software application 196, exemplary embodiments may specify a PoW identifier 214 associated with the blockchain network's chosen or required PoW scheme. The PoW identifier 214 may be any alphanumeric combination, hash value, network address, website, or other data/information that uniquely identifies the PoW target scheme 34 and/or the PoW algorithm 52 used by the blockchain environment 20. As FIG. 29 illustrates, the miner system 22 may receive the PoW identifier 214 as a specification or parameter associated with the PoW target scheme 34 and/or the PoW algorithm 52. As FIG. 30 illustrates, though, the miner system 22 may receive the packetized message 202 from the blockchain network server 28, and a packet header and/or payload may specify or include the PoW identifier 214 as a data field, specification, or parameter. The blockchain network server 28 may thus send the PoW identifier 214 (via the communications network 26) to the miner system 22. The PoW identifier 214 may be packaged as a downloadable component, parameter, or value with the client-side blockchain mining software application 196. However, the PoW identifier 214 may additionally or alternatively be sent to the miner system 22 at any time via the message 202. Because the PoW identifier 214 may be separately sent from the client-side blockchain mining software application 196, the PoW identifier 214 may be dynamically updated or changed without downloading a new or updated client-side blockchain mining software application 196.

As FIG. 31 illustrates, exemplary embodiments may consult the electronic database 78 of PoW algorithms. Once the miner system 22 receives or determines the PoW identifier 214, the miner system 22 may implement the proof-of-work scheme represented by the PoW identifier 214. The miner system 22 may obtain, read, or retrieve the PoW identifier 214 specified by the client-side blockchain mining software application 196 and/or packet inspect the message 202 from the blockchain network server 28. Once the PoW identifier 214 is determined, the miner system 22 may identify the corresponding blockchain proof-of-work scheme by querying the electronic database 78 of PoW algorithms for any query parameter (such as the PoW identifier 214). FIG. 31 illustrates the database 78 of PoW algorithms locally stored in the memory device 38 of the miner system 22. The electronic database 78 of PoW algorithms may store, reference, or associate the PoW identifier 214 to its corresponding proof-of-work target scheme 34 and/or difficulty algorithm 48. The miner system 22 may thus perform or execute a database lookup for the PoW identifier 214 to identify which proof-of-work target scheme 34 and/or PoW algorithm 52 is required for miners operating in the blockchain environment 20. The miner system 22 may then retrieve, call, and/or execute the PoW algorithm 52 using the hash value(s) 60, as this disclosure above explained (with reference to FIG. 9).

Exemplary embodiments may outsource difficulty operations. When the miner system 22 determines the PoW identifier 214, the corresponding blockchain proof-of-work scheme may require or specify the PoW service provider 120 that provides the PoW service 122. As FIG. 31 also illustrates, the electronic database 78 of PoW algorithms may map or relate the PoW identifier 214 to its corresponding PoW service provider 120 and PoW service 122. The miner system 22 may thus identify a PoW service resource 216 that provides the PoW service 122. The PoW service resource 216, for example, may be an Internet protocol address, website/webpage, and/or uniform resource locator (URL) that is assigned to, or associated with, the PoW service provider 120 and/or PoW service 122. The miner system 22 may outsource or subcontract the hash value(s) 60 to the PoW service resource 216 (perhaps using the service request and service response mechanism explained with reference to FIG. 21).

Exemplary embodiments may thus be agnostic to proof-of-work. The miner system 22 may call, request, and/or execute any proof-of-work scheme specified by any client, cryptographic coin, or blockchain network. The miner system 22 may dynamically switch or mix-and-match different proof-of-work schemes. Once the miner system 22 determines the proof-of-work target scheme 34, the PoW algorithm 52, the PoW service provider 120, the PoW service 122, the PoW identifier 214, and/or the PoW service resource 216, the miner system 22 may perform any proof-of-work scheme specified for the blockchain environment 20. The blockchain environment 20 may dynamically change the proof-of-work scheme at any time. The blockchain environment 20 may flexibly switch, change, and evaluate different proof-of-work strategies, perhaps with little or no impact or effect on hashing and difficulty operations. Moreover, the miner system 22 may operate within or mine different blockchain environments 20 without specialized hardware rigs.

Exemplary embodiments improve computer functioning. Because exemplary embodiments may only specify the PoW identifier 214, the memory byte size consumed by the proof-of-work ("PoW") target scheme 34 and/or the client-side blockchain mining software application 196 is reduced. That is, the blockchain network server 28 need not send the entire software program, code, or instructions representing the PoW algorithm 52 used by the blockchain environment 20. The blockchain environment 20, the blockchain network server 28, and/or the proof-of-work ("PoW") target scheme 34 need only specify much smaller byte-sized data or information representing the PoW algorithm 52, the PoW service provider 120, the PoW service 122, the PoW identifier 214, and/or the PoW service resource 216. The blockchain environment 20 need not be burdened with conveying the PoW algorithm 52 to the miner system 22 and other mining nodes. The blockchain environment 20 and the communications network 26 convey less packet traffic, so packet travel times and network latency are reduced. Moreover, especially if the miner system 22 outsources the proof-of-work operation, the miner system 22 is relieved from processing/executing the PoW algorithm 52 and consumes less of the electrical power. Again, then, a faster and more expensive graphics processor or even ASIC will not speed up the difficulty operation. The conventional central processing unit 36 is adequate, reduces costs, and promotes democratic mining.

Figure 32:
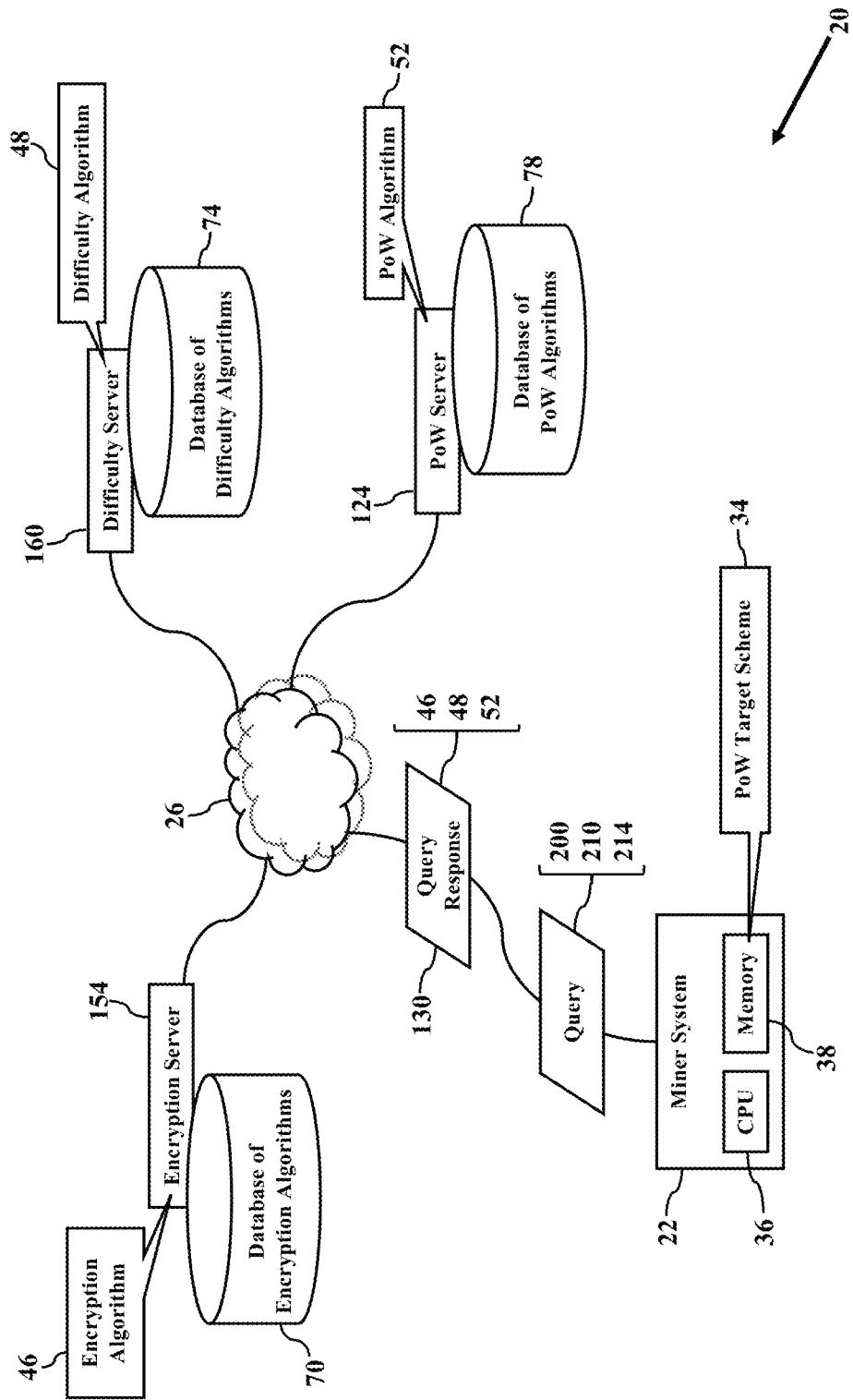
FIG. 32 illustrates remote retrieval, according to exemplary embodiments.

FIG. 32 illustrates remote retrieval, according to exemplary embodiments. After the miner system 22 determines the proof-of-work ("PoW") target scheme 34 that is required by the blockchain environment 20, the miner system 22 may acquire or download the encryption algorithm 46, the difficulty algorithm 48, and/or the PoW algorithm 52. For example, the miner system 22 may determine the encryption identifier 200 (as this disclosure above explains) and send a query to the encryption server 154. The query specifies the encryption identifier 200. When the encryption server 154 receives the query, the encryption server 154 may query the database 70 of encryption algorithms for the encryption identifier 200. The encryption server 154 may locally store the database 70 of encryption algorithms and function as a networked encryption resource for clients. The encryption server 154 identifies and/or retrieves the corresponding encryption algorithm 46. The encryption server 154 sends a query response to the miner system 22, and the query response specifies or includes the corresponding encryption algorithm 46. The miner system 22 may then execute the encryption algorithm 46, as above explained.

The miner system 22 may remotely retrieve the difficulty algorithm 48. After the miner system 22 determines the proof-of-work ("PoW") target scheme 34 that is required by the blockchain environment 20, the miner system 22 may acquire or download the difficulty algorithm 48. For example, the miner system 22 may determine the difficulty identifier 210 (as this disclosure above explains) and send a query to the difficulty server 160. The query specifies the difficulty identifier 210. When the difficulty server 160 receives the query, the difficulty server 160 may query the database 74 of difficulty algorithms for the difficulty identifier 210. The difficulty server 160 may locally store the database 74 of difficulty algorithms and function as a networked difficulty resource for clients. The difficulty server 160 identifies and/or retrieves the corresponding difficulty algorithm 48. The difficulty server 160 sends a query response to the miner system 22, and the query response specifies or includes the corresponding difficulty algorithm 48. The miner system 22 may then execute the difficulty algorithm 48, as above explained.

The miner system 22 may remotely retrieve the PoW algorithm 52. After the miner system 22 determines the proof-of-work ("PoW") target scheme 34 that is required by the blockchain environment 20, the miner system 22 may acquire or download the PoW algorithm 52. For example, the miner system 22 may determine the PoW identifier 214 (as this disclosure above explains) and send a query to the PoW server 124. The query specifies the PoW identifier 214. When the PoW server 124 receives the query, the PoW server 124 may query the database 78 of PoW algorithms for the PoW identifier 214. The PoW server 124 may locally store the database 78 of PoW algorithms and function as a networked proof-of-work resource for clients. The PoW server 124 identifies and/or retrieves the corresponding PoW algorithm 52. The PoW server 124 sends a query response to the miner system 22, and the query response specifies or includes the corresponding PoW algorithm 52. The miner system 22 may then execute the PoW algorithm 52, as above explained.

Figure 33:
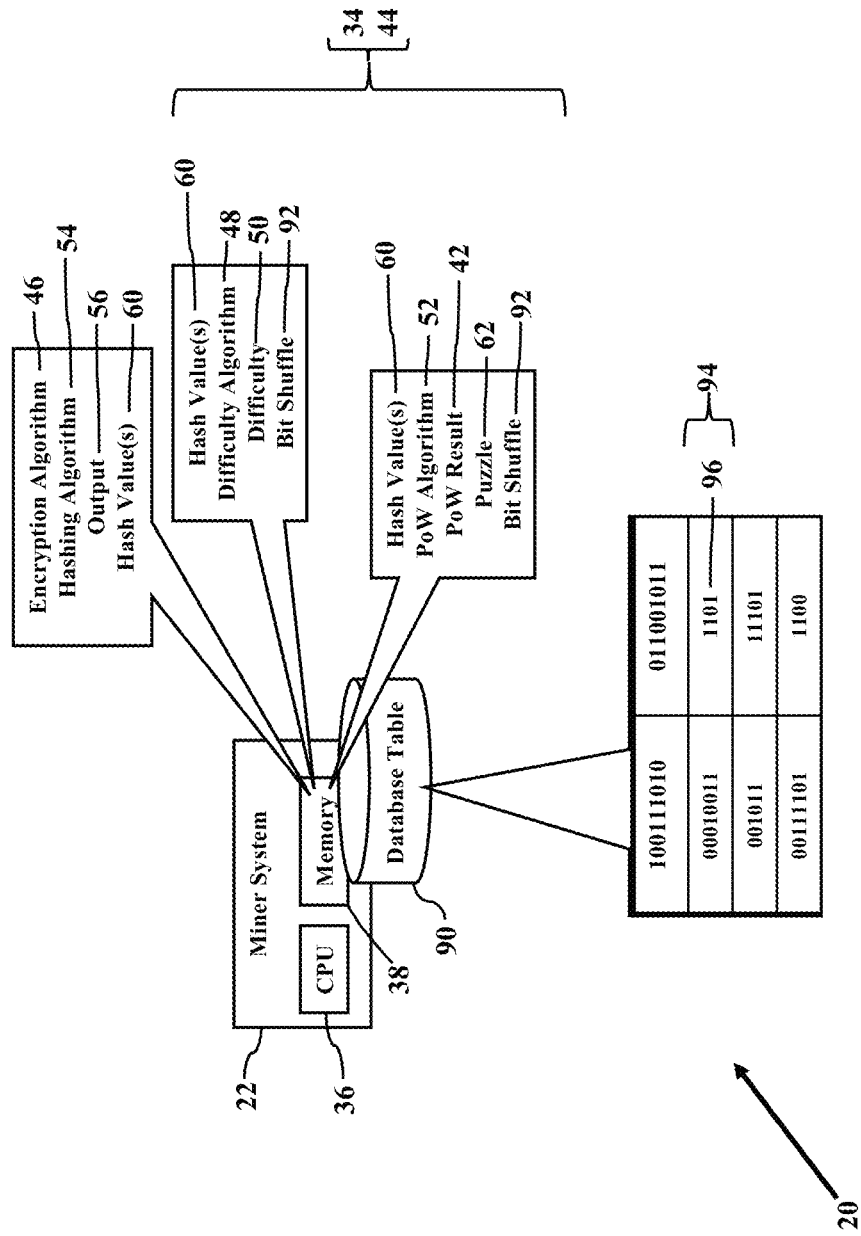
FIGS. 33-34 illustrate a bit shuffle operation, according to exemplary embodiments.
Figure 34:
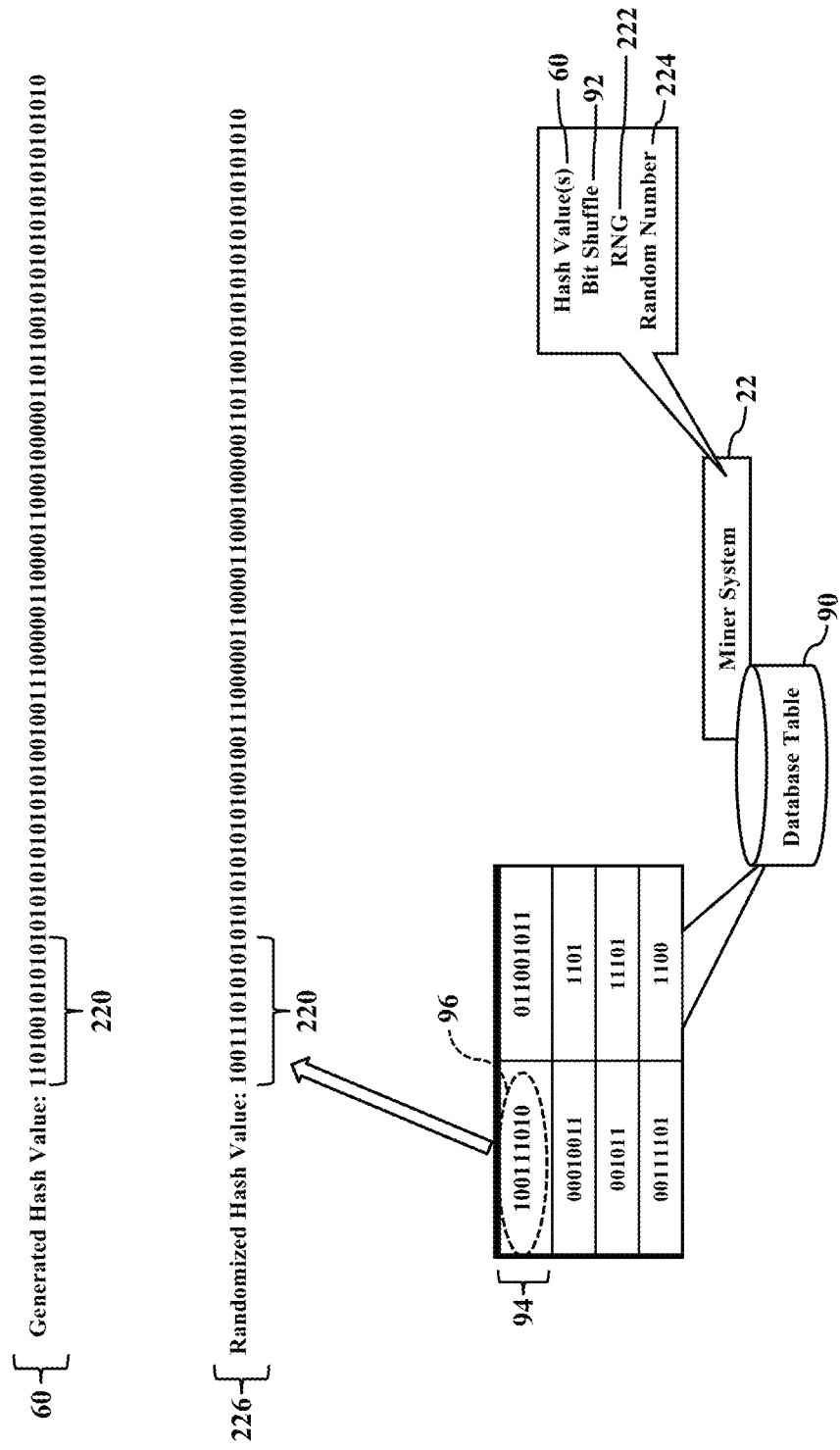

FIGS. 33-34 further illustrate the bit shuffle operation 92, according to exemplary embodiments. The difficulty algorithm 48 and/or the proof-of-work algorithm 52 may perform the bit shuffle operation 92 to conduct any difficulty and/or proof-of-work. After the hashing algorithm 54 generates the hash value(s) 60 (as this disclosure above explains), exemplary embodiments may use the database table 90 to further deter GPU/ASIC usage. The difficulty algorithm 48 and/or the proof-of-work algorithm 52 may implement the bit shuffle operation 92 on the hash value(s) 60. As FIG. 34 illustrates, suppose the hash value 60 is represented by a sequence or series of 256 bit values. The difficulty algorithm 48 and/or the proof-of-work algorithm 52 may select an arbitrary portion or number 220 of the bit values. The difficulty algorithm 48 and/or the proof-of-work algorithm 52, for example, may call, use, or execute a random number generator (RNG) 222 to generate one or more random numbers 224. As an example, a first random number 224 may be used to select an random entry 94 in the database table 90. The difficulty algorithm 48 and/or the proof-of-work algorithm 52 may then query the database table 90 for the random entry 94 and identify/retrieve the corresponding random bits 96. The difficulty algorithm 48 and/or the proof-of-work algorithm 52 may then select and replace the arbitrary portion or number 220 of the bit values in the hash value 60 with the random bits retrieved from the entry 94 in the database table 90. The bit shuffle operation 92 thus converts the hash value 60 and generates a resulting randomized hash value 226. The difficulty algorithm 48 and/or the proof-of-work algorithm 52 may instruct or cause the miner system to repeat the bit shuffle operation 92 as many times as desired. The randomized hash value 226 may, or may not, have the same number of 256 bit values. The randomized hash value 226 may have less than, or more than, 256 bit values. The randomized hash value 226 may have an arbitrary number of bit values. Once the specified or required number of bit shuffle operations 92 is complete, the difficulty algorithm 48 and/or the proof-of-work algorithm 52 may instruct or cause the miner system to determine the difficulty 50 and/or the PoW result 42 (as this disclosure above explains).

Figure 35:
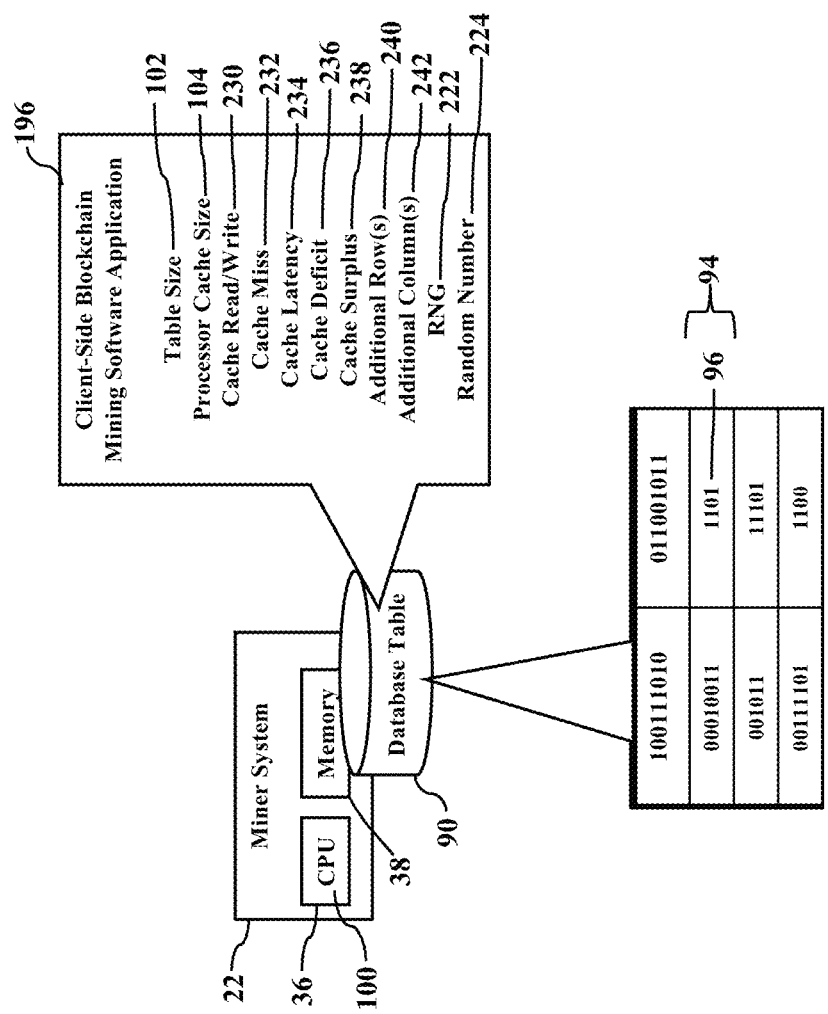
FIGS. 35-36 illustrate a database table, according to exemplary embodiments.
Figure 36:
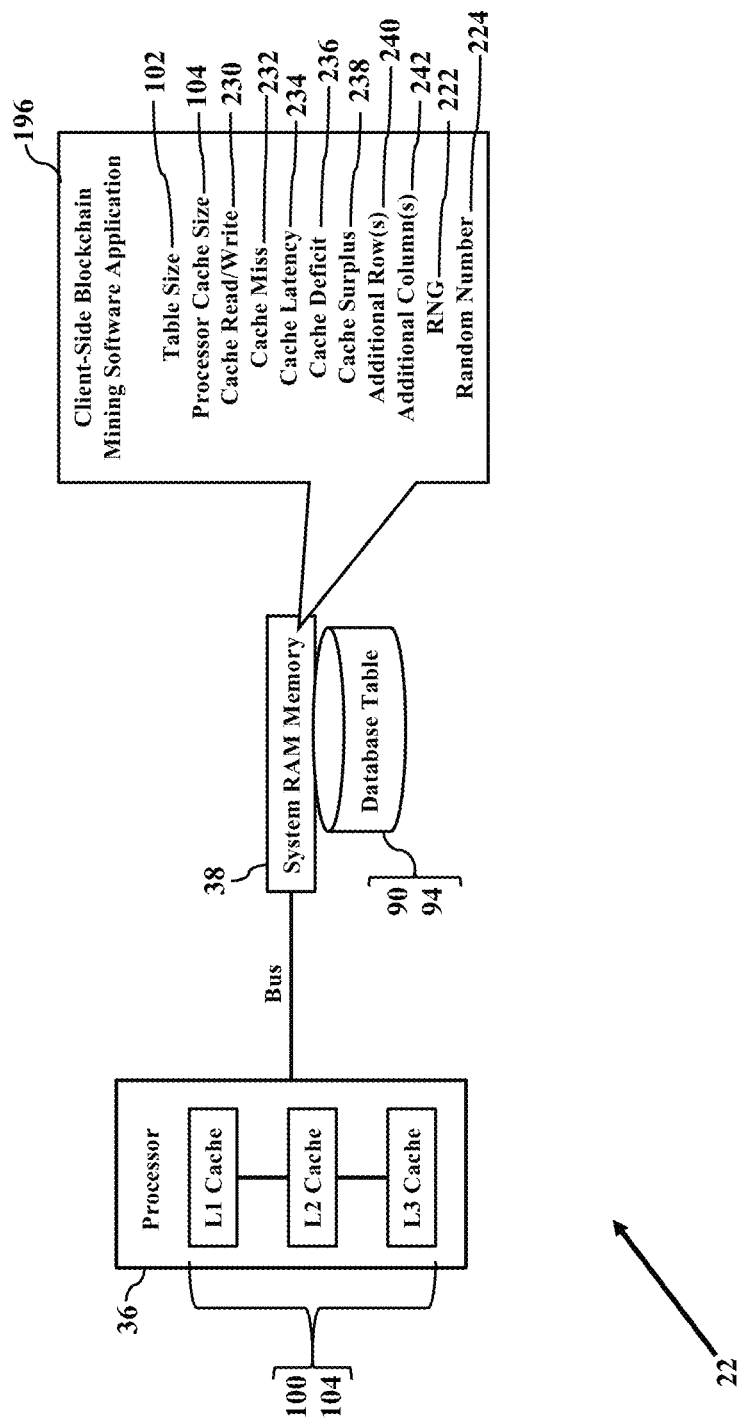

FIGS. 35-36 further illustrate the database table 90, according to exemplary embodiments. Exemplary embodiments may autonomously or automatically adjust the table byte size 102 (in bits/bytes) of the database table 90 to exceed the storage capacity or cache byte size 104 of the on-board processor cache memory 100. The client-side blockchain mining application 196, for example, may query the CPU 36 to determine the storage capacity or cache byte size 104 of the processor cache memory 100. If the table byte size 102 consumed by the database table 90 exceeds the storage capacity or cache byte size 104 of the processor cache memory 100, then perhaps no action or resolution is required. That is, the database table 90 requires more bytes or space than allocated to, or available from, the processor cache memory 100 (integrated/embedded L1, L2, and L3 SRAM/DRAM cache memory). Any cache read/write operation 230 will invalidate, thus forcing the processing component (whether a GPU, ASIC, or the CPU 36) to incur a cache miss 232 and endure the cache latency 234 of requesting and writing blocks of data via the much-slower bus from the system/main memory 38. The processing component (whether a GPU, ASIC, or the CPU 36) stalls, thus negating the use of a faster GPU or ASIC.

Exemplary embodiments may auto-size the database table 90. When the client-side blockchain mining application 196 determines the storage capacity or cache byte size 104 of the processor cache memory 100, the client-side blockchain mining application 196 may compare the storage capacity or cache byte size 104 to the table byte size 102 of the database table 90. The storage capacity or cache byte size 104 of the processor cache memory 100, for example, may be subtracted from the table byte size 102 of the database table 90. If the resulting value (in bits/bytes) is positive (greater than zero), then the database table 90 exceeds the storage capacity or cache byte size 104 of the processor cache memory 100. The client-side blockchain mining application 196 may thus determine a cache deficit 236, ensuring the cache miss 232 and the cache latency 234.

Exemplary embodiments, however, may determine a cache surplus 238. If the resulting value (in bits/bytes) is zero or negative, then the database table 90 is less than the storage capacity or cache byte size 104 of the processor cache memory 100. Whatever the processing component (whether a GPU, ASIC, or the CPU 36), some or even all of the database table 90 could be stored and retrieved from the processor cache memory 100, thus giving an advantage to a faster processing component. The client-side blockchain mining application 196 may thus increase the table byte size 102 of the database table 90. The client-side blockchain mining application 196, for example, may add one (1) or more additional database rows 240 and/or one (1) or more additional database columns 242. The client-side blockchain mining application 196 may increase the table byte size 102 of the database table 90 by adding additional entries 94, with each added entry 94 specifying more random bits 96. As an example, the client-side blockchain mining application 196 may call, use, or execute the random number generator 222 to generate the random number 224 and then add the additional database row(s) 240 and/or additional database column(s) 242 according to the random number 224. Exemplary embodiments may thus continually or periodically monitor the storage capacity or cache byte size 104 of the processor cache memory 100 and the table byte size 102 of the database table 90. The cache surplus 238 may trigger a resizing operation to ensure the database table 90 always exceeds the processor cache memory 100.

The database table 90 may be large. The above examples only illustrated a simple configuration of a few database entries 94. In actual practice, though, the database table 90 may have hundreds, thousands, or even millions of the rows and columns, perhaps producing hundreds, thousands, millions, or even billions of database entries 94. Exemplary embodiments may repeatedly perform the bit shuffle operation 92 to suit any difficulty or proof-of-work strategy or scheme. The proof-of-work target scheme 34, the difficulty algorithm 48, and/or the proof-of-work algorithm 52 may each specify a minimum and/or a maximum number of bit shuffle operations that are performed.

Exemplary embodiments may use the XOR/Shift random number generator (RNG) 222 coupled with the lookup database table 90 of randomized sets of bytes. The database table 90 may have any number of 256 byte tables combined and shuffled into one large byte lookup table. Exemplary embodiments may then index into this large table to translate the state built up while hashing into deterministic but random byte values. Using a 1 GB lookup table results in a RAM I-lash PoW algorithm that spends over 90% of its execution time waiting on memory (RAM) than it does computing the hash. This means far less power consumption, and ASIC and GPU resistance. The ideal platform for PoW using a RAM Hash is a Single Board Computer like a Raspberry PI 4 with 2 GB of memory.

Any or all parameters may be specified. The size of the database table 90 may be specified in bits for the index, the seed used to shuffle the lookup table, the number of rounds to shuffle the table, and the size of the resulting hash. Because the LXRHash is parameterized in this way, as computers get faster and larger memory caches, the LXRHash can be set to use 2 GB or 16 GB or more. The Memory bottleneck to computation is much easier to manage than attempts to find computational algorithms that cannot be executed faster and cheaper with custom hardware, or specialty hardware like GPUs. Very large lookup tables will blow the memory caches on pretty much any processor or computer architecture. The size of the database table 90 can be increased to counter improvements in memory caching. The number of bytes in the resulting hash can be increased for more security (greater hash space), without significantly more processing time. LXRHash may even be fast by using small lookup tables. ASIC implementations for small tables would be very easy and very fast. LXRHash only uses iterators (for indexing) shifts, binary ANDs and XORs, and random byte lookups. The use case for LXRHash is Proof of Work (PoW), not cryptographic hashing.

The database table 90 may have equal numbers of every byte value, and shuffled deterministically. When hashing, the bytes from the source data are used to build offsets and state that are in turn used to map the next byte of source. In developing this hash, the goal was to produce very randomized hashes as outputs, with a strong avalanche response to any change to any source byte. This is the prime requirement of PoW. Because of the limited time to perform hashing in a blockchain, collision avoidance is important but not critical. More critical is ensuring engineering the output of the hash isn't possible. Exemplary embodiments yield some interesting qualities. For example, the database table 90 may be any size, so making a version that is ASIC resistant is possible by using very big lookup tables. Such tables blow the processor caches on CPUs and GPUs, making the speed of the hash dependent on random access of memory, not processor power. Using 1 GB lookup table, a very fast ASIC improving hashing is limited to about ~10% of the computational time for the hash. 90% of the time hashing isn't spent on computation but is spent waiting for memory access. At smaller lookup table sizes, where processor caches work. LXRHash can be modified to be very fast. LXRHash would be an easy ASIC design as it only uses counters, decrements, XORs, and shifts. The hash may be altered by changing the size of the lookup table, the seed, size of the hash produced. Change any parameter and you change the space from which hashes are produced. The Microprocessor in most computer systems accounts for 10× the power requirements of memory. If we consider PoW on a device over time, then LXRHash is estimated to reduce power requirements by about a factor of 10.

Testing has revealed some optimizations. LXRHash is comparatively slow by design (to make POW CPU bound), but quite a number of use cases don't need PoW, but really just need to validate data matches the hash. So using LXRHash as a hashing function isn't as desirable as simply using it as a PoW function. The somewhat obvious conclusion is that in fact we can use Sha256 as the hash function for applications, and only use the LXR approach as a PoW measure. So in this case, what we do is change how we compute the PoW of a hash. So instead of simply looking at the high order bits and saying that the greater the value the greater the difficulty (or the lower the value the lower the difficulty) we instead define an expensive function to calculate the PoW.

Exemplary embodiments may break out PoW measures from cryptographic hashes. The advantage here is that what exactly it means to weigh PoW between miners can be determined apart from the hash that secures a blockchain. Also, a good cryptographic hash provides a much better base from which to randomize PoW even if we are going to use a 1 GB byte map to bound performance by DRAM access. And we could also use past mining, reputation, staking, or other factors to add to PoW at this point.

PoW may be represented as a nice standard sized value. Because exemplary embodiments may use a function to compute the PoW, we can also easily standardize the size of the difficulty. Since bytes that are all 0xFF or all 0x00 are pretty much wasted, we can simply count them and combine that count with the following bytes. This encoding is compact and easily compared to other difficulties in a standard size with plenty of resolution. So with PoW represented as a large number, the bigger the more difficult, the following rules may be followed. Where bit 0 is most significant, and bit 63 is least significant:

Bits 0-3 Count of leading 0xFF bytes; and
Bits 4-63 bits of the following bytes.

For example, given the hash
ffffff7312334c442bf42625f7856fe0d50e4aa45c98d7a391c016b89e242d94,
the difficulty is 37312334c442bf42. The computation counts the leading bytes with a value of 0xFF, then calculates the uint64 value of the next 8 bytes. The count is combined with the following bytes by shifting the 8 bytes right by 4, and adding the count shifted left by 60. As computing power grows, more significant bits of the hash can be used to represent the difficulty. At a minimum, difficulty is represented by 4 bits 0x0 plus the following 0+60 bits=>60 bits of accuracy. At the maximum, difficulty is represented by 4 bits 0xF plus the following 60 bits=>120+60=180 bits of accuracy.

Sha256 is very well tested as a cryptographic function, with excellent waterfall properties (meaning odds are very close to 50% that any change in the input will flit any particular bit in the resulting hash). Hashing the data being mined by the miners is pretty fast. If an application chooses to use a different hashing function, that's okay as well.

FIGS. 37-40 illustrate a table identifier mechanism, according to exemplary embodiments. When the miner system 22 communicates with the blockchain network server 28, the blockchain network server 28 may specify the proof-of-work ("PoW") target scheme 34 and/or the database table 90 that is required by the blockchain environment 20. For example, in order to reduce a memory byte size and/or programming line size of the proof-of-work ("PoW") target scheme 34 and/or the client-side blockchain mining software application 196, exemplary embodiments may only specify a table identifier 250 associated with the blockchain network's chosen or required difficulty and proof-of-work scheme. The table identifier 250 may be any alphanumeric combination, hash value, network address, website, or other data/information that uniquely identifies the database table 90 used by the blockchain environment 20. The blockchain network server 28 may thus send the table identifier 250 (via the communications network 26) to the miner system 22. The table identifier 250 may be packaged as a downloadable component, parameter, or value with the client-side blockchain mining software application 196. However, the table identifier 250 may additionally or alternatively be sent to the miner system 22, such as the packetized message 202 that includes or specifies the table identifier 250 (explained with reference to FIGS. 22-31). Because the table identifier 250 may be separately sent from the client-side blockchain mining software application 196, the table identifier 250 may be dynamically updated or changed without downloading a new or updated client-side blockchain mining software application 196.

Figure 37:
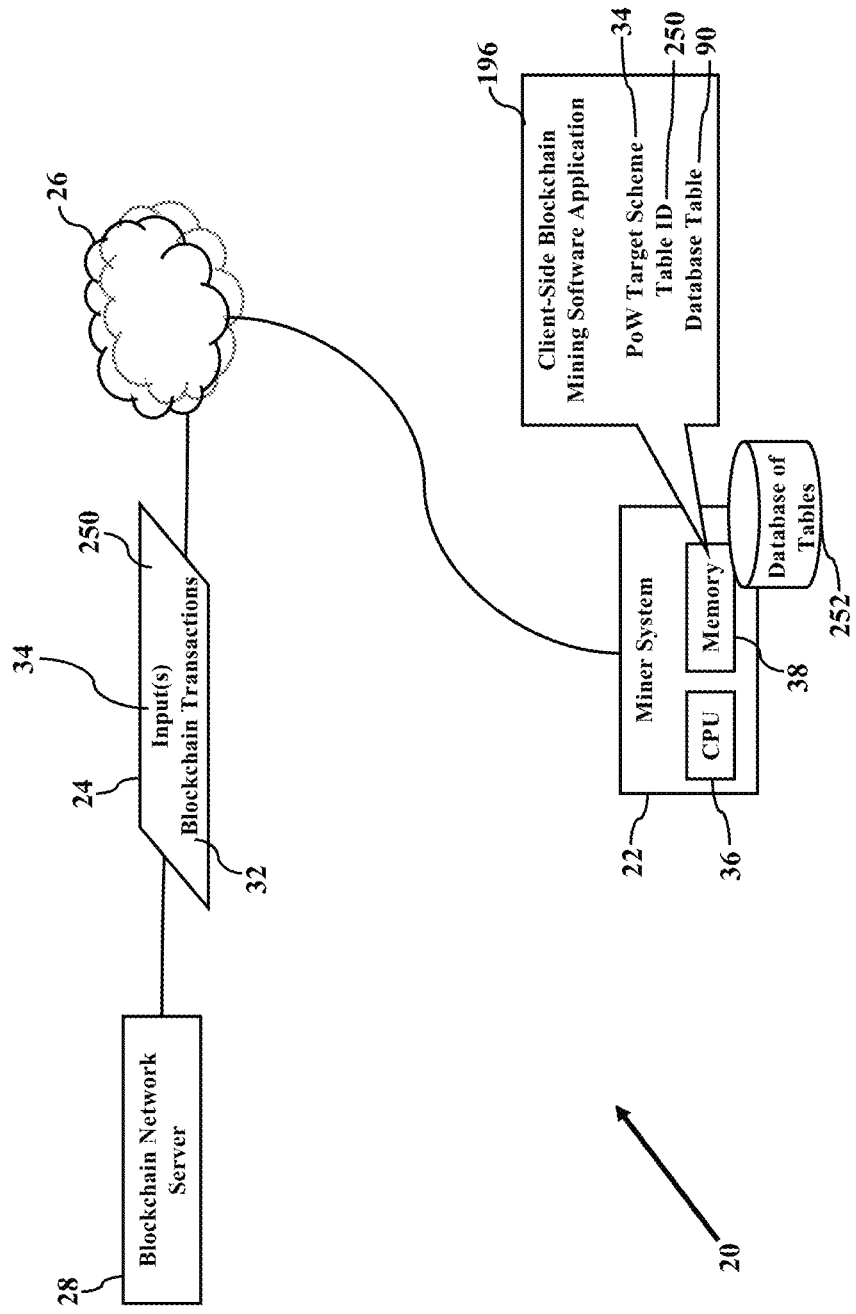
FIGS. 37-40 illustrate a table identifier mechanism, according to exemplary embodiments.

Exemplary embodiments may consult an electronic database 252 of tables. When the miner system 22 receives the table identifier 250, the miner system 22 may use, call, and/or implement the database table 90 represented by the table identifier 250. The miner system 22 may obtain, read, or retrieve the table identifier 250 specified by the client-side blockchain mining software application 196. The miner system 22 may additionally or alternatively inspect, read, or retrieve the table identifier 250 from the message 202. Once the table identifier 250 is determined, the miner system 22 may identify the corresponding database table 90 by querying the database 252 of tables for the table identifier 250. FIG. 37 illustrates the electronic database 252 of tables locally stored in the memory device 38 of the miner system 22. The database 252 of tables stores, references, or associates the table identifier 250 and/or the proof-of-work target scheme 34 to the corresponding database table 90. The miner system 22 may thus identify and/or retrieve the database table 90. The miner system 22 may then execute the difficulty algorithm 48 and/or the proof-of-work algorithm using the entries specified by the database table 90 (as this disclosure above explains).

Figure 38:
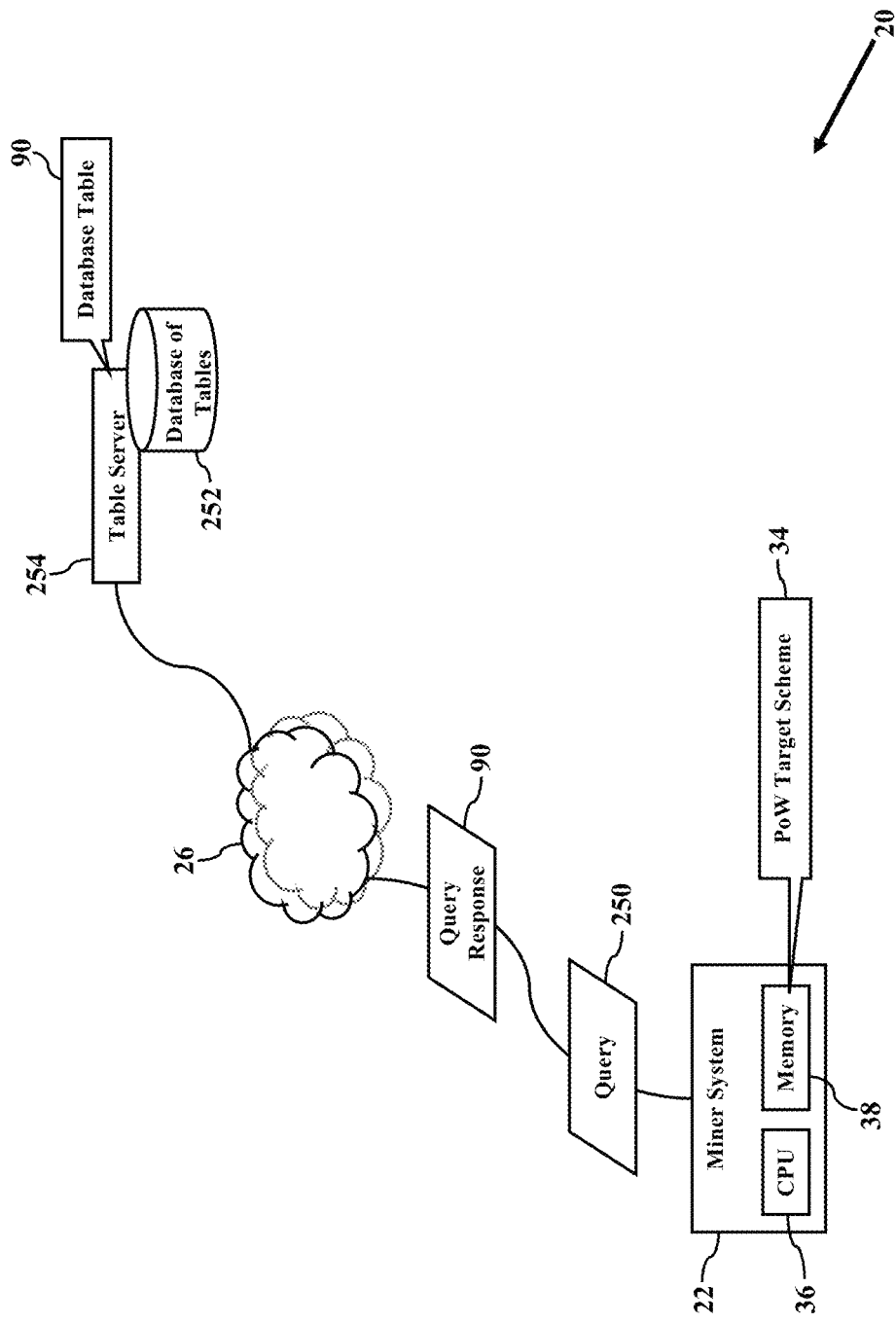

FIG. 38 illustrates remote retrieval. FIG. 38 illustrates the database 252 of tables remotely stored by a table server 254 and accessed via the communications network 26. The table server 254 may be the only authorized source for the database table 90. The table server 254 may thus operate within the blockchain environment 20 and provide the latest/current database table 90 for all miners in the blockchain network. The table server 254, however, may be operated on behalf of an authorized third-party vendor or supplier that provides the database table 90 for all miners in the blockchain network. Once the miner system 22 determines the table identifier 250, the miner system 22 may send a query to the network address associated with or assigned to the table server 254. The query specifies the table identifier 250. When the table server 254 receives the query, the table server 254 queries the electronic database 252 of tables for the table identifier 250 specified by the query. The table server 254 has a hardware processor and memory device (not shown for simplicity) that stores and executes a query handler software application. The query handler software application causes the table server 254 to perform a database lookup operation. The table server 254 identifies the corresponding database table 90 by querying the database 252 of tables for the table identifier 250. The table server 254 generates and sends a query response to the network address associated with or assigned to the miner system 22, and the query response includes or specifies the database table 90 that is associated with the table identifier 250. The miner system 22 may thus identify, download, and/or retrieve the database table 90.

Because the database 252 of tables may store or reference many different database tables, exemplary embodiments may dynamically switch or change the database table 90 to suit any objective or performance criterion. Exemplary embodiments may thus need only specify the table identifier 250, and the table identifier 250 may be dynamically changed at any time. The blockchain environment 20 may flexibly switch, change, and evaluate different database tables, merely by changing or modifying the table identifier 250. The blockchain network may thus experiment with different database tables, different difficulty algorithms 48, and/or different proof-of-work algorithms 52 with little or no impact or effect on hashing. Should an experimental scheme prove or become undesirable, for whatever reason(s), the blockchain environment 20 (such as the blockchain network server 28) may distribute, assign, or restore a new/different table identifier 250 (perhaps by updating the client-side blockchain mining software application 196 and/or distributing/broadcasting the message 202, as this disclosure above explains). The blockchain environment 20 may thus dynamically change the database table 90, which may concomitantly change the difficulty algorithm 48 and/or the proof-of-work algorithm 52, for quick evaluation and/or problem resolution.

Figure 39:
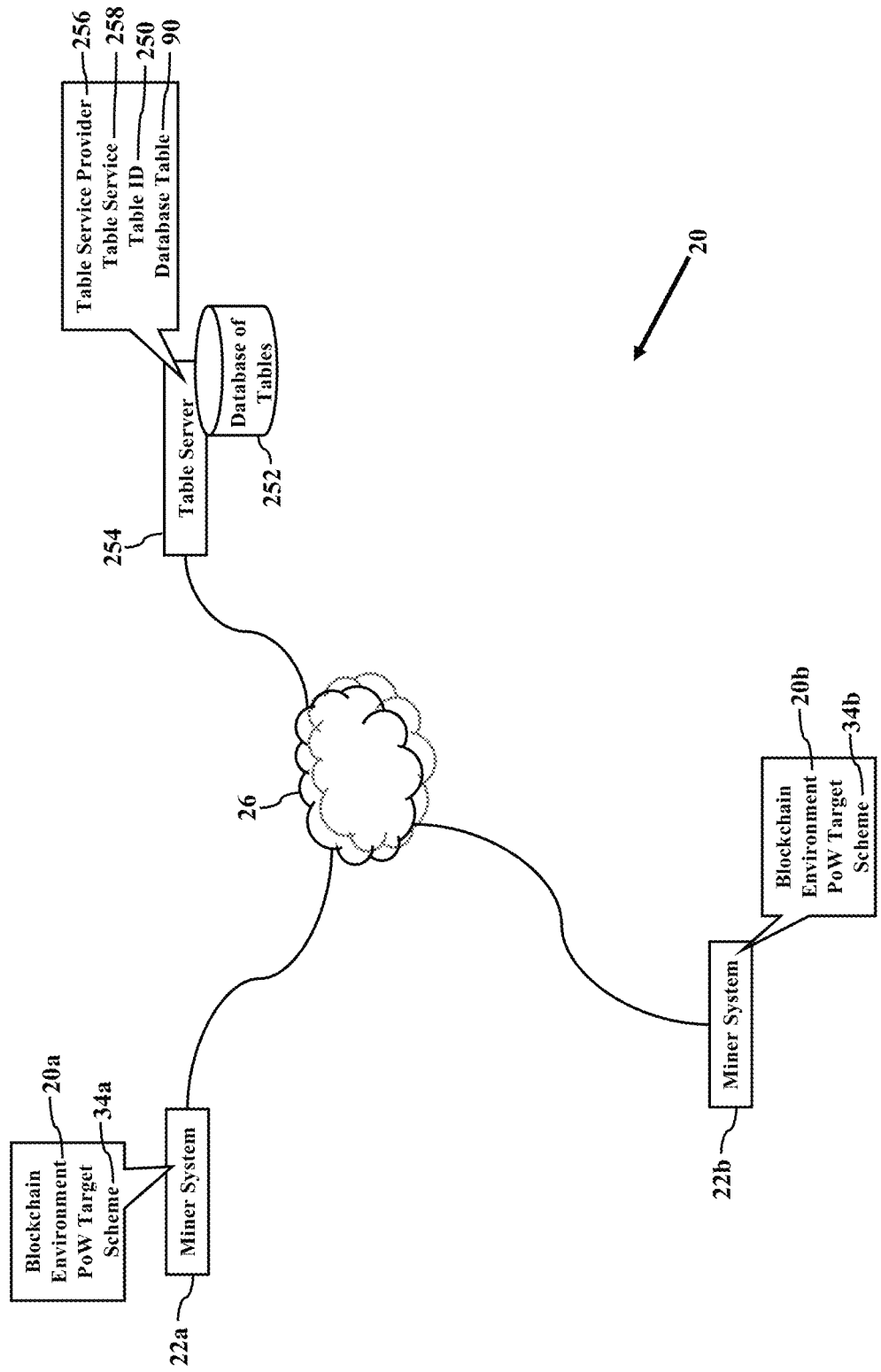

FIG. 39 further illustrates table services. Here the table server 254 may serve different blockchain environments 20. For example, the table server 254 may server miners 22a operating in blockchain environment 20a. The table server

254 may also server miners 22*b* operating in blockchain environment 20*b*. The table server 254 may thus be operated on behalf of a table service provider 256 that provides a table service 258 to clients and blockchain networks. The table service provider 256 may receive, generate, and/or store different database tables 90, perhaps according to a client's or a blockchain's specification. Each different table 90 may have its corresponding unique table identifier 250. So, whatever the proof-of-work ("PoW") target scheme (e.g., 34*a* and 34*b*) and/or the blockchain environment 20*a-b*, the table server 254 may offer and provide the corresponding database table 90. The table service provider 256 and/or the table server 254 may thus be an authorized provider or participant in the blockchain environments 20*a-b*. A first miner system 22*a*, for example, operating in the blockchain environment 20*a*, may request and retrieve the database table 90*a* that corresponds to the proof-of-work ("PoW") target scheme 34*a*. A different, second system 22*b*, operating in the blockchain environment 20*b*, may request and retrieve the database table 90*b* that corresponds to the proof-of-work ("PoW") target scheme 34*b*. Miners may query the table server 254 (perhaps by specifying the corresponding table ID 250) and retrieve the corresponding database table 90. The table service provider 256 may thus specialize in randomized/cryptographic database tables, and the table server 254 may serve different blockchain networks.

Figure 40:
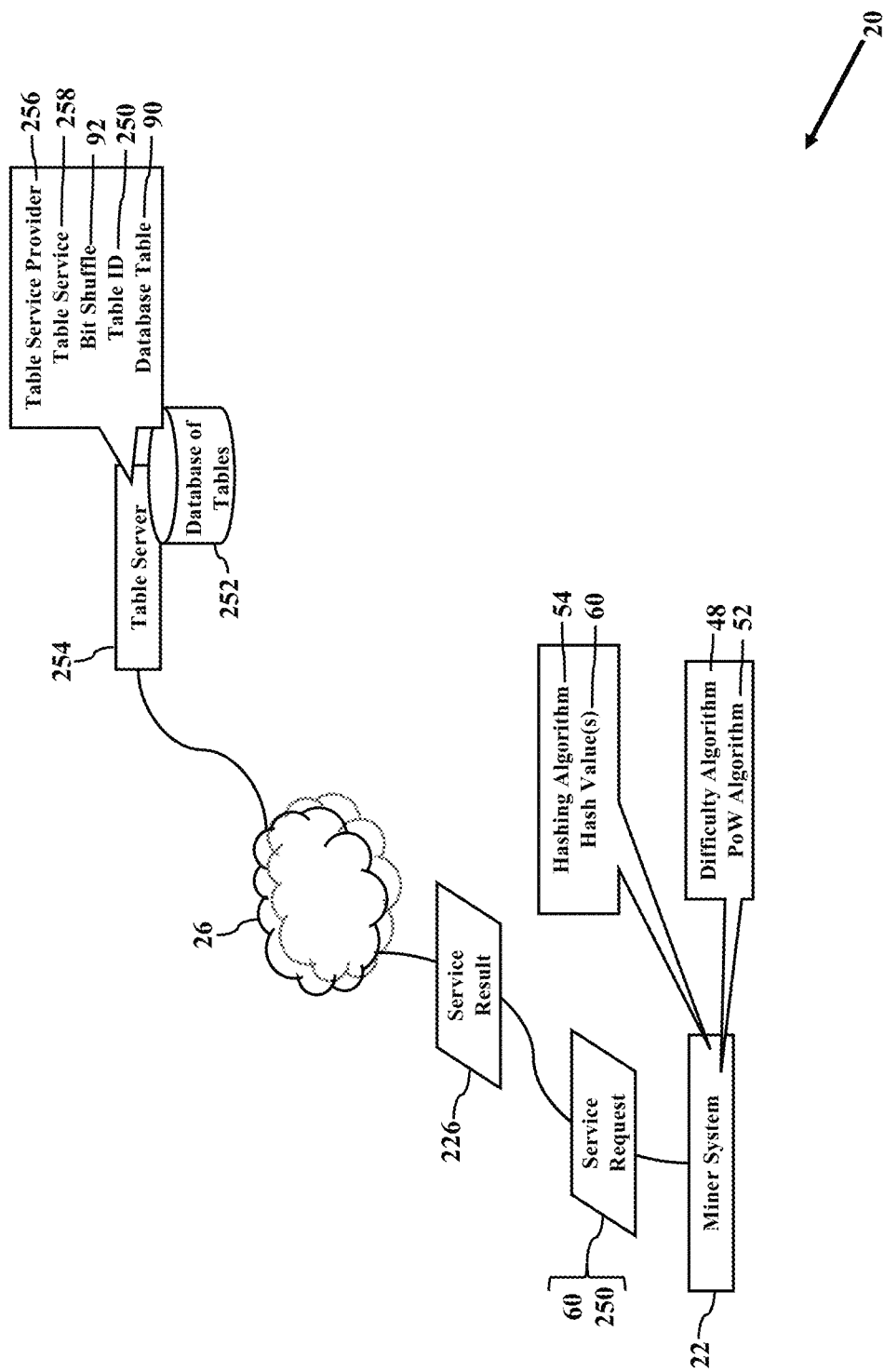

FIG. 40 further illustrates table services. The blockchain environment 20 and/or the miner system 22 may outsource the bit shuffle operation 92 to the table service provider 256. Once the miner system 22 determines or receives the hash value(s) 60 (generated by the hashing algorithm 54), the miner system 22 may outsource or subcontract the bit swap operation 92 to the table server 254. The client-side blockchain mining software application 196 may thus cause or instruct the miner system 22 to generate a bit shuffle service request that is sent to the table service provider 256 (such as the IP address assigned to the table server 254). The bit shuffle service request may specify or include the hash values 60. The bit shuffle service request may additionally or alternatively specify or include the table identifier 250. The bit shuffle service request may additionally or alternatively specify or include a website, webpage, network address location, or server from which the hash values 60 may be downloaded, retrieved, or obtained to perform the bit shuffle operation 92. While the table service provider 256 may utilize any mechanism to provide the bit shuffle operation 92, FIG. 40 illustrates a vendor's server/client relationship. The miner system 22 sends the bit shuffle service request to the table server 254 that is operated on behalf of the table service provider 256. When the table server 254 receives the bit shuffle service request, the table server 254 may query the database 252 of tables for the table identifier 250 specified by the bit shuffle service request. The table server 254 identifies the corresponding database table 90. The table server 254 performs the bit shuffle operation 92 using the hash value(s) 60 specified by, or referenced by, the bit shuffle service request. The table server 254 generates and sends a service result to the network address associated with or assigned to the miner system 22, and the service result includes or specifies data or information representing the randomized hash value(s) 226. The miner system 22 may then execute, or outsource, the difficulty algorithm 48 and/or the proof-of-work algorithm 52 using the randomized hash value(s) 226 (as this disclosure above explained).

Exemplary embodiments improve computer functioning. The database table 90 adds cryptographic security by further randomizing the hash value(s) 60 generated by the hashing algorithm 54. Moreover, because the database table 90 may be remotely located and accessed, exemplary embodiments may only specify the table identifier 250. The memory byte size consumed by the proof-of-work ("PoW") target scheme 34 and/or the client-side blockchain mining software application 196 is reduced. That is, the blockchain network server 28 need not send the entire software program, code, or instructions representing the database table 90 used by the blockchain environment 20. The blockchain environment 20, the blockchain network server 28, and/or the proof-of-work ("PoW") target scheme 34 need only specify the much smaller byte-sized table identifier 250. The blockchain environment 20 need not be burdened with conveying the database table 90 to the miner system 22 and to other mining nodes. The blockchain environment 20 and the communication network 26 convey less packet traffic, so packet travel times and network latency are reduced. Moreover, especially if the miner system 22 outsources table operations, the miner system 22 is relieved from processing/executing the bit swap operation 92 and consumes less electrical power. Again, then, a faster and more expensive graphics processor or even ASIC will not speed up the proof-of-work operation. The conventional central processing unit 36 is adequate, reduces costs, and promotes democratic mining.

Exemplary embodiments improve cryptographic security. If the blockchain environment 20, the proof-of-work ("PoW") target scheme 34 and/or the client-side blockchain mining software application 196 specifies use of the database table 90, only authorized miners may have access to the actual entries referenced by the database table 90. That is, if miner system 22 is required to perform, implement, or even execute the bit shuffle operation 92, the miner system 22 must have access to the correct database table 90. An unauthorized or rogue entity, in other words, likely could not perform the bit shuffle operation 92 without access to the correct database table 90. Moreover, if the bit shuffle operation 92 is remotely performed from the miner system 22 (such as by the table server 254, as above explained), perhaps not even the authorized miner system 22 need have access to the database table 90. So, even if the miner system 22 is authorized to mine or process blockchain transactions 32 in the blockchain environment 20, the authorized miner system 22 may still be blind to the database table 90. The authorized miner system 22, in other words, is operationally reliant on the table server 254 to perform the bit shuffle operation 92 that may be required for the difficulty algorithm 48 and/or for the proof-of-work algorithm 52. The miner system 22 simply cannot solve the mathematical puzzle 62 without the table service 258 provided by the table server 254. The database table 90 may thus be proprietary to the blockchain environment 20, but, unknown and unavailable to even the authorized miner system 22 for added cryptographic security.

Figure 41:
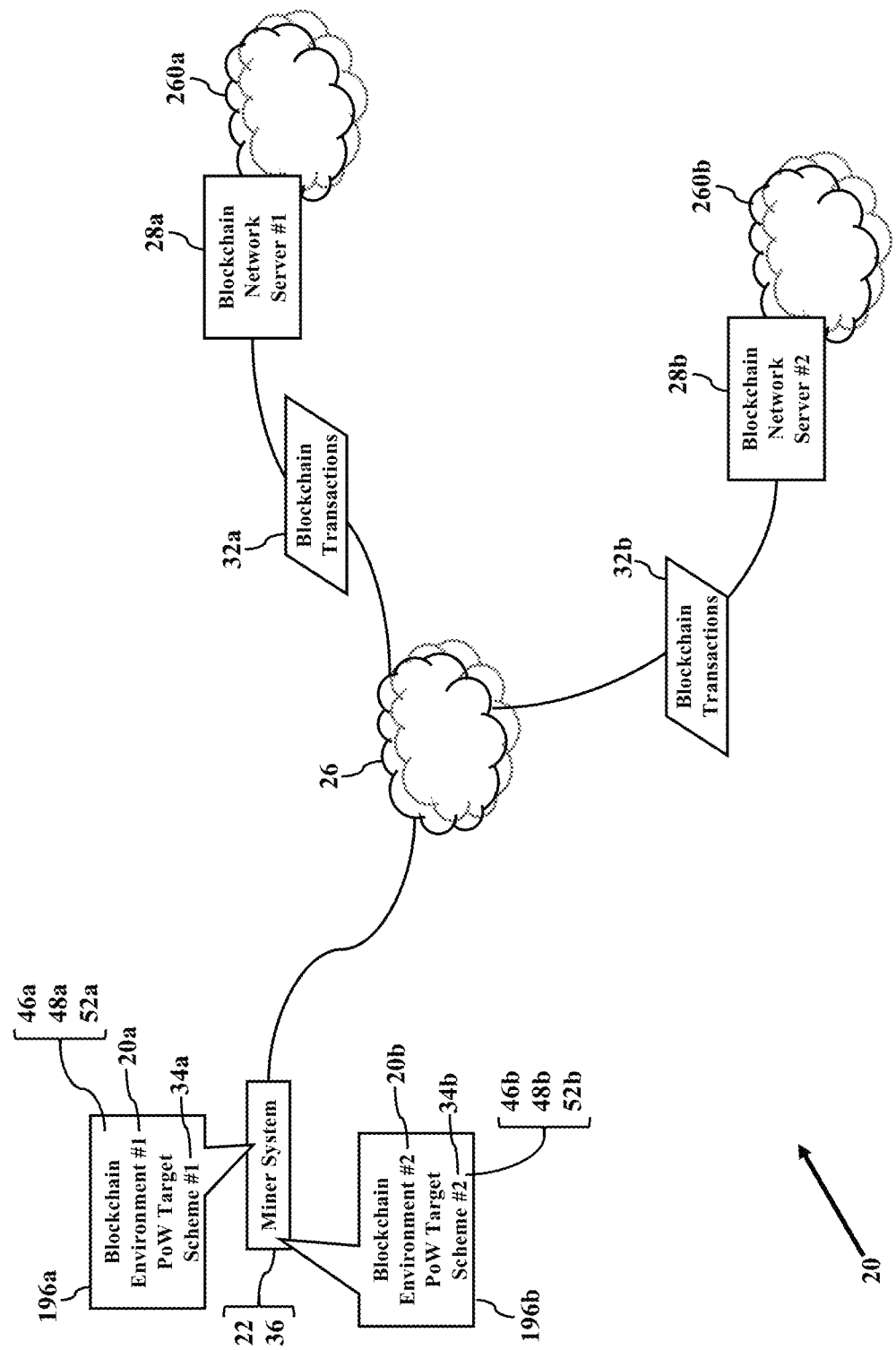
FIG. 41 illustrates agnostic blockchain mining, according to exemplary embodiments

FIG. 41 illustrates agnostic blockchain mining, according to exemplary embodiments. As the reader may now realize, the miner system 22 may be agnostic to the blockchain environment 20. Because the miner system 22 may be agnostic to encryption, difficulty, and proof-of-work operations, the miner system 22 may process or mine the blockchain transactions 32 in multiple blockchain environments 20. That is, because the conventional CPU 36 is adequate for mining blockchain transactions 32, no specialized ASIC is required for any particular blockchain environment 20. The miner system 22 may thus participate in multiple blockchain environments 20 and potentially earn multiple rewards. The miner system 22, for example, may participate in the blockchain environment 22*a* and mine the blockchain transactions 32a sent from the blockchain network server 28a to authorized miners in blockchain network 260a. The miner system 22 may thus mine the blockchain transactions 32a according to the proof-of-work ("PoW") target scheme 34a that is specified by the blockchain environment 22a, the blockchain network server 28a, and/or the blockchain network 260a. The miner system 22, however, may also participate in the blockchain environment 22b and mine the blockchain transactions 32b sent from the blockchain network server 28b to authorized miners in blockchain network 260b. The miner system 22 may thus mine the blockchain transactions 32b according to the proof-of-work ("PoW") target scheme 34b that is specified by the blockchain environment 22b, the blockchain network server 28b, and/or the blockchain network 260b. Because exemplary embodiments require no specialized GPU or ASIC, the miner's conventional CPU 36 may be adequate for mining operations in both blockchain environments 22a and 22b. The miner system 22 may thus download, store, and execute the client-side blockchain mining software application 196a that is required to mine the blockchain transactions 32a in the blockchain environment 20a. The miner system 22 may also download, store, and execute the client-side blockchain mining software application 196b that is required to mine the blockchain transactions 32b in the blockchain environment 20b. The miner system 22 may thus call, execute, coordinate, or manage the encryption algorithm 46a, the difficulty algorithm 48a, and/or the proof-of-work ("PoW") algorithm 52a according to the proof-of-work ("PoW") target scheme 34a specified by the blockchain environment 20a. The miner system 22 may also call, execute, coordinate, or manage the encryption algorithm 46b, the difficulty algorithm 48b, and/or the proof-of-work ("PoW") algorithm 52b according to the proof-of-work ("PoW") target scheme 34b specified by the blockchain environment 20b. Because exemplary embodiments require no specialized GPU or ASIC, the miner system 22 has the hardware processor capability and performance (e.g., clock speed, processor core(s)/thread(s) count, cycles, the on-board cache memory 100, thermal profile, electrical power consumption, and/or chipset) to mine in both blockchain environments 20a and 20b. The miner system 22 may participate in multiple blockchain environments 20, thus having the capability to earn additional rewards, while also being less expensive to purchase and to operate.

Figure 42:
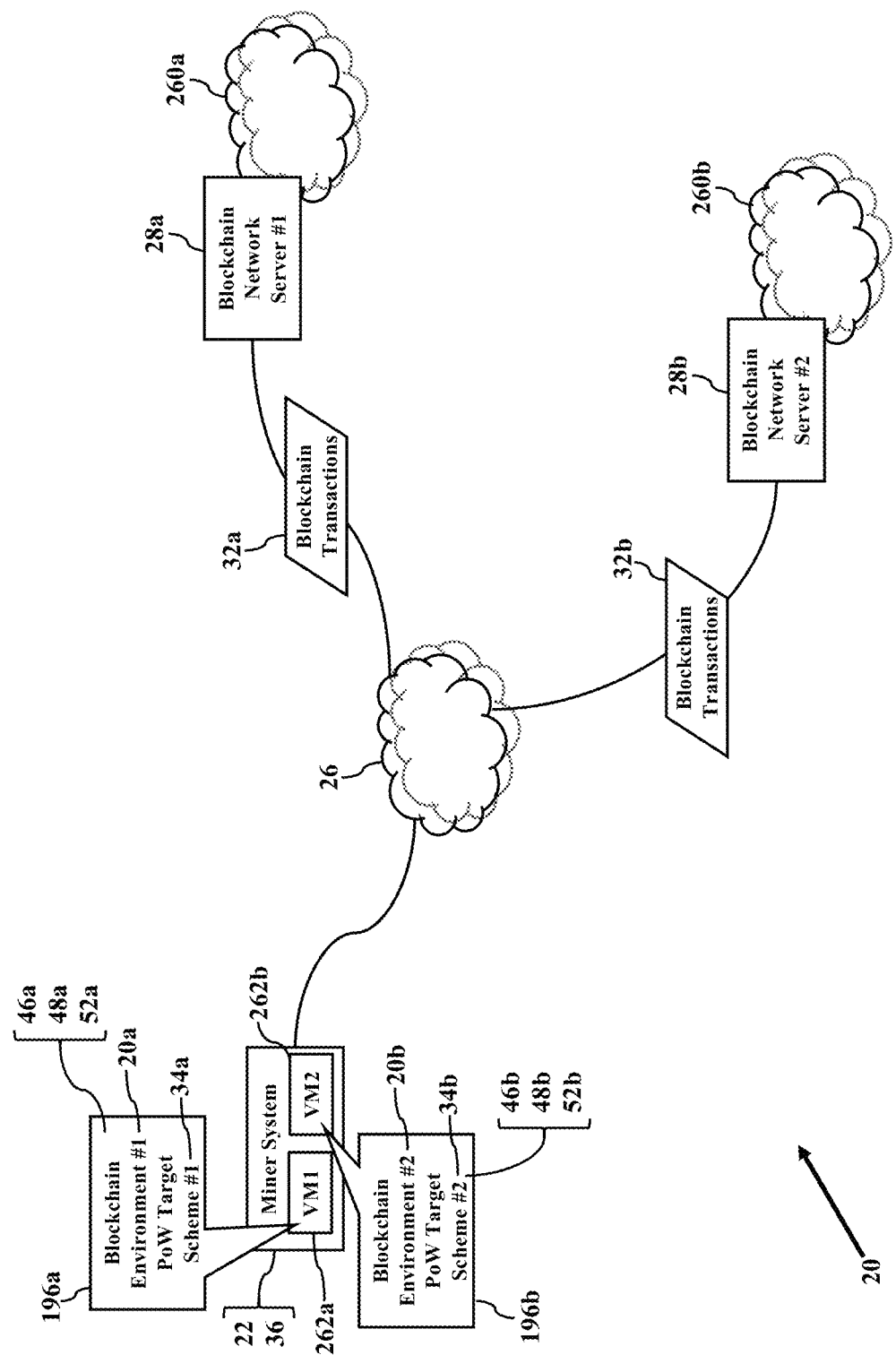
FIGS. 42-43 illustrate virtual blockchain mining, according to exemplary embodiments.
Figure 43:
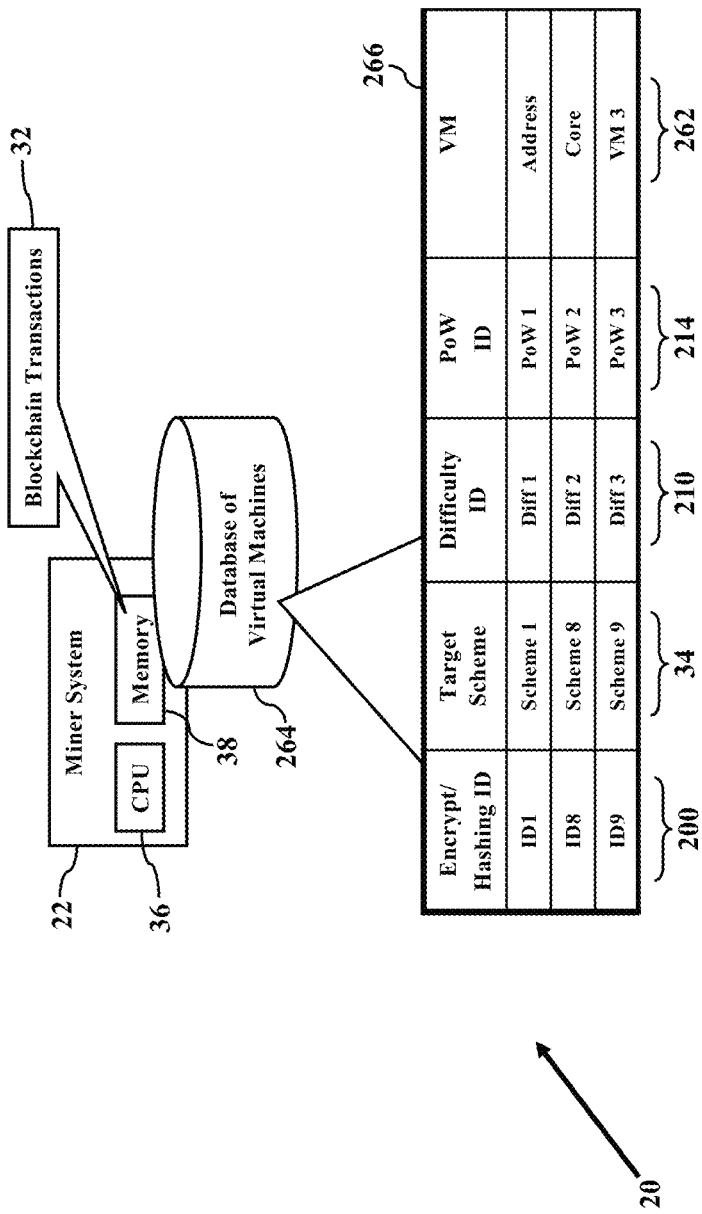

FIGS. 42-43 illustrate virtual blockchain mining, according to exemplary embodiments. Because the miner system 22 may be agnostic to the blockchain environment 20, the miner system 22 may outsource or subcontract mining operations to a virtual machine (or "VM") 262. For example, the miner system 22 may implement different virtual machines 262, with each virtual machine 262 dedicated to a particular blockchain environment 20. The miner system 22, for example, may assign the virtual machine 262a to mining the blockchain transactions 32a sent from the blockchain network server 28a. The miner system 22 may assign the virtual machine 262b to mining the blockchain transactions 32b sent from the blockchain network server 28b. The miner system 22 may thus be a server computer that participates in multiple blockchain environments 20 and potentially earns multiple rewards. The miner system 22 may provide virtual mining resources to multiple blockchain environments 20, thus lending or sharing its hardware, computing, and programming resources. While FIG. 42 only illustrates two (2) virtual machines 262a and 262b, in practice the miner system 22 may implement any number or instantiations of different virtual machines 262, with each virtual machine 262 serving or mining one or multiple blockchain environments 20. So, when the miner system 22 receives the blockchain transactions 32, the miner system 22 may inspect the blockchain transactions 32 for the proof-of-work ("PoW") target scheme 34 that identifies the corresponding encryption, difficulty, and PoW scheme (such as by consulting the databases 70, 74, and 78, as above explained). The miner system 22 may additionally or alternatively inspect the blockchain transactions 32 for the identifiers 200, 210, 214, and 250 (as this disclosure above explains). Once the blockchain environment 20 is determined, the miner system 22 may then FIG. 43 illustrates a database lookup. When the miner system 22 determines the PoW scheme 34 and/or any of the identifiers 200, 210, 214, and 250, the miner system 22 may identify the corresponding virtual machine 262. For example, the miner system 22 may consult an electronic database 264 of virtual machines. While the database 264 of virtual machines may have any structure, FIG. 43 illustrates a relational table 266 having entries that map or associate the PoW scheme 34 and/or any of the identifiers 200, 210, 214, 250 to the corresponding virtual machine 262. The miner system 22 may thus query the electronic database 264 of virtual machines for any of the PoW scheme 34 and/or any of the identifiers 200, 210, 214, 250 and determine the corresponding virtual machine 262. Once the virtual machine 262 is identified (e.g., a memory address or pointer, processor core, identifier, network address and/or service provider, or other indicator), the miner system 22 may assign the blockchain transactions 32 to the virtual machine 262 for mining.

The miner system 22 may thus serve many blockchains. The miner system 22, for example, may mine BITCOIN® and other cryptographic coin transactional records. However, the miner system 22 may also nearly simultaneously mine financial records sent from or associated with a financial institution, inventory/sales/shipping records sent from a retailer, and transactional records sent from an online website. The miner system 22 may participate in multiple blockchain environments 20, thus having the capability to earn additional rewards, while also being less expensive to purchase and to operate.

Figure 44:
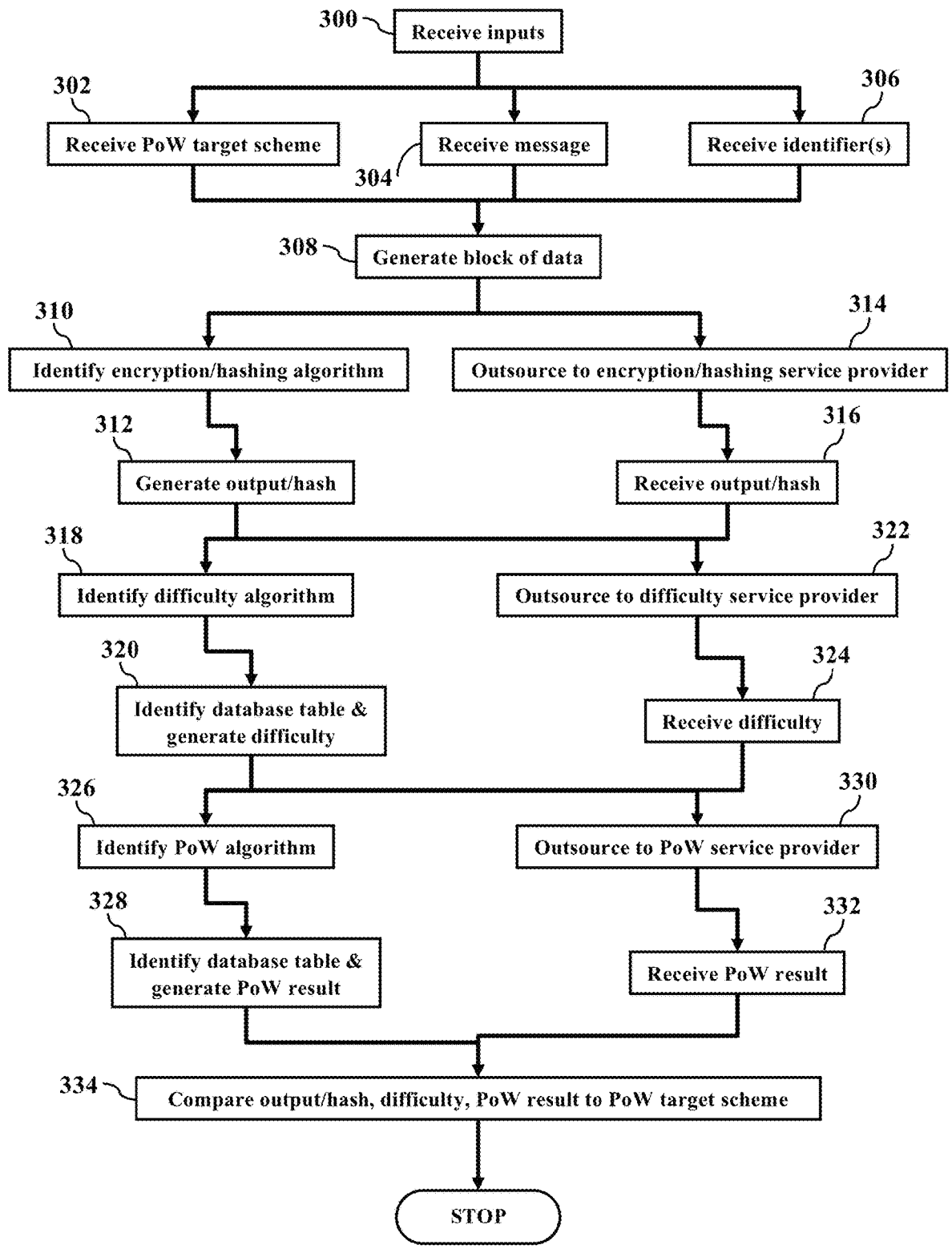
FIG. 44 is a flowchart illustrating a method or algorithm for mining blockchain transactions, according to exemplary embodiments.

FIG. 44 is a flowchart illustrating a method or algorithm for mining the blockchain transactions 32, according to exemplary embodiments. The inputs 24 (such as the blockchain transactions 32) may be received (Block 300). The proof-of-work ("PoW") target scheme 34 may be received (Block 302). The message 202 may be received (Block 304). The identifiers 200, 210, 214, and/or 250 may be received (Block 306). The block 40 of data may be generated (Block 308). The encryption algorithm 46 (such as the hashing algorithm 54) may be identified (Block 310) and the output 56 (such as the hash values 60) may be generated by encrypting/hashing the blockchain transactions 32 and/or the block 40 of data (Block 312). The encryption/hashing service provider 150 may be identified and the blockchain transactions 32 and/or the block 40 of data outsourced (Block 314). The output 56 (such as the hash values 60) may be received from the encryption/hashing service provider 150 (Block 316). The difficulty algorithm 48 may be identified (Block 318), the database table 90 may be generated or identified, and the difficulty 50 may be generated by executing the difficulty algorithm 48 (Block 320). The difficulty service provider 156 may be identified and the difficulty calculation outsourced (Block 322). The difficulty 50 may be received from the difficulty service provider 156 (Block 324). The PoW algorithm 52 may be identified (Block 326), the database table 90 may be generated or identified, and the PoW result 42 determined by executing the PoW algorithm 52 (Block 328). The PoW service provider 120 may be identified and the PoW calculation outsourced (Block 330). The PoW result 42 may be received from the PoW service provider 120 (Block 332). The output 56 (such as the hash values 60), the difficulty 50, and/or the PoW result 42 may be compared to the PoW target scheme 34 (Block 334).

Exemplary embodiments may win the block 40 of data. If the output 56, the difficulty 50, and/or the PoW result 42 satisfy the PoW target scheme 34, then the miner system 22 may submit the output 56, the difficulty 50, and/or the PoW result 42 to the blockchain network server 28. The miner system 22 may itself determine if the miner system 22 is the first to satisfy the PoW target scheme 34, or the miner system 22 may rely on the blockchain network server 28 to determine the first solution. When the miner system 22 is the first solver, the miner system 22 earns the right to add the block 40 of data to the blockchain 64. However, if the PoW target scheme 34 is not satisfied, the miner system 22 implements a change or modification and repeats.

Figure 45:
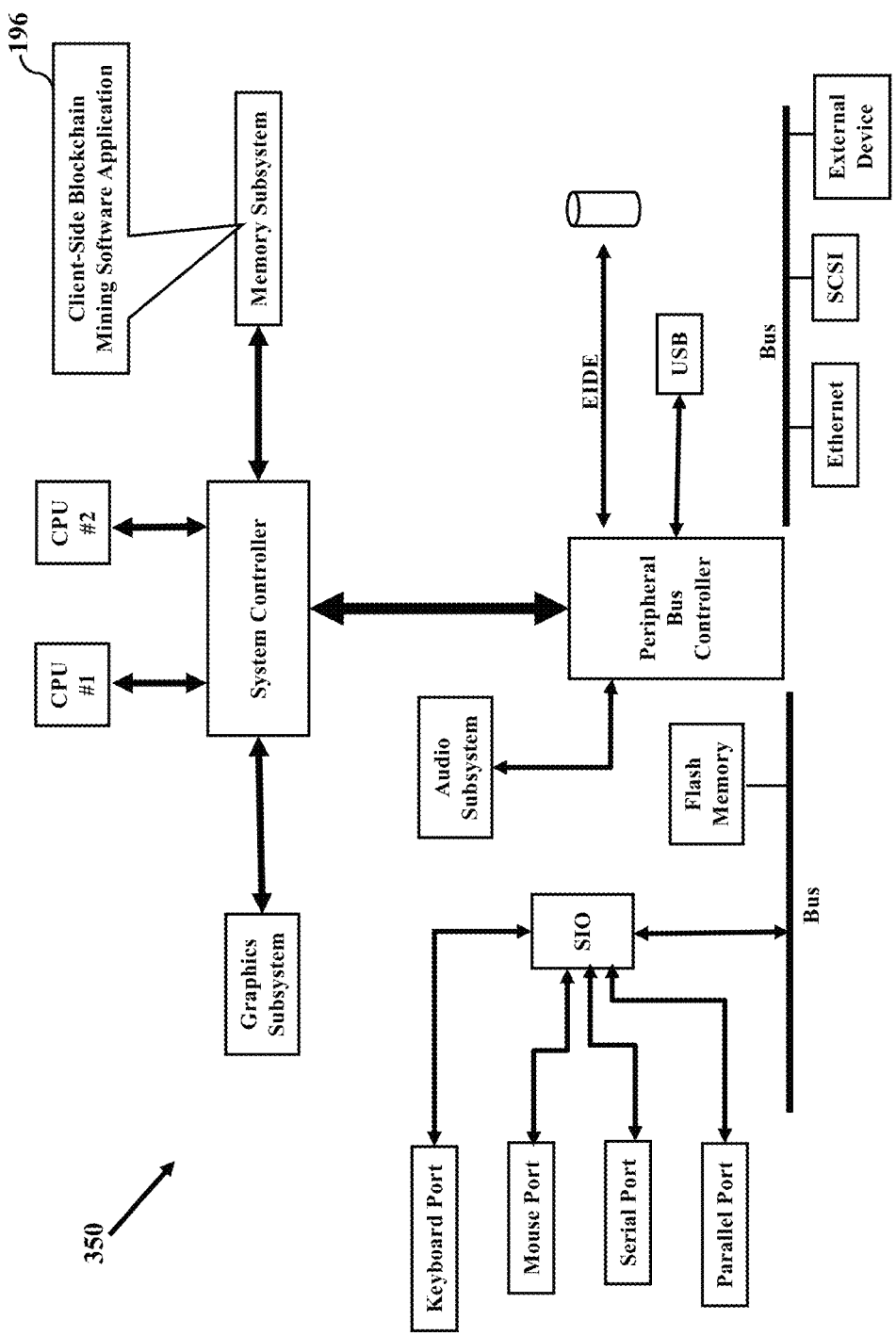
FIG. 45 depicts still more operating environments for additional aspects of exemplary embodiments.

FIG. 45 is a schematic illustrating still more exemplary embodiments. FIG. 45 is a more detailed diagram illustrating a processor-controlled device 350. As earlier paragraphs explained, the miner system 22 may be any home or business server/desktop 160, laptop computer 162, smartphone 164, tablet computer 166, or smartwatch 168, as exemplary embodiments allow these devices to have adequate processing and memory capabilities to realistically mine and win the block 40 of data (as explained with reference to FIG. 18). Moreover, exemplary embodiments allow any CPU-controlled device to realistically, and profitably, process the blockchain transactions 32, thus allowing networked appliances, radios/stereos, clocks, tools (such as OBDII diagnostic analyzers and multimeters), HVAC thermostats and equipment, network switches/routers/modems, and electric/battery/ICU engine cars, trucks, airplanes, construction equipment, scooters, and other vehicles 170.

Exemplary embodiments may be applied to any signaling standard. Most readers are familiar with the smartphone 164 and mobile computing. Exemplary embodiments may be applied to any communications device using the Global System for Mobile (GSM) communications signaling standard, the Time Division Multiple Access (TDMA) signaling standard, the Code Division Multiple Access (CDMA) signaling standard, the "dual-mode" GSM-ANSI Interoperability Team (GAIT) signaling standard, or any variant of the GSM/CDMA/TDMA signaling standard. Exemplary embodiments may also be applied to other standards, such as the I.E.E.E. 802 family of standards, the Industrial, Scientific, and Medical band of the electromagnetic spectrum, BLUETOOTH®, low-power or near-field, and any other standard or value.

Exemplary embodiments may be physically embodied on or in a computer-readable storage medium. This computer-readable medium, for example, may include CD-ROM, DVD, tape, cassette, floppy disk, optical disk, memory card, memory drive, and large-capacity disks. This computer-readable medium, or media, could be distributed to end-subscribers, licensees, and assignees. A computer program product comprises processor-executable instructions for processing or mining the blockchain transactions 32, as the above paragraphs explain.

While the exemplary embodiments have been described with respect to various features, aspects, and embodiments, those skilled and unskilled in the art will recognize the exemplary embodiments are not so limited. Other variations, modifications, and alternative embodiments may be made without departing from the spirit and scope of the exemplary embodiments.

The invention claimed is:

1. A method of deterring a specialized hardware processor in a blockchain environment, comprising:
   receiving, by a miner system, a proof-of-work target scheme associated with the blockchain environment;
   identifying, by the miner system, a proof-of-work mechanism specified by the proof-of-work target scheme associated with the blockchain environment;
   identifying, by the miner system, a separate hashing algorithm that is separately specified by the proof-of-work target scheme from the proof-of-work mechanism;
   identifying, by the miner system, a database table that is specified by the proof-of-work target scheme associated with the blockchain environment;
   receiving, by the miner system, a blockchain transaction associated with the blockchain environment;
   generating, by the miner system, a hash value by hashing the blockchain transaction using the separate hashing algorithm;
   generating, by the miner system, a randomized hash value by executing a bit shuffle operation that swaps a bit value in the hash value with an entry in the database table that is specified by the proof-of-work target scheme; and
   generating, by the miner system, a proof-of-work result by executing the proof-of-work mechanism using the randomized hash value generated by the executing of the bit shuffle operation;
   wherein the database table deters the specialized hardware processor in the blockchain environment.

2. The method of claim 1, further comprising identifying a difficulty algorithm that is specified by the proof-of-work target scheme associated with the blockchain environment.

3. The method of claim 2, further comprising generating a difficulty by executing the difficulty algorithm using the randomized hash value generated by the executing of the bit shuffle operation.

4. The method of claim 3, further comprising comparing the difficulty to the proof-of-work target scheme associated with the blockchain environment.

5. The method of claim 1, further comprising identifying a proof-of-work algorithm that is specified by the proof-of-work target scheme associated with the blockchain environment.

6. The method of claim 5, further comprising generating the proof-of-work result by executing the proof-of-work algorithm using the randomized hash value generated by the executing of the bit shuffle operation.

7. The method of claim 6, further comprising comparing the proof-of-work result to the proof-of-work target scheme associated with the blockchain environment.

8. A miner system for mining a blockchain transaction associated with a blockchain environment, comprising:
   a central processing unit; and
   a memory device storing instructions that, when executed by the central processing unit, perform operations, comprising:
   receiving a proof-of-work target scheme associated with the blockchain environment;
   identifying a proof-of-work mechanism specified by the proof-of-work target scheme associated with the blockchain environment;

identifying a separate hashing algorithm that is separately specified by the proof-of-work target scheme from the proof-of-work mechanism;

identifying a database table that is specified by the proof-of-work target scheme associated with the blockchain environment;

receiving the blockchain transaction associated with the blockchain environment;

generating a hash value by hashing the blockchain transaction using the separate hashing algorithm;

generating a randomized hash value by executing a bit shuffle operation that swaps a bit value in the hash value with an entry in the database table that is specified by the proof-of-work target scheme; and generating a proof-of-work result by executing the proof-of-work mechanism using the randomized hash value generated by the executing of the bit shuffle operation;

wherein the randomized hash value generated by the executing of the bit shuffle operation deters the mining of the blockchain transaction using an application-specific integrated circuit.

9. The miner system of claim 8, wherein the operations further comprise identifying a difficulty algorithm that is specified by the proof-of-work target scheme associated with the blockchain environment.

10. The miner system of claim 9, wherein the operations further comprise generating a difficulty by executing the difficulty algorithm using the randomized hash value generated by the executing of the bit shuffle operation.

11. The miner system of claim 10, wherein the operations further comprise comparing the difficulty to the proof-of-work target scheme associated with the blockchain environment.

12. The miner system of claim 8, wherein the operations further comprise identifying a proof-of-work algorithm that is specified by the proof-of-work target scheme associated with the blockchain environment.

13. The miner system of claim 12, wherein the operations further comprise generating the proof-of-work result by executing the proof-of-work algorithm using the randomized hash value generated by the executing of the bit shuffle operation.

14. The miner system of claim 13, wherein the operations further comprise comparing the proof-of-work result to the proof-of-work target scheme associated with the blockchain environment.

15. A memory device storing instructions that, when executed by a central processing unit, perform operations that mine a blockchain transaction associated with a blockchain environment, the operations comprising:

receiving a proof-of-work target scheme associated with the blockchain environment;

identifying a proof-of-work mechanism specified by the proof-of-work target scheme associated with the blockchain environment;

identifying a separate hashing algorithm that is separately specified by the proof-of-work target scheme from the proof-of-work mechanism;

identifying a database table that is specified by the proof-of-work target scheme associated with the blockchain environment;

receiving the blockchain transaction associated with the blockchain environment;

generating a hash value by hashing the blockchain transaction using the separate hashing algorithm;

generating a randomized hash value by executing a bit shuffle operation that swaps a bit value in the hash value with an entry in the database table that is specified by the proof-of-work target scheme; and generating a proof-of-work result by executing the proof-of-work mechanism using the randomized hash value generated by the executing of the bit shuffle operation;

wherein the randomized hash value generated by the executing of the bit shuffle operation deters a mining of the blockchain transaction using an application-specific integrated circuit.

16. The memory device of claim 15, wherein the operations further comprise identifying a difficulty algorithm that is specified by the proof-of-work target scheme associated with the blockchain environment.

17. The memory device of claim 16, wherein the operations further comprise generating a difficulty by executing the difficulty algorithm using the randomized hash value generated by the executing of the bit shuffle operation.

18. The memory device of claim 17, wherein the operations further comprise comparing the difficulty to the proof-of-work target scheme associated with the blockchain environment.

19. The memory device of claim 15, wherein the operations further comprise identifying a proof-of-work algorithm that is specified by the proof-of-work target scheme associated with the blockchain environment.

20. The memory device of claim 19, wherein the operations further comprise generating the proof-of-work result by executing the proof-of-work algorithm using the randomized hash value generated by the executing of the bit shuffle operation.

* * * * *